(12) United States Patent
Hunter et al.

(10) Patent No.: US 7,323,448 B2
(45) Date of Patent: *Jan. 29, 2008

(54) ANTIBACTERIAL AGENTS

(75) Inventors: Michael George Hunter, Cowley (GB); Raymond Paul Beckett, Cowley (GB); John Martin Clements, Cowley (GB); Mark Whittaker, Cowley (GB); Stephen John Davies, Cowley (GB); Lisa Marie Pratt, Cowley (GB); Zoe Marie Spavold, Cowley (GB); Steven Launchbury, Cowley (GB)

(73) Assignee: British Biotech Pharmaceuticals Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/497,277

(22) Filed: Aug. 2, 2006

(65) Prior Publication Data

US 2006/0276409 A1 Dec. 7, 2006

Related U.S. Application Data

(62) Division of application No. 10/901,065, filed on Jul. 29, 2004, which is a division of application No. 10/134,754, filed on Apr. 30, 2002, now Pat. No. 6,787,522, which is a division of application No. 09/355,489, filed as application No. PCT/GB99/00386 on Feb. 5, 1999, now Pat. No. 6,423,690.

(30) Foreign Application Priority Data

| Feb. 7, 1998 | (GB) | ................................ | 9802549.7 |
| Mar. 24, 1998 | (GB) | ................................ | 9806300.1 |
| May 16, 1998 | (GB) | ................................ | 9810463.1 |
| Dec. 22, 1998 | (GB) | ................................ | 9828318.7 |

(51) Int. Cl.
*A61K 38/05* (2006.01)
*C07C 259/04* (2006.01)
*C07K 5/06* (2006.01)

(52) U.S. Cl. ..................... 514/19; 562/621; 562/623
(58) Field of Classification Search ..................... None
See application file for complete search history.

(56) References Cited

U.S. PATENT DOCUMENTS

| 3,166,587 | A | 1/1965 | Bernstein et al. |
| 3,692,787 | A | 9/1972 | Roth et al. |
| 4,996,358 | A | 2/1991 | Handa et al. |
| 5,962,666 | A | 10/1999 | Lonetto |
| 6,045,795 | A | 4/2000 | Ulevitch et al. |
| 6,423,690 | B1 | 7/2002 | Hunter et al. |
| 6,441,042 | B1 | 8/2002 | Hunter et al. |
| 6,787,522 | B2 | 9/2004 | Hunter et al. |
| 6,908,911 | B1 | 6/2005 | Hunter et al. |

FOREIGN PATENT DOCUMENTS

| DE | 33 20 175 | 12/1984 |
| EP | 082088 | 6/1983 |
| EP | 236872 | 9/1987 |
| EP | 863152 | 9/1998 |
| EP | 879879 | 11/1998 |
| WO | WO 94/07527 | 4/1994 |
| WO | WO 94/10990 | 5/1994 |
| WO | WO 95/32944 | 12/1995 |
| WO | WO 96/16027 | 5/1996 |
| WO | WO 97/38705 | 10/1997 |
| WO | WO 98/38179 | 9/1998 |

OTHER PUBLICATIONS

Y Jin et al.: "Inhibition stereochemistry of hydroxamate inhibitors for thermolysin", Bioorganic & Medicinal Chemistry Letters, vol. 8, No. 24, 1998, pp. 3515-3518, XP002106374.
M-C Fournie-Zaluski et al.: "New bidentates as full inhibitors of enkephalin-degrading enzymes: synthesis and analgesic properties" Journal of Medicinal Chemistry, vol. 28, No. 9, 1985, pp. 1158-1169, XP002019770.
H.N. Weller, et al.: "Design of conformality Constrained Angiotensin-Converting Enzyme Inhibitors" Biochemical and Biophysical Research Communications, vol. 125, No. 1, 1984, pp. 82-89, XP002106375.
D. Mazel et al.: "Genetic Characteristics of Polypeptide Deformylase, A Distinctive Enzyme of Eubacterial Translation" EMBO, vol. 13, No. 4, pp. 914-923, XP002043973, (1994).
P.T. Ravi Rajagopalan et al.: "Peptide Deformylas: A New Type of Mononuclear Iron Protein", JAm.Chem.Soc., vol. 119, 1997, pp. 12418-21419, XP002106376.

*Primary Examiner*—Jeffrey Edwin Russel
(74) *Attorney, Agent, or Firm*—Banner & Witcoff, Ltd.

(57) ABSTRACT

Compounds of formula (I) or a pharmaceutically or veterinarily acceptable salts thereof

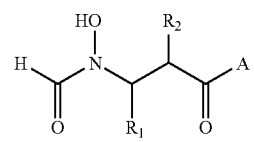

wherein $R_1$ represents hydrogen, $C_1$-$C_6$ alkyl or $C_1$-$C_6$ alkyl substituted by one or more halogen atoms; $R_2$ represents a group $R_{10}$-$(ALK)_m$-, and A represents (i) a group of formula (IA):

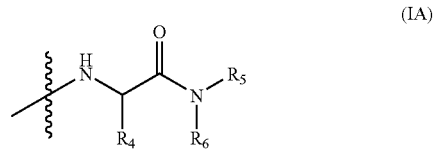

(IA)

wherein the compounds inhibit the activity of bacterial PDF enzyme.

2 Claims, No Drawings

ANTIBACTERIAL AGENTS

CROSS REFERENCE TO RELATED APPLICATIONS

This application is a divisional application of U.S. application Ser. No. 10/901,065, filed Jul. 29, 2004, now allowed, entitled "Antibacterial Agents", which is hereby incorporated by reference in its entirety, which is a divisional application of U.S. application Ser. No. 10/134,754, filed Apr. 30, 2002, now U.S. Pat. No. 6,787,522, issued Sep. 7, 2004, entitled "Antibacterial Agents" which is hereby incorporated by reference in its entirety, which is a divisional application of U.S. application Ser. No. 09/355,489, filed Jan. 7, 2000, now U.S. Pat. No. 6,423,690, issued Jul. 23, 2002, entitled "Antibacterial Agents" which is hereby incorporated by reference in its entirety, which is a U.S. National Phase Patent Application of International Patent Application PCT/GB99/00386 filed Feb. 5, 1999 which claims priority to GB 9802549.7, filed Feb. 7, 1998; GB 9806300.1 filed Mar. 24, 1998; GB 9810463.1 filed May 16, 1998; GB 9828318.7 filed Dec. 22, 1998 which are all incorporated by reference in their entirety.

FIELD OF THE INVENTION

This invention relates to the use of N-formyl hydroxylamine derivatives as antibacterial agents, to a novel class of such compounds, and to pharmaceutical and veterinary compositions comprising such compounds.

BACKGROUND TO THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as *Staphylococci, Streptococci, Mycobacteria* and *Enterococci*, resistant strains have evolved/arisen which makes them particularly difficult to eradicate. Examples of such strains are methicillin resistant *Staphylococcus aureus* (MRSA), methicillin resistant coagulase negative *Staphylococci* (MRCNS), penicillin resistant *Streptococcus pneumoniae* and multiply resistant *Enterococcus faecium*.

Pathogenic bacteria are often resistant to the aminoglycoside, β-lactam (penicillins and cephalosporins), and chloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849-62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidioglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant enterococci and β-lactam antibiotic-resistant bacteria, such as methicillin-resistant *Staphylococcus aureus*, is of utmost importance.

BRIEF DESCRIPTION OF THE INVENTION

This invention is based on the finding that certain N-formyl hydroxylamine derivatives have antibacterial activity, and makes available a new class of antibacterial agents. The inventors have found that the compounds with which this invention is concerned are antibacterial with respect to a range of Gram-positive and Gram-negative organisms. Furthermore, there is evidence that some compounds are antibacterial with respect to bacteria which are resistant to commonly used antibiotics such as vancomycin and the β-lactam antibiotics, for example methicillin-resistant *Staphylococcus aureus*.

Although it may be of interest to establish the mechanism of action of the compounds with which the invention is concerned, it is their ability to inhibit bacterial growth which makes them useful. However, it is presently believed that their antibacterial activity is due, at least in part, to intracellular inhibition of bacterial polypeptide deformylase (PDF) enzyme.

Bacterial polypeptide deformylases (PDF) (EC 3.5.1.31), are a conserved family of metalloenzymes (Reviewed: Meinnel T, Lazennec C, Villoing S, Blanquet S, 1997, Journal of Molecular Biology 267, 749-761) which are essential for bacterial viability, their function being to remove the formyl group from the N-terminal methionine residue of ribosome-synthesised proteins in eubacteria. Mazel et al. (EMBO J. 13(4):914-923, 1994) have recently cloned and characterised an *E. coli* PDF. As PDF is essential to the growth of bacteria and there is no eukaryotic counterpart to PDF, Mazel et al. (ibid), Rajagopalan et al. (J. Am. Chem. Soc. 119:12418-12419, 1997) and Becker et al., (J. Biol Chem. 273(19):11413-11416, 1998) have each proposed that PDF is an excellent anti-bacterial target.

Certain N-formyl hydroxylamine derivatives have previously been claimed in the patent publications listed below, although very few examples of such compounds have been specifically made and described:

| | |
|---|---|
| EP-B-0236872 | (Roche) |
| WO 92/09563 | (Glycomed) |
| WO 92/04735 | (Syntex) |
| WO 95/19965 | (Glycomed) |
| WO 95/22966 | (Sanofi Winthrop) |
| WO 95/33709 | (Roche) |
| WO 96/23791 | (Syntex) |
| WO 96/16027 | (Syntex/Agouron) |
| WO 97/03783 | (British Biotech) |
| WO 97/18207 | (DuPont Merck) |
| WO 98/38179 | (GlaxoWellcome) |
| WO 98/47863 | (Labs Jaques Logeais) |

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis. That prior art does not disclose or imply that N-formyl hydroxylamine derivatives have antibacterial activity.

In addition to these, U.S. Pat. No. 4,738,803 (Roques et al.) also discloses N-formyl hydroxylamine derivatives, however, these compounds are disclosed as enkephalinase inhibitors and are proposed for use as antidepressants and hypotensive agents. Also, WO 97/38705 (Bristol-Myers Squibb) discloses certain N-formyl hydroxylamine derivatives as enkephalinase and angiotensin converting enzyme inhibitors. This prior art does not disclose or imply that N-formyl hydroxylamine derivatives have antibacterial activity either.

DETAILED DESCRIPTION OF THE INVENTION

According to the first aspect of the present invention there is provided the use of a compound of formula (I) or a pharmaceutically or veterinarily acceptable salt thereof in the preparation of an antibacterial composition:

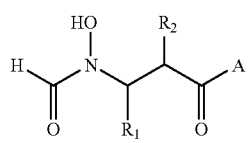

(I)

wherein:

$R_1$ represents hydrogen, or $C_1$-$C_6$ alkyl or $C_1$-$C_6$ alkyl substituted by one or more halogen atoms;

$R_2$ represents a group $R_{10}$—$(X)_n$-$(ALK)_m$- wherein
  $R_{10}$ represents hydrogen, or a $C_1$-$C_6$ alkyl, $C_2$-$C_6$ alkenyl, $C_2$-$C_6$ alkynyl, cycloalkyl, aryl, or heterocyclyl group, any of which may be unsubstituted or substituted by ($C_1$-$C_6$)alkyl, ($C_1$-$C_6$)alkoxy, hydroxy, mercapto, ($C_1$-$C_6$)alkylthio, amino, halo (including fluoro, chloro, bromo and iodo), trifluoromethyl, cyano, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$-$C_6$)alkyl group, and
  ALK represents a straight or branched divalent $C_1$-$C_6$ alkylene, $C_2$-$C_6$ alkenylene, or $C_2$-$C_6$ alkynylene radical, and may be interrupted by one or more non-adjacent —NH—, —O— or —S— linkages,
X represents —NH—, —O— or —S—, and
m and n are independently 0 or 1; and
A represents (i) a group of formula (IA), (IB), (IC) or (ID)

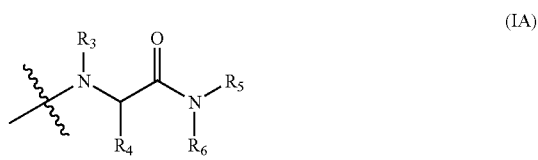

(IA)

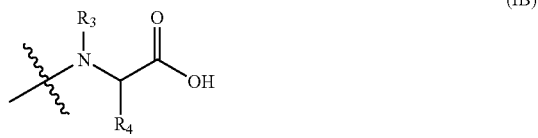

(IB)

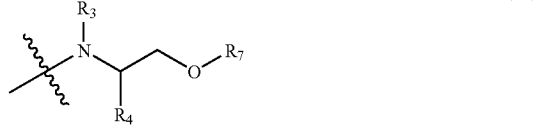

(IC)

(ID)
—NR$_5$R$_6$ wherein:
  $R_3$ represents hydrogen and $R_4$ represents the side chain of a natural or non-natural alpha amino acid or $R_3$ and $R_4$ when taken together with the nitrogen and carbon atoms to which they are respectively attached form an optionally substituted saturated heterocyclic ring of 5 to 8 atoms which ring is optionally fused to a carbocyclic or second heterocyclic ring,
  $R_5$ and $R_6$, independently represent hydrogen, or optionally substituted $C_1$-$C_8$ alkyl, cycloalkyl, aryl, aryl ($C_1$-$C_6$ alkyl), heterocyclic, or heterocyclic($C_1$-$C_6$ alkyl), or $R_5$ and $R_6$ when taken together with the nitrogen atom to which they are attached form an optionally substituted saturated heterocyclic ring of 3 to 8 atoms which ring is optionally fused to a carbocyclic or second heterocyclic ring, and
  $R_7$ represents hydrogen, $C_1$-$C_6$ alkyl, or an acyl group.

In another aspect, the invention provides a method for the treatment of bacterial infections in humans and non-human mammals, which comprises administering to a subject suffering such infection an antibacterially effective dose of a compound of formula (I) as defined above.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

According to a preferred embodiment, the various aspects of the invention can be applied against vancomycin-, quinolone- and "β-lactam"-resistant bacteria and the infections they cause.

On the hypothesis that the compounds (I) act by inhibition of intracellular PDF, the most potent antibacterial effect may be achieved by using compounds which efficiently pass through the bacterial cell wall. Thus, compounds which are highly active as inhibitors of PDF in vitro and which penetrate bacterial cells are preferred for use in accordance with the invention. It is to be expected that the antibacterial potency of compounds which are potent inhibitors of the PDF enzyme in vitro, but are poorly cell penetrant, may be improved by their use in the form of a prodrug, ie a structurally modified analogue which is converted to the parent molecule of formula (I), for example by enzymic action, after it has passed through the bacterial cell wall.

The invention also provides novel compounds of formula (I) above, or pharmaceutically or veterinarily acceptable salts thereof, wherein:

$R_1$ represents hydrogen, $C_1$-$C_6$ alkyl or $C_1$-$C_6$ alkyl substituted by one or more halogen atoms;

$R_2$ represents a group $R_{10}$-(ALK)$_m$- wherein $R_{10}$ represents hydrogen, or a $C_1$-$C_6$ alkyl, $C_2$-$C_6$ alkenyl, $C_2$-$C_6$ alkynyl, a cycloalkyl, aryl, or heterocyclyl group, any of which may be unsubstituted or substituted by ($C_1$-$C_6$)alkyl, ($C_1$-$C_6$)alkoxy, hydroxy, mercapto, ($C_1$-$C_6$)alkylthio, amino, halo (including fluoro, chloro, bromo and iodo), trifluoromethyl, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$-$C_6$)alkyl group, ALK represents a straight or branched divalent $C_1$-$C_6$ alkylene, $C_2$-$C_6$ alkenylene, $C_2$-$C_6$ alkynylene radical, and may be interrupted by one or more non-adjacent —NH—, —O— or —S— linkages, and m represents 0 or 1;

A represents a group of formula (IA), (IB), (IC) or (ID) above wherein:

$R_3$ represents hydrogen and $R_4$ represents the side chain of a natural or non-natural alpha amino acid or $R_3$ and $R_4$ when taken together with the nitrogen and carbon atoms to which they are respectively attached form an optionally substituted saturated heterocyclic ring of 5 to 8 atoms which ring is optionally fused to a carbocyclic or second heterocyclic ring, $R_5$ and $R_6$, independently represent hydrogen, or optionally substituted $C_1$-$C_8$ alkyl, cycloalkyl, aryl($C_1$-$C_6$ alkyl), non-aromatic heterocyclic, or heterocyclic ($C_1$-$C_6$ alkyl), or $R_5$ and $R_6$ when taken together with the nitrogen atom to which they are attached form an optionally substituted saturated heterocyclic ring of 3 to 8 atoms which ring is optionally fused to a carbocyclic or second heterocyclic ring, and $R_7$ represents hydrogen, $C_1$-$C_6$ alkyl, or an acyl group.

PROVIDED THAT (i) when A is a group of formula (IA) or (IB) and $R_2$ is $C_2$-$C_5$ alkyl then $R_4$ is not the side chain of a natural alpha amino acid or the side chain of a natural alpha-amino acid in which any functional substituents are protected, any amino groups are acylated, and any carboxyl groups are esterified;

(ii) when A is a group of formula (IA) or (IB) then $R_4$ is not a bicyclicarylmethyl group; and (iii) when A is a group of formula (IA) and $R_2$ is cyclopropylmethyl, cyclobutylmethyl or cyclopentylmethyl and one of $R_5$ and $R_6$ is hydrogen, then $R_4$ is not tert-butyl.

As used herein the term "($C_1$-$C_6$)alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent ($C_1$-$C_6$)alkylene radical" means a saturated hydrocarbon chain having from 1 to 6 carbon atoms and two-unsatisfied valencies.

As used herein the term "($C_2$-$C_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent ($C_2$-$C_6$)alkenylene radical" means a hydrocarbon chain having from 2 to 6 carbon atoms, at least one double bond, and two unsatisfied valencies.

As used herein the term "$C_2$-$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_2$-$C_6$)alkynylene radical" means a hydrocarbon chain having from 2 to 6 carbon atoms, at least one triple bond, and two unsatisfied valencies.

As used herein the term "cycloalkyl" means a saturated alicyclic moiety having from 3-8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3-8 carbon atoms and includes, for example, cyclopropenyl, cyclobutenyl, cyclopentenyl, cyclohexenyl, cycloheptenyl and cyclooctenyl. In the case of cycloalkenyl rings of from 5-8 carbon atoms, the ring may contain more than one double bond.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the term "heteroaryl" refers to a 5- or 6-membered aromatic ring containing one or more heteroatoms, and optionally fused to a benzyl or pyridyl ring; and to groups consisting of two covalently linked 5- or 6-membered aromatic rings each containing one or more heteroatoms; and to groups consisting of a monocyclic carbocyclic aromatic group covalently linked to a 5- or 6-membered aromatic rings containing one or more heteroatoms;. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the unqualified term "heterocyclyl" or "heterocyclic" includes "heteroaryl" as defined above, and in particular means a 5-7 membered aromatic or non-aromatic heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido and 1,3-dioxo-1,3-dihydro-isoindol-2-yl groups.

As used herein the term "acyl" means a group $R_{20}$C(O)— where $R_{20}$ is ($C_1$-$C_6$)alkyl, ($C_2$-$C_6$)alkenyl, ($C_3$-$C_7$)cycloalkyl, phenyl, heterocyclyl, phenyl($C_1$-$C_6$)alkyl, heterocyclyl($C_1$-$C_6$)alkyl, ($C_3$-$C_7$)cycloalkyl($C_1$-$C_6$)alkyl, phenyl ($C_2$-$C_6$)alkenyl, heterocyclyl($C_2$-$C_6$)alkenyl, ($C_3$-$C_7$) cycloalkyl($C_2$-$C_6$)alkenyl, any of which $R_{20}$ groups may be substituted.

As used herein, the term "bicyclicarylmethyl" means (i) a methyl group substituted by a monocyclic aryl or heteroaryl group which in turn is substituted by a monocyclic aryl or heteroaryl group, or (ii) a methyl group substituted by a monocyclic aryl or heteroaryl group to which is fused a second monocyclic aryl or heteroaryl group; and includes both unsubstituted and substituted bicyclicarylmethyl. Examples of such bicyclicarylmethyl groups include naphthyl, indolyl, quinolyl and isoquinolyl.

Unless otherwise specified in the context in which it occurs, the term "substituted" as applied to any moiety herein means substituted with up to four substituents, each of which independently may be $(C_1-C_6)$alkyl, benzyl, $(C_1-C_6)$alkoxy, phenoxy, hydroxy, mercapto, $(C_1-C_6)$alkylthio, amino, halo (including fluoro, chloro, bromo and iodo), trifluoromethyl, nitro, —COOH, —CONH$_2$, —COR$^A$, —COOR$^A$, —NHCOR$^A$, —CONHR$^A$, —NHR$^A$, —NR$^A$R$^B$, or —CONR$^A$R$^B$ wherein R$^A$ and R$^B$ are independently a $(C_1-C_6)$alkyl group. In the case where "substituted" means benzyl, the phenyl ring thereof may itself be substituted with any of the foregoing, except benzyl.

As used herein the terms "side chain of a natural alpha-amino acid" and "side chain of a non-natural alpha-amino acid" mean the group R$^x$ in respectively a natural and non-natural amino acid of formula NH$_2$—CH(R$^x$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example amino, carboxyl, hydroxy, mercapto, guanidyl, imidazolyl, or indolyl groups as in arginine, lysine, glutamic acid, aspartic acid, tryptophan, histidine, serine, threonine, tyrosine, and cysteine, such functional substituents may optionally be protected.

Likewise, in the side chains of non-natural alpha amino acids which contain functional substituents, for example amino, carboxyl, hydroxy, mercapto, guanidyl, imidazolyl, or indolyl groups, such functional substituents may optionally be protected.

The term "protected" when used in relation to a functional substituent in a side chain of a natural or non-natural alpha-amino acid means a derivative of such a substituent which is substantially non-functional. The widely used handbook by T. W. Greene and P. G. Wuts "Protective Groups in Organic Synthesis" Second Edition, Wiley, New York, 1991 reviews the subject. For example, carboxyl groups may be esterified (for example as a $C_1-C_6$ alkyl ester), amino groups may be converted to amides (for example as a NHCOC$_1$-C$_6$ alkyl amide) or carbamates (for example as an NHC(=O)OC$_1$-C$_6$ alkyl or NHC(=O) OCH$_2$Ph carbamate), hydroxyl groups may be converted to ethers (for example an OC$_1$-C$_6$ alkyl or a O(C$_1$-C$_6$ alkyl) phenyl ether) or esters (for example a OC(=O)C$_1$-C$_6$ alkyl ester) and thiol groups may be converted to thioethers (for example a tert-butyl or benzyl thioether) or thioesters (for example a SC(=O)C$_1$-C$_6$ alkyl thioester).

There are several actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the R$_2$ group is R; that of the carbon atom carrying the R$_4$ group (when asymmetric) is S; and that of the carbon atom carrying the R$_1$ group (when asymmetric) is R.

In the compounds of formula (I) as defined above for use according to the invention, and in the novel compounds of the invention of formula (II) as defined above (but subject to the provisos therein):

R$_1$ may be, for example, hydrogen, methyl, or trifluoromethyl. Hydrogen is currently preferred.

R$_2$ may be, for example:
  optionally substituted $C_1-C_8$ alkyl, $C_3-C_6$ alkenyl, $C_3-C_6$ alkynyl or cycloalkyl;
  phenyl($C_1-C_6$ alkyl)-, phenyl($C_3-C_6$ alkenyl)- or phenyl ($C_3-C_6$ alkynyl)- optionally substituted in the phenyl ring;
  cycloalkyl($C_1-C_6$ alkyl)-, cycloalkyl($C_3-C_6$ alkenyl)- or cycloalkyl($C_3-C_6$ alkynyl)- optionally substituted in the cycloalkyl ring;
  heterocyclyl($C_1-C_6$ alkyl)-, heterocyclyl($C_3-C_6$ alkenyl)- or heterocyclyl($C_3-C_6$ alkynyl)- optionally substituted in the heterocyclyl ring; or
  $CH_3(CH_2)_pO(CH_2)_q$— or $CH_3(CH_2)_pS(CH_2)_q$—, wherein p is 0, 1, 2 or 3 and q is 1, 2 or 3.

Specific examples of R$_2$ groups include methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl) prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at R$_2$ are n-propyl, n-butyl, n-pentyl, benzyl and cyclopentylmethyl.

In the case of R$_3$, hydrogen is presently preferred.

R$_4$ may be, for example
  the characterising group of a natural α amino acid, for example benzyl, or 4-methoxyphenylmethyl, in which any functional group may be protected, any amino group may be acylated and any carboxyl group present may be amidated; or
  a group -[Alk]$_n$R$_9$ where Alk is a $(C_1-C_6)$alkylene or $(C_2-C_6)$alkenylene group optionally interrupted by one or more —O—, or —S— atoms or —N(R$_{12}$)— groups [where R$_{12}$ is a hydrogen atom or a $(C_1-C_6)$alkyl group], n is 0 or 1, and R$_9$ is hydrogen or an optionally substituted phenyl, aryl, heterocyclyl, cycloalkyl or cycloalkenyl group or (only when n is 1) R$_9$ may additionally be hydroxy, mercapto, $(C_1-C_6)$alkylthio, amino, halo, trifluoromethyl, nitro, —COOH, —CONH$_2$, —COOR$^A$, —NHCOR$^A$, —CONHR$^A$, —NHR$^A$, —NR$^A$R$^B$, or CONR$^A$R$^B$ wherein R$^A$ and R$^B$ are independently a $(C_1-C_6)$alkyl group; or
  a benzyl group substituted in the phenyl ring by a group of formula —OCH$_2$COR$_8$ where R$_8$ is hydroxyl, amino, $(C_1-C_6)$alkoxy, phenyl$(C_1-C_6)$alkoxy, $(C_1-C_6)$ alkylamino, di$((C_1-C_6)$alkyl)amino, phenyl$(C_1-C_6)$ alkylamino; or a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl($C_1$-$C_6$)alkyl, hydroxy, formyl, amino, ($C_1$-$C_6$)alkylamino, di-($C_1$-$C_6$)alkylamino, mercapto, ($C_1$-$C_6$)alkylthio, hydroxy($C_1$-$C_6$)alkyl, mercapto($C_1$-$C_6$)alkyl or ($C_1$-$C_6$)alkylphenylmethyl; or a group —$CR_aR_bR_c$ in which:
  each of $R_a$, $R_b$ and $R_c$ is independently hydrogen, ($C_1$-$C_6$)alkyl, ($C_2$-$C_6$)alkenyl, ($C_2$-$C_6$)alkynyl, phenyl($C_1$-$C_6$)alkyl, ($C_3$-$C_8$)cycloalkyl; or $R_c$ is hydrogen and $R_a$ and $R_b$ are independently phenyl or heteroaryl such as pyridyl; or $R_c$ is hydrogen, ($C_1$-$C_6$)alkyl, ($C_2$-$C_6$)alkenyl, ($C_2$-$C_6$)alkynyl, phenyl($C_1$-$C_6$)alkyl, or ($C_3$-$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$-$C_6$)alkyl, ($C_2$-$C_6$)alkenyl, ($C_2$-$C_6$)alkynyl, phenyl($C_1$-$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, ($C_1$-$C_4$)perfluoroalkyl, —$CH_2OH$, —$CO_2$($C_1$-$C_6$)alkyl, —O($C_1$-$C_6$)alkyl, —O($C_2$-$C_6$)alkenyl, —S($C_1$-$C_6$)alkyl, —SO($C_1$-$C_6$)alkyl, —$SO_2$($C_1$-$C_6$) alkyl, —S($C_2$-$C_6$)alkenyl, —SO($C_2$-$C_6$)alkenyl, —$SO_2$($C_2$-$C_6$)alkenyl or a group -Q-W wherein Q represents a bond or —O—, —S—, —SO— or —$SO_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —$CO_2H$, —$CO_2$($C_1$-$C_6$)alkyl, —$CONH_2$, —CONH($C_1$-$C_6$)alkyl, —CONH($C_1$-$C_6$alkyl)$_2$, —CHO, —$CH_2OH$, ($C_1$-$C_4$)perfluoroalkyl, —O($C_1$-$C_6$)alkyl, —S($C_1$-$C_6$)alkyl, —SO($C_1$-$C_6$)alkyl, —$SO_2$($C_1$-$C_6$)alkyl, —$NO_2$, —$NH_2$, —NH($C_1$-$C_6$)alkyl, —N(($C_1$-$C_6$)alkyl)$_2$, —NHCO($C_1$-$C_6$)alkyl, ($C_1$-$C_6$)alkyl, ($C_2$-$C_6$)alkenyl, ($C_2$-$C_6$)alkynyl, ($C_3$-$C_8$)cycloalkyl, ($C_4$-$C_8$)cycloalkenyl, phenyl or benzyl.

Examples of particular $R_4$ groups include methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxyethyl, 2-carboxyethyl, 2-methylcarbamoylethyl, 2-carbamoylethyl, and 4-aminobutyl. Presently preferred $R_4$ groups include tert-butyl, iso-butyl, benzyl and methyl.

$R_3$ and $R_4$ when taken together with the nitrogen and carbon atoms to which they are respectively attached may form an optionally substituted saturated heterocyclic ring of 5 to 8 atoms. For example, $R_3$ and $R_4$ may form a bridge between the nitrogen and carbon atoms to which they are attached, said bridge being represented by the divalent radical —$(CH_2)_{3-6}$—, or —$(CH_2)_r$—O—$(CH_2)_s$—, or —$(CH_2)_r$—S—$(CH_2)_s$—, wherein r and s are each independently 1, 2 or 3 with the proviso that r+s=2, 3, 4, or 5.

$R_5$ and $R_6$ may independently be, for example, hydrogen, methyl, ethyl, tert-butyl, cyclopentyl, cyclohexyl, 1,1,3,3-tetramethylbutyl,benzyl, or 2-hydroxyethyl; or $R_5$ and $R_6$ when taken together with the nitrogen atom to which they are attached may form a saturated 5- to 8-membered monocyclic N-heterocyclic ring which is attached via the N atom and which optionally contains —N($R_{11}$)— wherein $R_{11}$ is hydrogen or $C_1$-$C_6$ alkyl, benzyl, acyl, or an amino protecting group, O, S, SO or $SO_2$ as a ring member, and/or is optionally substituted on one or more C atoms by hydroxy, $C_1$-$C_6$ alkyl, hydroxy($C_1$-$C_6$ alkyl)-, $C_1$-$C_6$ alkoxy, oxo, ketalised oxo, amino, mono($C_1$-$C_6$ alkyl)amino, di($C_1$-$C_6$ alkyl)amino, carboxy, $C_1$-$C_6$ alkoxycarbonyl, hydroxymethyl, $C_1$-$C_6$ alkoxymethyl, carbamoyl, mono($C_1$-$C_6$ alkyl)carbamoyl, di($C_1$-$C_6$ alkyl)carbamoyl, or hydroxyimino.

Examples of such rings are substituted or unsubstituted 1-pyrrolidinyl, piperidin-1-yl, 1-piperazinyl, hexahydro-1-pyridazinyl, morpholin-4-yl, tetrahydro-1,4-thiazin-4-yl, tetrahydro-1,4-thiazin-4-yl 1-oxide, tetrahydro-1,4-thiazin-4-yl 1,1-dioxide, hexahydroazipino, or octahydroazocino. Substituted examples of the foregoing are 2-(methylcarbamoyl)-1-pyrrolidinyl, 2-(hydroxymethyl)-1-pyrrolidinyl, 4-hydroxypiperidino, 2-(methylcarbamoyl)piperidino, 4-hydroxyiminopiperidino, 4-methoxypiperidino, 4-methylpiperidin-1yl, 4-benzylpiperidin-1-yl, 4-acetylpiperidin-1-yl, 4-methyl-1-piperazinyl, 4-phenyl-1-piperazinyl, 1,4-dioxa-8-azaspiro[4,5]decan-8-yl, hexahydro-3-(methylcarbamoyl)-2-pyridazinyl, and hexahydro-1-(benzyloxycarbonyl)-2-pyridazinyl, decahydroisoquinolin-2-yl, and 1,2,3,4-tetrahydroisoquinolin-2-yl.

When A is a group of formula (IA), it is currently preferred that $R_5$ be methyl or hydrogen, and $R_6$ be methyl.

$R_7$ may be, for example, hydrogen, or a group $R_{20}$C(O)— where $R_{20}$ is a ($C_1$-$C_6$)alkyl group such as methyl or ethyl.

Specific examples of compounds useful as antibacterial agents in accordance with the invention include those of the specific Examples herein. Preferred novel compounds of the invention include 2R (or S)-[(Formyl-hydroxy-amino)-methyl]-hexanoic acid (1S-dimethylcarbamoyl-ethyl)-amide and 2R (or S)-[(Formyl-hydroxy-amino)-methyl]-3-cyclopentyl-propionic acid (1S-dimethyl-carbamoyl-2,2-dimethyl-propyl)-amide and their pharmaceutically and veterinarily acceptable salts.

Compounds with which the invention is concerned the invention may be prepared by deprotecting an O-protected N-formyl-N-hydroxyamino compound of formula (II):

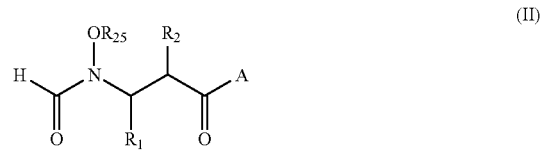

(II)

in which $R_1$, $R_2$, and A are as defined in general formula (I) and $R_{25}$ is a hydroxy protecting group removable to leave a hydroxy group by hydrogenolysis or hydrolysis. Benzyl is a preferred $R_{25}$ group for removal by hydrogenolysis, and tert-butyl and tetrahydropyranyl are preferred groups for removal by acid hydrolysis.

Compounds of formula (II) wherein A is a group of formula (IA), (IB), (IC) or (ID) may be prepared by causing an acid of formula (III) or an activated derivative thereof to react with an amine of formula (IVA), (IVB), (IVC) or (IVD) respectively

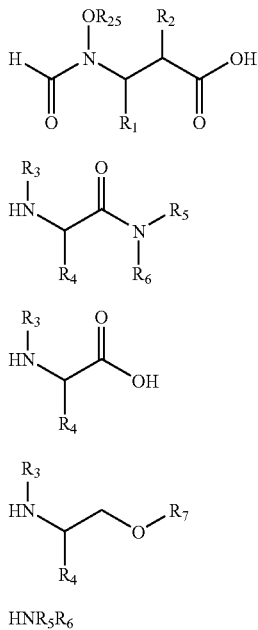

wherein $R_1$, $R_2$, $R_3$, $R_4$, $R_5$, $R_6$ and $R_7$ are as defined in general formula (I) except that the —OH group in (IVB) and any substituents in $R_1$, $R_2$, $R_3$, $R_4$, $R_5$, $R_6$ and $R_7$ which are potentially reactive in the coupling reaction may themselves be protected from such reaction, and $R_{25}$ is as defined in relation to formula (II) above, and optionally removing protecting groups from the —OH group in (IVB) and $R_1$, $R_2$, $R_3$, $R_4$, $R_5$, $R_6$ and $R_7$.

Compounds of formula (III) may be prepared by N-formylation, for example using acetic anhydride and formic acid, or 1-formylbenzotriazole, of compounds of formula (V)

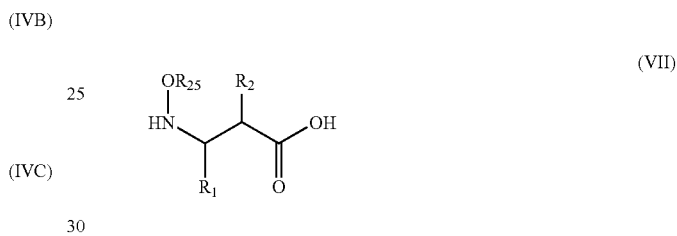

wherein $R_1$, $R_2$ and $R_{25}$ are as defined in relation to formula (II) and X is either a chiral auxiliary or an $OR_{26}$ group wherein $R_{26}$ is hydrogen or a hydroxy protecting group. In the case where X is an $OR_{26}$ group or a chiral auxiliary the hydroxy protecting group or auxiliary is removed after the formylation step to provide the compound of formula (V). Suitable chiral auxiliaries include substituted oxazolidinones which may be removed by hydrolysis in the presence of base.

In an alternative procedure compounds of general formula (II) may be prepared by N-formylation, for example using acetic anhydride and formic acid, or 1-formylbenzotriazole, of compounds of formula (VI)

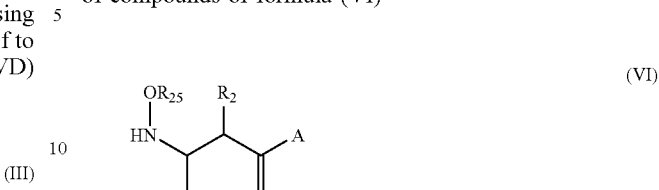

wherein $R_1$, $R_2$, $R_{25}$ and A are as defined in relation to formula (II).

Compounds of formula (VI) wherein A is a group of formula (IA), (IB), (IC) or (ID) may be prepared by causing an acid of general formula (VII) or an activated derivative thereof

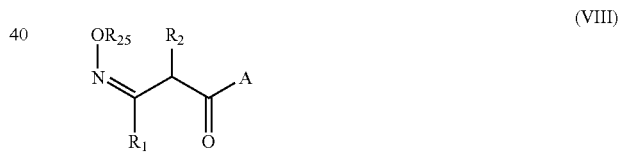

wherein $R_1$, $R_2$ and $R_{25}$ are as defined in relation to formula (II) to react with an amine of formula (IVA), (IVB), (IVC) or (IVD) respectively as defined above.

Alternatively compounds of general formula (VI) may be prepared by reduction of an oxime of general formula (VIII).

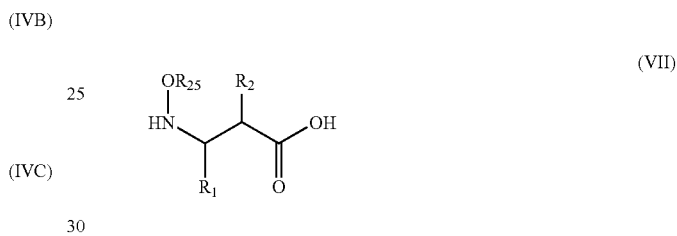

Reducing agents include certain metal hydrides (e.g. sodium cyanoborohydride in acetic acid, triethylsilane or borane/pyridine) and hydrogen in the presence of a suitable catalyst.

In an alternative procedure compounds of general formula (II) wherein $R_1$ and $R_2$ are as defined in general formula (I), $R_{25}$ is a hydroxy protecting group as defined above and A is a group of formula (IA) wherein $R_3$, $R_4$, $R_5$ are as defined in general formula (IA) and $R_6$ is hydrogen may be prepared by a 4-component Ugi reaction of carboxylic acid of general formula (III) as defined above, an amine of formula (IX), an aldehydes of formula (X) and an isonitrile of formula (XI)

$R_3$—$NH_2$ (IX)

$R_4$—CHO (X)

$R_5$—CN (XI)

wherein $R_3$, $R_4$ and $R_5$ are as defined above.

A compound of general formula (V) may be prepared by reduction of an oxime of general formula (XI)

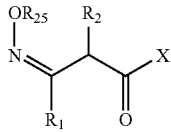

wherein $R_1$, $R_2$, and $R_{25}$ are as defined above, and X is either an $OR_{26}$ group as defined above or a chiral auxiliary. Reducing agents include certain metal hydrides (eg sodium cyanoborohydride in acetic acid, triethylsilane or borane/pyridine) and hydrogen in the presence of a suitable catalyst. Following the reduction when the group X is a chiral auxiliary it may be optionally converted to a $OR_{26}$ group.

A compound of general formula (XI) can be prepared by reaction of a β-keto carbonyl compound of general formula (XII)

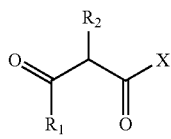

wherein $R_1$, $R_2$, and X are as defined above, with an O-protected hydroxylamine.

β-keto carbonyl compounds (XII) may be prepared in racemic form by formylation or acylation of a carbonyl compound of general formula (XIII)

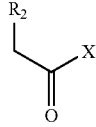

wherein $R_2$ and X are as defined above, with a compound of general formula (XIV)

wherein $R_1$ is as defined above and Z is a leaving group such as halogen or alkoxy, in the presence of a base.

Another method for the preparation of a compound of general formula (V) is by Michael addition of a hydroxylamine derivative to α,β-unsaturated carbonyl compounds of general formula (XV)

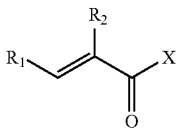

wherein $R_1$, $R_2$, and X are as defined above. Following the Michael addition reaction, when the group X is a chiral auxiliary it may be optionally converted to a $OR_{26}$ group. The α,β-unsaturated carbonyl compounds (XV) may be prepared by standard methods.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle. Intra-venous infusion is another route of administration for the compounds used in accordance with the invention.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The finding that compounds with PDF inhibitory activity can inhibit or prevent bacterial growth, opens up a novel approach for identifying new antibacterial agents by screening test compounds for activity as inhibitors of PDF in vitro, followed by confirmation of their antibacterial ability using bacterial growth inhibition studies. This finding also makes available (i) the use of compounds with PDF inhibitory activity as antibacterial agents, and (ii) a method for the treatment of bacterial infection or contamination by applying or administering a compound which inhibits the activity of bacterial PDF.

According to a further aspect of the invention therefore, there is provided a method for the identification of antibacterial compounds, comprising screening test compounds for their ability to inhibit PDF in vitro, selecting those compounds which exhibit said ability and testing these for their ability to inhibit bacterial growth. The ability to inhibit bacterial growth can be performed using classical plate or broth culture bacterial growth inhibition studies, such as those performed in the Biological Examples herein.

A suitable in vitro PDF inhibition screen may comprise mixing together PDF, a PDF substrate, preferably labelled with a detectable marker, and the test compound and assessing after a suitable length of time whether or not the presence of the test compound inhibits the ability of PDF to deformylate the substrate.

In a preferred embodiment, the cleaved substrate is detected with a fluorogenic marker such as fluorescamine. On removal of the formyl group from the N-terminal methionine of the PDF substrate, the free amino group reacts with fluorescamine generating a fluorescent product.

An alternative screen involves assessing whether a protein expressed by bacteria that express endogenous (or recombinantly expressed) PDF, when grown in the presence of a test compound, yields suitable substrate for N-terminal sequencing, or yields a lesser amount of substrate, than protein expressed from the same bacteria grown in the absence of the test compound. Such a method could be based on that used in the Biological Examples herein.

The person skilled in the art will be able to develop, without inventive input, alternative methods for screening test compounds for their ability to inhibit bacterial PDF.

The natural antibiotic actinonin (see for example J.C.S Perkin I1975, 819) is a hydroxamic acid derivative of Structure (A):

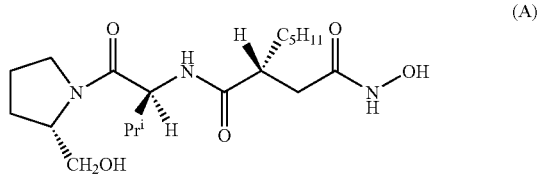

(A)

In addition to actinonin, various structural analogues of actinonin have also been shown to have antibacterial activity (see for example Broughton et al. (Devlin et al. Journal of the Chemical Society. Perkin Transactions 1 (9):830-841, 1975; Broughton et al. Journal of the Chemical Society. Perkin Transactions 1 (9):857-860, 1975)

To date, however, the mechanism underlying the antibacterial activity of actinonin has not been known. The present inventors have found that actinonin inhibits the activity of bacterial PDF.

The matlystatin group of compounds share a number of structural similarities with actinonin. Both are peptidic molecules with functional hydroxamic acid metal binding groups (Ogita et al., J. Antibiotics. 45(11):1723-1732; Tanzawa et al., J. Antibiotics. 45(11):1733-1737; Haruyama et al., J. Antibiotics. 47(12):1473-1480; Tamaki et al., J. Antibiotics. 47(12):1481-1492). The matlystatins and their close structural analogues are characterised by the presence in the molecule of a divalent piperazin-1,6-diyl group, i.e.

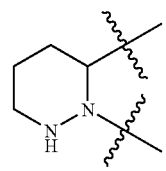

In view of their close structural similarity to actinonin, the observation that actinonin inhibits PDF implies that matlystatin compounds may also inhibit PDF.

According to a further aspect of the present invention there is provided the use of a compound which inhibits the activity of bacterial PDF, in the preparation of an antibacterial composition or agent, provided that (i) the compound is not of formula (XI)

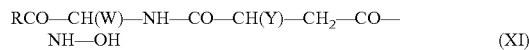

wherein, (a) R is a cyclic amino group, W is hydrogen, methyl, isopropyl, isobutyl or benzyl, and Y is hydrogen, $C_1$-$C_6$ alkyl, phenyl, benzyl, 4-chlorophenylmethyl, 4-nitrophenylmethyl, or 4-aminophenylmethyl; or, (b) R is 2-pyridylamino or 2-thiazolylamino, W is isopropyl and Y is n-pentyl; or, (c) R is diethylamino, W is methyl or isopropyl and Y is n-pentyl;

or (ii) the compound is not one containing a divalent piperazin-1, 6-diyl group, i.e. a group of formula (XII):

According to a further aspect of the invention there is provided a method of treating bacterial infection or contamination by administering to a patient suffering such infection or contamination, or applying to the site of such infection or contamination, an antibacterially effective amount of a compound which inhibits the activity of bacterial PDF enzyme, provided that the compound is not one provided in the provisos in the immediately preceeding paragraph.

These provisos exclude actinonin and its antibacterially active analogues as disclosed in Devlin et al., Journal of the Chemical Society. Perkin Transactions 1 (9):830-841, 1975 and Broughton et al. Journal of the Chemical Society. Perkin Transactions 1 (9):857-860, 1975, and the matlystatin compounds disclosed in Ogita et al., J. Antibiotics. 45(11):1723-1732; Tanzawa et al., J. Antibiotics. 45(11):1733-1737; Haruyama et al., J. Antibiotics. 47(12):1473-1480 and Tamaki et al., J. Antibiotics. 47(12):1481-1492.

The following examples illustrate embodiments of the invention. L-tert-Leucine-N-methylamide and L-tert-leucine-N,N-dimethylamide and other amino acid derivatives were prepared according to established literature methods.

The following abbreviations have been used throughout:

| | |
|---|---|
| DMF | N,N-Dimethylformamide |
| EDC | N-Ethyl-N'-(3-dimethylaminopropyl)carbodiimide hydrochloride |
| HOAt | 1-Hydroxy-7-aza-benzotriazole |
| HOBt | 1-Hydroxybenzotriazole |
| HPLC | High performance liquid chromatography |
| LRMS | Low resolution mass spectrometry |
| TLC | Thin layer chromatography |

$^1$H and $^{13}$C NMR spectra were recorded using a Bruker AC 250E spectrometer at 250.1 and 62.9 MHz, respectively. Mass spectra were obtained using a Perkin Elmer Sciex API 165 spectrometer using both positive and negative ion modes. Infra-red spectra were recorded on a Perkin Elmer PE 1600 FTIR spectrometer.

EXAMPLE 1

2R (or S)-[(Formyl-hydroxy-amino)-methyl]-hexanoic acid-(2,2-dimethyl-1S-methyl-carbamoyl-propyl)-amide

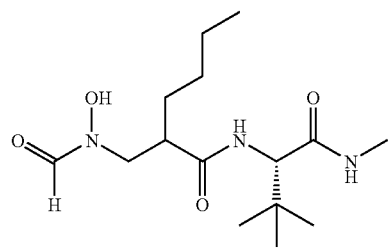

The title compound was prepared according to the route outlined in Scheme 1 and as described in detail below:

Scheme 1

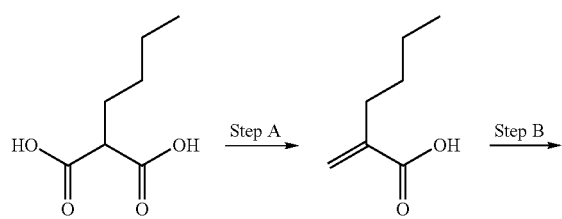

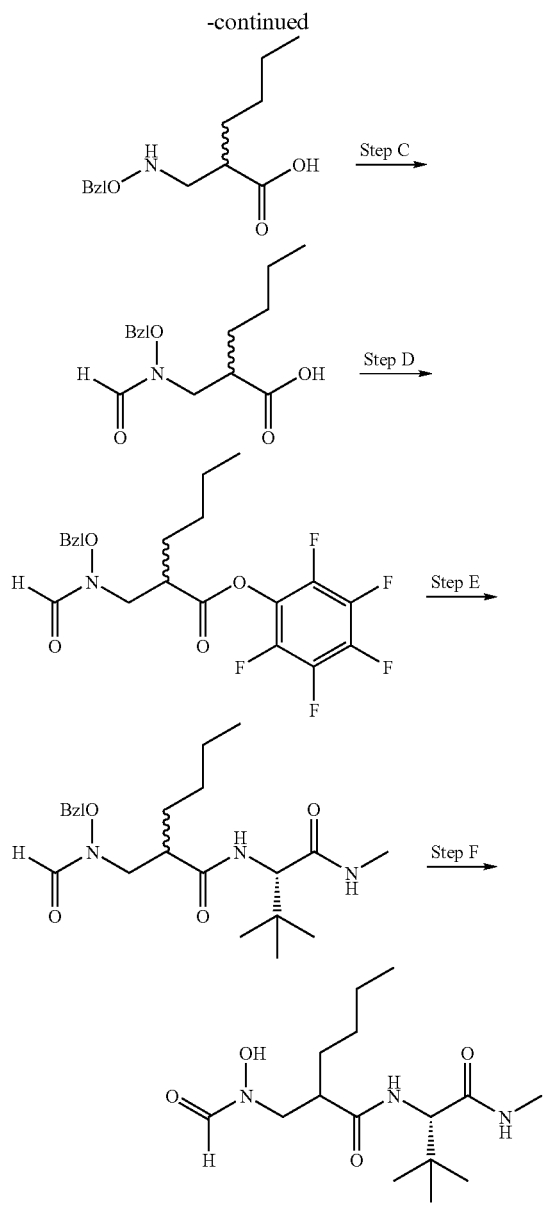

Reagents and conditions:
A. piperidine, HCHO, EtOH, 80° C., o/n;
B. H$_2$NOBzl, 80° C. o/n;
C. HCOOH, Ac$_2$O;
D. Pentafluorophenol, EDC, CH$_2$Cl$_2$;
E. H-tert-LeuNHMe, DMF, 35° C.;
F. H$_2$, 10% Pd/C, EtOAc/EtOH.

STEP A: 2-Butyl-acrylic acid

Butylmalonic acid (25 g, 156 mmol) was dissolved in ethanol (250 ml) and 37% formaldehyde solution (15.45 ml, 156 mmol) was added followed by piperidine (47 ml, 624 mmol). The mixture was stirred overnight at 80° C. under a reflux condenser. The solvents were removed under reduced pressure and the residue was diluted with 1M hydrochloric acid and extracted with dichloromethane (3×30 ml). The combined organic extracts were washed with brine, dried over anhydrous magnesium sulfate, filtered and evaporated to afford the desired product as a yellow oil (25 g, with residual solvent). $^1$H-NMR: δ (CDCl$_3$), 10.04 (1H, brs), 6.22 (1H, s), 5.57 (1H, d, J=1.3 Hz), 2.30 (2H, t, J=6.9 Hz), 1.38 (4H, m), and 0.91 (3H, t, J=7.2 Hz).

STEP B: 2RS-(Benzyloxy-amino-methyl)-hexanoic acid

A mixture of 2-butyl-acrylic acid (3.43 g, 27.1 mmol) and O-benzylhydroxylamine (5 g, 40.65 mmol) were heated at 80° C. overnight. The mixture was cooled to room temperature, diluted with ethyl acetate (40 ml), and washed with 1M hydrochloric acid (3×20 ml), saturated sodium hydrogen carbonate solution (2×20 ml) and brine (2×20 ml), dried over anhydrous magnesium sulfate, filtered and evaporated to leave the title compound as a white solid (2.62 g, 39%). $^1$H-NMR: δ (CDCl$_3$), 8.05 (1H, br s), 7.35 (5H, m), 5.00 (2H, m), 3.28 (2H, m), 2.98 1H, m), 1.31 (6H, m) and 0.88 (3H, t, J=5.0 Hz).

Step C: 2RS-[(Benzyloxy-formyl-amino)-methyl]-hexanoic acid

2RS-(Benzyloxyamino-methyl)-hexanoic acid (2.62 g, 10.51 mmol) was dissolved in formic acid (4 ml, 105 mmol) and acetic anhydride (1.9 ml, 21.02 mmol) and stirred overnight at room temperature. The solution was diluted with ethyl acetate (40 ml), washed with water (2×20 ml), saturated sodium hydrogen carbonate solution (20 ml) and brine (20 ml), dried over anhydrous magnesium sulfate, filtered and evaporate to leave the desired product as a yellow oil (2.9 g, 99%). $^1$H-NMR: δ (CDCl$_3$, rotamers), 8.21 (0.5H, s), 8.14 (0.5H, s), 7.37 (5H, m), 4.98 (2H, m), 3.86 (1H, m), 3.27 (0.5H, dd, J=6.0, 14.0 Hz), 2.93 (0.5H, m), 2.77 (1H, m), 1.50 (2H, m), 1.30 (4H, m) and 0.88 (3H, m).

STEP D: 2RS-[(Benzyloxy-formyl-amino)-methyl]-hexanoic acid pentafluorophenyl ester 2RS-[(Benzyloxy-formyl-amino)-methyl]-hexanoic acid (30.72 g, 110 mmol) and penta-fluorophenol (26.31 g, 143 mmol) were dissolved in dichloromethane (150 ml) and the solution was stirred and cooled in an ice bath during addition of EDC (25.3 g, 131 mmol). The reaction mixture was allowed to warm to room temperature and stirred overnight. The solution was washed successively with 1M hydrochloric acid (2×50 ml), 0.5M sodium carbonate (2×50 ml) and brine (50 ml), dried over anhydrous magnesium sulfate and filtered. The filtrate was evaporated under reduced pressure and the residue was purified by flash chromatography (silica gel, dichloromethane) to afford the title compound as a colourless oil (15.0 g, 31%). $^1$H-NMR: δ (CDCl$_3$, rotamers), 8.17 (1H, br s), 7.37 (5H, m), 4.95-4.70 (2H, br m), 4.10-3.75 (2H, br m), 3.10 (1H, br s), 1.88-1.55 (2H, m), 1.39 (4H, m) and 0.92 (3H, t, J=7.0 Hz).

STEP E: 2R (or S)-[(Benzyloxy-formyl-amino)-methyl]-hexanoic acid-(2,2-dimethyl-1-methyl-carbamoyl-propyl)-amide 2RS-[(Benzyloxy-formyl-amino)-methyl]-hexanoic acid pentafluorophenyl ester (5 g, 11 mmol) and tert-leucine N-methylamide (1.62 g, 11 mmol) were dissolved in DMF (60 ml) and the mixture was stirred overnight at 35° C. The solvent was removed under reduced pressure and the residue was redissolved in dichloromethane. The solution was washed successively with 0.5 M sodium carbonate, 1.0 M hydrochloric acid and brine, dried over anhydrous magnesium sulfate and filtered. The two diastereoisomeric products were separated by flash chromatography (silica gel, gradient elution with 30% to 0% hexane in ethyl acetate). Diastereoisomer A (higher R$_f$): $^1$H-NMR: δ (CDCl$_3$, rotamers), 8.12, 7.87 (1H, 2br s), 7.27 (5H, m), 6.26 (1H, d, J=8.7 Hz), 5.78 (1H, brs), 4.91-4.60 (2H, br m), 4.15 (1H, d, J=9.2 Hz), 3.75 (2H, br m), 2.79 (3H, d, J=4.8 Hz), 2.56 (1H, m), 1.60-1.35 (2H, br m), 1.24 (4H, m), 0.96 (9H, s) and 0.86 (3H, t, J=6.7 Hz). Diastereoisomer B (lower R$_f$): $^1$H-NMR: δ (CDCl$_3$, rotamers), 8.16, 7.88 (1H, 2br s), 7.27 (5H, m), 6.28 (1H, d, J=8.9 Hz), 5.70-5.44 (1H, br s), 4.98-4.61 (2H, br m), 4.14 (1H, d, J=9.2 Hz), 3.78-3.62 (2H, br m), 2.85-2.60 (3H, br m), 2.47 (1H, m), 1.72-1.25 (6H, br m), 0.98 (9H, s) and 0.88 (3H, t, J=6.7 Hz).

STEP F: 2R (or S)-[(Formyl-hydroxy-amino)-methyl]-hexanoic acid-(2,2-dimethyl-1S-methylcarbamoyl-propyl)-amide 2-[(Benzyloxy-formyl-amino)-methyl]-hexanoic acid-(2,2-dimethyl-1-methylcarbamoyl-propyl)-amide (diastereoisomer A) (1.0 g, 2.5 mmol) was dissolved in a mixture of ethyl acetate (20 ml) and ethanol (1 ml) and the solution was placed under an argon atmosphere. 10% palladium on charcoal was added and a fine stream of hydrogen gas was bubbled through the suspension. After 40 minutes TLC analysis revealed that all the starting material had been consumed leaving a more polar, ferric chloride positive species. The system was flushed with argon before removing the catalyst by filtration. The filtrate was evaporated to dryness to leave the title compound as an off-white foam (810 mg, including residual solvent). $^1$H-NMR: δ ((CD$_3$)$_2$SO, rotamers), 9.81, 9.41 (1H, 2br s), 7.82-7.60 (3H, m), 4.04 (1H, d, J=9.3 Hz), 3.50-3.02 (2H, m), 2.87-2.60 (1H, m), 2.41 (3H, d, J=4.5 Hz), 1.39-0.93 6H, m), 0.75 (9H, s) and 0.67 (3H, t, J=5.7 Hz). $^{13}$C-NMR: δ ((CD$_3$)$_2$SO), 172.5, 170.2, 157.5, 59.9, 42.8, 33.3, 29.0, 28.4, 28.2, 26.4, 24.8, 21.7 and 13.3. IR (KBr disc), ν$_{max}$ 3309, 2959, 2873, 1646 and 1540 cm$^{-1}$.

2-[(Benzyloxy-formyl-amino)-methyl]-hexanoic acid-(2,2-dimethyl-1-methylcarbamoyl-propyl)-amide (diastereoisomer B) (1.0 g, 2.5 mmol) was similarly deprotected to give diastereoisomer B of the title compound (740 mg, 97%). $^1$H-NMR: δ ((CD$_3$)$_2$SO, rotamers), 9.75, 9.30 (1H, 2br s), 7.81-7.42 (3H, m), 4.04 (1H, d, J=9.5 Hz), 3.53-3.02 (2H, m), 2.80-2.55 (1H, m), 2.41 (3H, d, J=4.5 Hz), 1.33-0.82 (6H, m), 0.72 (9H, s) and 0.67 (3H, t, J=6.7 Hz). $^{13}$C-NMR: δ ((CD$_3$)$_2$SO), 172.6, 170.4, 161.7, 157.0, 59.8, 34.0, 29.4, 28.6, 26.7, 25.2, 22.1 and 14.1. IR (KBr disc), ν$_{max}$ 3312, 2959, 1640,1541, 1369 and 1240 cm$^{-1}$.

EXAMPLE 2

2R (or S)-[(Formyl-hydroxy-amino)-methyl]-hexanoic acid-(2,2-dimethyl-1S-tert-butyl-carbamoyl-propyl)-amide

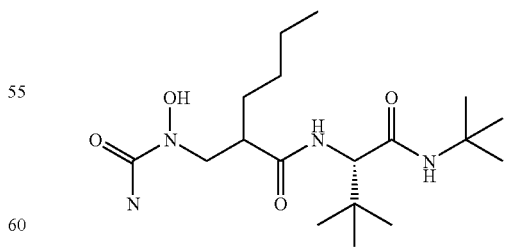

The title compounds were prepared by analogy with Example 1, using the L-tert-leucine-N-tert-butylamide in place of L-tert-leucine-N-methylamide in Step E. The diastereoisomers were not separable by flash chromatography (silica gel, ethyl acetate) at Step E and were converted to a mixture of the desired N-formyl hydroxylamine derivatives by hydrogenolysis. White solid. $^{13}$C-NMR: δ ((CD$_3$)$_2$SO), 172.8, 172.5, 170.1, 169.6, 161.6, 156.9, 59.9, 59.7, 51.9, 51.7, 50.2, 49.6, 48.3, 43.2, 43.1, 42.7, 34.2, 34.0, 29.6, 29.3, 29.2, 28.8, 28.6, 26.7, 22.2, 22.1, 20.3 and 13.9. IR (KBr), ν$_{max}$ 3311, 2964, 1639, 1548, 1456, 1394, 1364 and 1226 cm$^{-1}$.

EXAMPLE 3

2R (or S)-[(Formyl-hydroxy-amino)-methyl]-hexanoic acid (1S-methyl-2-morpholin-4-yl-2-oxo-ethyl)-amide

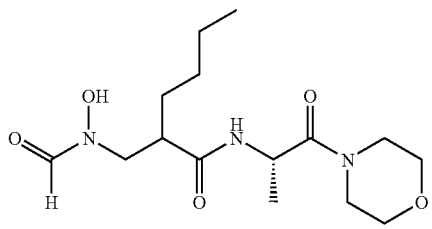

A solution of 2RS-[(benzyloxy-formyl-amino)-methyl]-hexanoic acid pentafluoro-phenyl ester (Example 1, Step D) (445 mg, 1 mmol) in DMF (5 ml) was added to L alanine-N-morpholinoamide (158 mg, 1 mmol) in a boiling tube and stirred at 35° C. overnight. DMF was removed in vacuo and the residue was redissolved in dichloromethane (2 ml) and passed through a purification cartridge (Isolute-NH$_2$), eluting with dichloromethane (4 ml) in order to remove pentafluorophenol. Dichloromethane was removed under reduced pressure and the residue was redissolved in formic acid (2 ml) and ethyl acetate (2 ml). The solution was then treated with 10% palladium on charcoal (200 mg) and stirred at room temperature for 2 hours. Catalyst was removed by filtration through celite, washing well with methanol and solvents were removed in vacuo. Compounds were purified by reverse phase HPLC (gradient elution, 10-90% acetonitrile/water). Diastereoisomer A: $^1$H-NMR; δ (CD$_3$OD), 8.03 (0.5H, s), 7.84 (0.5H, s), 4.75 (1H, m), 3.65 (8H, m), 3.39 (1H, m), 3.24 (1H, dd, J=4.0, 13.2 Hz), 2.84 (1H, m), 1.57 (2H, m), 1.34 (7H, m), and 0.92 (3H, m). LRMS: −ve ion 328 [M−H]. Diastereoisomer B: $^1$H-NMR; δ (CD$_3$OD), 3.66 (8H, m), 3.41 (1H, dd, J=9.98, 13.1 Hz), 3.23 (1H, m), 2.90 (0.5H, m), 2.71 (0.5H, m), 1.62 (2H, m), 1.33 (7H, m), and 0.92 (3H, t, J=6.7 Hz). LRMS: −ve ion 328 [M−H].

The compounds of Examples 4 to 12 were prepared by analogy with Example 3 using the appropriate amine component in place of L-alanine-N-morpholinoamide. Where both diastereoisomers were prepared, diastereoisomer A is the faster eluting and more potent against PDF in vitro. In some cases only the faster running diastereoisomer was taken through to the final product.

EXAMPLE 4

2R (or S)-[(Formyl-hydroxy-amino)-methyl]-hexanoic acid (1S-dimethylcarbamoyl-ethyl)-amide

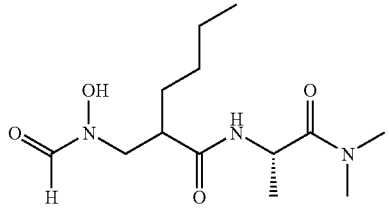

Diastereoisomer A: $^1$H-NMR; δ (CD$_3$OD), 4.72 (1H, m), 3.53 (1H, dd, J=8.9, 13.0 Hz), 3.23 (1H, m), 3.14 (3H, s), 2.95 (3H, s), 2.83 (0.5H, m), 2.74 (0.5H, m), 1.57 (2H, m), 1.33 (7H, m) and 0.92 (3H, m). LRMS; +ve ion 288 [M+H], −ve ion 286 [M−H].

Diastereoisomer B: $^1$H-NMR; δ (CD$_3$OD), 4.74 (1H, m), 3.41 (1H, dd, J=9.9, 13.0 Hz), 3.25 (1H, dd, J=4.0, 13.1 Hz), 3.15 (3H, s), 2.97 (3H, s), 2.89 (0.5H, m), 2.72 (0.5H, m), 1.53 (2H, m), 1.33 (7H, m) and 0.93 (3H, t, J=6.7 Hz). LRMS: +ve ion 310 [M+Na], −ve ion 286 [M−H].

EXAMPLE 5

2R (or S)-[(Formyl-hydroxy-amino)-methyl]-hexanoic acid (1S-hydroxymethyl-3-methyl-butyl)-amide

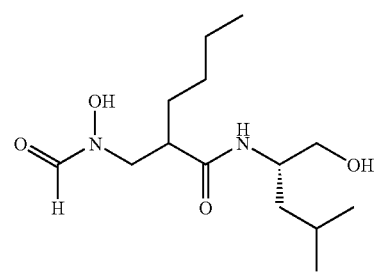

Diastereoisomer A: $^1$H-NMR; δ (CD$_3$OD), 4.07 (1H, m), 3.55 (1H, m), 3.45 (2H, m), 3.20 (1H, m), 2.85 (0.5H, m), 2.80 (0.5H, m), 1.60 (3H, m), 1.35 (6H, m) and 0.93 (9H, m). LRMS: +ve ion 289 [M+H], −ve ion 287 [M−H].

Diastereoisomer B: $^1$H-NMR; δ (CD$_3$OD), 4.07 (1H, m), 3.59 (1H, m), 3.45 (2H, m), 3.24 (1H, m), 2.70 (1H, m), 1.62 (3H, m), 1.35 (6H, m) and 0.93 (9H, m). LRMS: +ve ion 311 [M+Na], 289 [M+H], −ve ion 287 [M−H].

EXAMPLE 6

2R (or S)-[(Formyl-hydroxy-amino)-methyl]-hexanoic acid (1S-hydroxymethyl-2-phenyl-ethyl)-amide

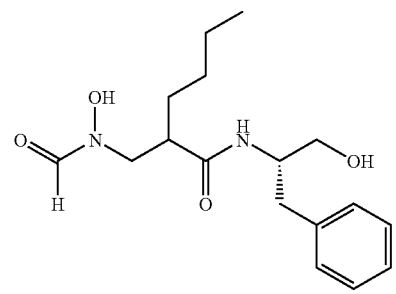

Diastereoisomer A: $^1$H-NMR; δ (CD$_3$OD), 7.24 (5H, m), 4.15 (1H, m), 3.54 (2H, d, J=5.4 Hz), 3.38 (1H, dd, J=7.8, 13.1 Hz), 3.14 (1H, dd, J=4.7, 13.2 Hz), 2.95 (1H, dd, J=7.3, 13.7 Hz), 2.68 (2H, m), 1.58 (2H, m), 1.32 (4H, m), and 0.91 (3H, t, J=6.7 Hz). LRMS: +ve ion 345 [M+Na], 323 [M+H], −ve ion 321 [M−H].

Diastereoisomer B: LRMS: +ve ion 345 [M+Na], 323 [M+H], −ve ion 321 [M−H].

EXAMPLE 7

2R (or S)-[(Formyl-hydroxy-amino)-methyl]-hexanoic acid [2,2-dimethyl-1S-pyridin-2-yl-carbamoyl)-propyl]-amide

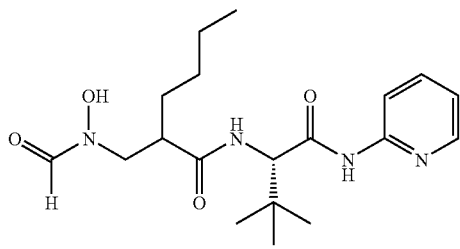

Diastereoisomer A: colourless oil. $^1$H-NMR; δ (CD$_3$OD), 8.34 (1H, m), 8.06 (1H, m), 7.90 (1H, m), 7.33 (1H, m), 4.45 (1H, s), 3.55 (1H, dd, J=8.3, 13.2 Hz), 3.25 (1H, m), 3.05 (1H, m), 1.61 (2H, m), 1.32 (4H, m), 1.11 (9H, s) and 0.85 (3H, m). LRMS: +ve ion 379 [M+H], −ve ion 377 [M−H].

Diastereoisomer B: colourless oil. $^1$H-NMR; δ (CD$_3$OD), 8.33 (1H, m), 8.20 (0.5H, m), 7.93 (1H, m), 7.41 (0.5H, m), 7.28 (1H, m), 4.48 (1H, s), 3.52 (1H, dd, J=8.8, 13.1 Hz), 3.23 (1H, dd, J=3.9, 13.1 Hz), 3.05 (0.5H, m), 2.87 (0.5H, m), 1.62 (2H, m), 1.36 (4H, m), 1.11 (9H, s) and 0.93 (3H, m). LRMS: +ve ion 393 [M+Na], 379 [M+H], −ve ion 377 [M−H].

EXAMPLE 8

2R (or S)-[(Formyl-hydroxy-amino)-methyl]-hexanoic acid (1S-dimethylcarbamoyl-2-methyl-propyl) amide

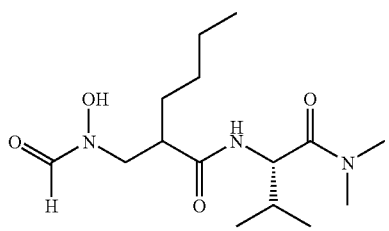

Diastereoisomer A: colourless oil. LRMS: +ve ion 338 [M+Na], −ve ion 319 [M−H].

EXAMPLE 9

2R (or S)-[(Formyl-hydroxy-amino)-methyl]-hexanoic acid (1S-dimethylcarbamoyl-2-phenyl-ethyl) amide

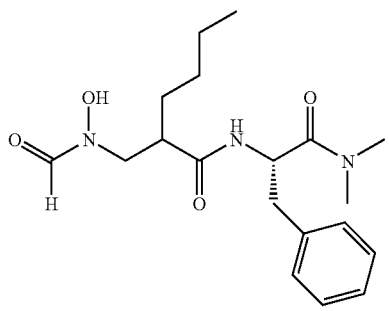

Diastereoisomer A: colourless oil. LRMS: +ve ion 386 [M+Na], −ve ion 362 [M−H]

Diastereoisomer B: colourless oil. LRMS: +ve ion 386 [M+Na], −ve ion 362 [M−H]

EXAMPLE 10

2R (or S)-[(Formyl-hydroxy-amino)-methyl]-hexanoic acid (1S-dimethylcarbamoyl-3-methyl-butyl) amide

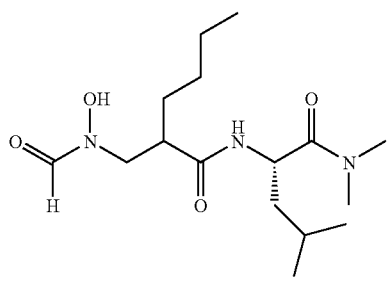

Diastereoisomer A: colourless oil. LRMS: +ve ion 352 [M+Na], −ve ion 328 [M−H].

EXAMPLE 11

2R (or S)-[(Formyl-hydroxy-amino)-methyl]-hexanoic acid [3-methyl-1S-pyrrolidine-1-carbonyl)-butyl]amide

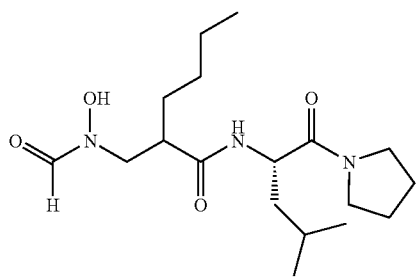

Diastereoisomer A: colourless oil. LRMS: −ve ion 354 [M−H].

EXAMPLE 12

1-{2R (or S)-[(Formyl-hydroxy-amino)-methyl]-hexanoyl}-pyrrolidine-2S-carboxylic acid dimethylamide

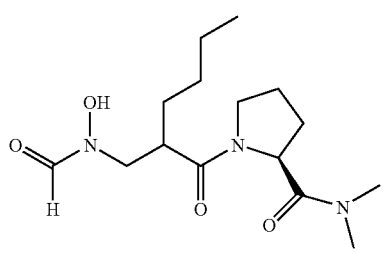

Diastereoisomer A: colourless oil. LRMS: +ve ion 336 [M+Na], −ve ion 312 [M−H].

Diastereoisomer B: colourless oil. LRMS: +ve ion 336 [M+Na], −ve ion 312 [M−H].

EXAMPLE 13

2R (or S)-[(Formyl-hydroxy-amino)-methyl]-hexanoic acid-(1S-dimethylcarbamoyl-2,2-dimethyl-propyl)-amide

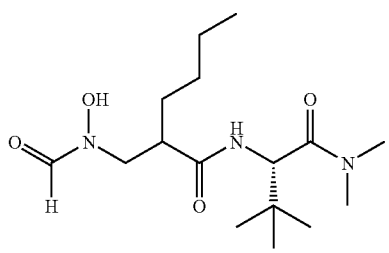

Method I

A synthetic route to the title compound is outlined in Scheme 2 and is described in detail below.

Scheme 2

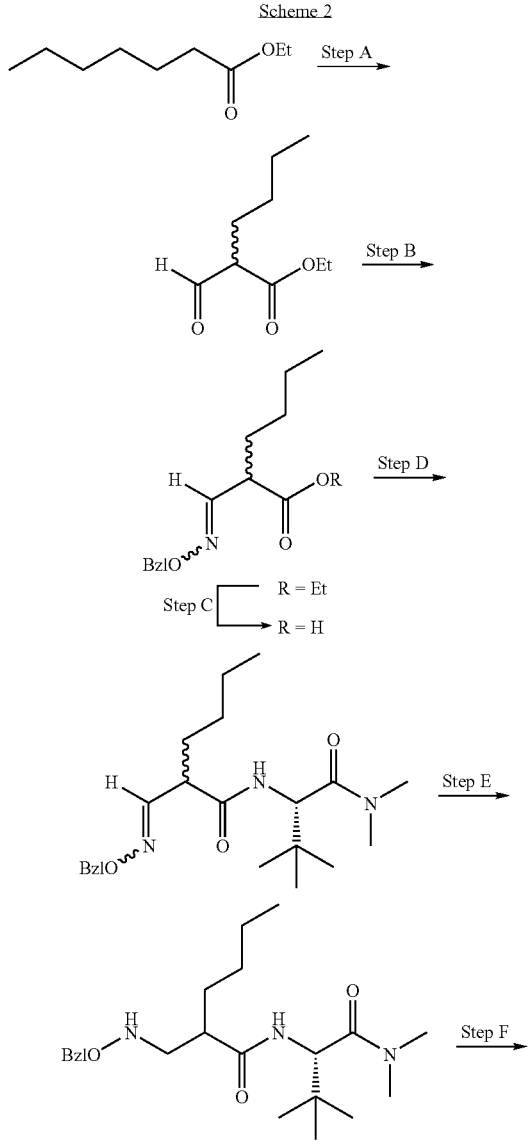

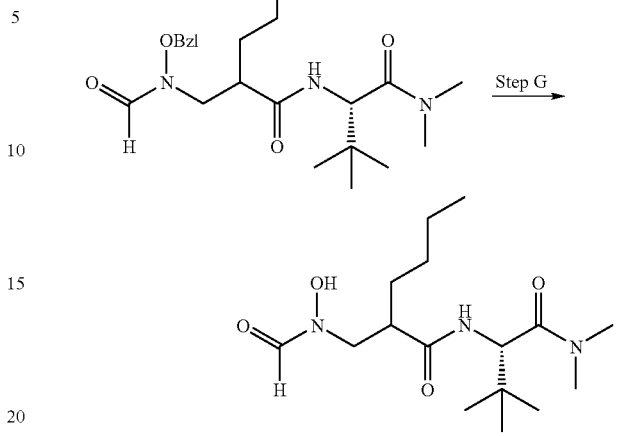

A. HCOOEt, NaOEt;
B. HCl•NHOBzl, NaOAc, aq. EtOH;
C. NaOH, MeOH;
D. H-TleNMe$_2$, EDC, HOAt, DMF;
E. NaCNBH$_3$, AcOH then separate diastereoisomers;
F. HCOBt, THF;
G. H$_2$, Pd/C, MeOH.

Step A: 2RS-Formyl-heptanoic acid ethyl ester

Sodium metal (4.38 g, 0.191 mmol) was cut into small pieces and placed in a two-neck oven-dried round bottom flask under a blanket of argon. Anhydrous diethyl ether (100 ml) was added and the suspension was stirred and cooled to 0° C. The flask was fitted with a reflux condenser before dropwise addition of ethanol (1.03 ml, 17.3 mmol). A mixture of ethyl formate (15.41 g, 0.208 mmol) and ethyl caproate (25 g, 0.173 mmol) was added dropwise via a dropping funnel over a period of about 20 minutes. The resulting orange suspension (sodium metal still visible) was allowed to warm to room temperature and stirred overnight. The resulting thick orange suspension (no sodium metal visible) was cooled to 0° C. and diluted with ice-cold water (100 ml). The mixture was transferred to a separating funnel and the aqueous phase was removed, washed with diethyl ether, cooled to 0° C. and acidified with 1 M hydrochloric acid (200 ml). The emulsion was extracted with ethyl acetate and the organic layer was separated, washed with brine, dried over anhydrous magnesium sulfate and filtered. The filtrate was concentrated under reduced pressure to give a yellow oil containing primarily the title compound (11.09 g), which was used without further purification in Step B.

Step B: 2RS-(Benzyloxyimino-methyl)-heptanoic acid ethyl ester

The crude Claisen product from Step A (11.0 g, 63.9 mmol) was dissolved in ethanol (100 ml) and water (10 ml) and cooled to 0° C. during the addition of sodium acetate (6.2 g, 76.6 mmol) and O-benzyl hydroxylamine hydrochloride (12.23 g, 76.6 mmol). The mixture was allowed to warm to room temperature and stirred overnight. The resulting suspension was filtered and the filtrate was concentrated under reduced pressure. The residual yellow paste was partitioned between ethyl acetate and water. The organic layer was washed with 1 M hydrochloric acid and brine, dried over anhydrous magnesium sulfate, filtered and evaporated to a yellow oil. The desired product was obtained by flash chromatography (silica gel, gradient elution with 10% to 25% ethyl acetate in hexane. Yield 9.19 g (52%). $^1$H-NMR: δ (CDCl$_3$, mixture of syn- and anti-isomers), 7.46 (0.6H, d, J=8.0 Hz), 7.38-7.28 (5H, m), 6.79 (0.4H, d, J=7.1 Hz), 5.11 (0.8H, s), 5.08 (1.2H, s), 4.16 (1.2H, q, J=7.0 Hz), 4.13 (0.6H, q, J=7.0 Hz), 3.91 (0.4H, q, J=7.2 Hz), 3.21 (0.6H, td, J=8.0 and 6.1 Hz), 1.90-1.48 (2H, m), 1.37-1.20 (7H, m), 0.87 (3H, t, J=7.0 Hz).

Step C: 2RS-(Benzyloxyimino-methyl)-heptanoic acid

2RS-(Benzyloxyimino-methyl)-heptanoic acid ethyl ester (7.0 g, 25.24 mmol) was dissolved in methanol (125 ml) and the solution was cooled to 0° C. 1 M Sodium hydroxide (26 ml, 26 mmol) was added in portions over 2 minutes to give a pale yellow emulsion. Additional methanol was added until a clear solution was obtained. The solution was allowed to stir for 90 minutes at 0° C. then for 5 hours at room temperature whereupon TLC analysis suggested that all of the starting material had been consumed. The solvent was removed under reduced pressure and the residue was partitioned between water and ethyl acetate. The aqueous layer was cooled to 0° C. and acidified with 1 M hydrochloric acid. The emulsion thus formed was extracted twice with ethyl acetate. The combined organic extracts were washed with brine, dried over anhydrous magnesium sulfate and filtered. The filtrate was concentrated under reduced pressure to provide the title compound as a yellow oil (5.15 g, 82%) which was used without further purification in Step D. $^1$H-NMR: δ (CDCl$_3$, mixture of syn- and anti-isomers), 8.00 (1H, br s), 7.46 (0.6H, d, J=7.9 Hz), 7.36-7.24 (5H, m), 6.80 (0.4H, d, J=7.0 Hz), 5.13 (0.8H, s), 5.09 (1.2H, s), 3.94 (0.4H, q, J=7.1 Hz), 3.27 (0.6H, td, J=6.4 and 8.0 Hz), 1.94-1.58 (2H, m), 1.48-1.24 (4H, m) and 0.94-0.84 (3H, m).

Step D: 2RS-(Benzyloxyimino-methyl)-heptanoic acid (1S-dimethylcarbamoyl-2,2-dimethyl-propyl)amide 2-(Benzyloxyimino-methyl)-heptanoic acid (5.16 g, 20.7 mmol), tert-leucine N,N-dimethylamide (3.60 g, 22.77 mmol) and EDC (4.76 g, 24.84 mmol) were stirred together in DMF (75 ml) and cooled to 0° C. HOAt (250 mg, cat.) was added and the bright yellow mixture was allowed to warm to room temperature and stirred overnight. The solvent was removed under reduced pressure and the residual oil was partitioned between ethyl acetate and 1M hydrochloric acid. The organic layer was washed with brine, dried over anhydrous magnesium sulfate, filtered and concentrated to dryness under reduced pressure. The title compound was obtained as a colourless oil by flash chromatography (silica gel, gradient elution with 33% to 66% ethyl acetate in hexane). Yield 6.84 g (85%). $^1$H-NMR: δ (CDCl$_3$, mixture of syn- and anti-isomers), 7.45 (0.6H, 2d), 7.40-7.26 (5H, m), 6.72 (0.4H, 2d), 6.58 (1H, m), 5.20-4.69 (3H, m), 3.82 (0.4H, m), 3.16-3.10 (3H, m), 3.05 (0.6H, m), 2.99-2.92 (3H, m), 1.90-1.54 (2H, m), 1.39-1.17 (4H, m), 0.97 (2.7H, s), 0.96 (1.8H, s), 0.94 (2.7H, s), 0.92 (1.8H, s) and 0.92-0.82 (3H, m).

Step E: 2R (or S)-(Benzyloxyamino-methyl)-heptanoic acid (1S-dimethylcarbamoyl-2,2-dimethyl-propyl)amide To a solution of 2RS-(benzyloxyimino-methyl)-heptanoic acid (1S-dimethyl-carbamoyl-2,2-dimethyl-propyl)amide (5.0 g, 12.84 mmol) in acetic acid (40 ml) was added sodium cyanoborohydride (2.02 g, 32.0 mmol) in one portion. Over the course of 1 hour the reagent dissolved slowly with mild effervesence to give a colourless solution, which was left to stir overnight. The solvent was removed by evaporation under reduced pressure and azeotroping with toluene. The remaining oil was partitioned between diethyl ether and 1 M sodium carbonate (CARE!-some gas evolved). The organic layer was washed with brine (70 ml), washed with brine, dried over anhydrous magnesium sulfate, filtered and concentrated to dryness under reduced pressure. The two diastereoisomers of title compound were purified and separated by flash chromatography (silica gel, gradient elution with 50% to 100% ethyl acetate in hexane).

Diastereoisomer A (faster eluting): colourless oil (2.27 g, 45%). $^1$H-NMR: δ (CDCl$_3$), 7.43-7.28 (5H, m), 6.76 (1H, br d, J=9.4 Hz), 5.69 (1H, br s), 4.93 (1H, d, J=9.4 Hz), 4.72 (2H, s), 3.15 (3H, s), 3.18-3.00 (2H, m), 2.96 (3H, s), 2.49 (1H, m), 1.66-1.49 (2H, m), 1.46-1.19 (4H, m), 0.99 (9H, s) and 0.86 (3H, t, J=6.8 Hz).

Diastereoisomer B (slower eluting): colourless oil (1.44 g, 46%). $^1$H-NMR: δ (CDCl$_3$), 7.40-7.27 (5H, m), 6.70 (1H, br d, J=9.0 Hz), 5.99 (1H, br s), 4.85 (1H, d, J=9.0 Hz), 4.71 (2H, d, J=1.6 Hz), 3.16 (3H, s), 3.06-2.97 (2H, m), 2.95 (3H, s), 2.57 (1H, m), 1.74-1.21 (6H, m), 1.00 (9H, s) and 0.88 (3H, br t, J=6.7 Hz).

Step F: 2R (or S)-[(Benzyloxy-formyl-amino)-methyl]-heptanoic acid (1S-dimethylcarbamoyl-2,2-dimethyl-propyl)amide 2-(Benzyloxyamino-methyl)-heptanoic acid (1S-dimethylcarbamoyl-2,2-dimethyl-propyl)amide (diastereoisomer A) (2.02 g, 5.13 mmol) was dissolved in anhydrous THF (50 ml) and placed under a blanket of argon. N-formyl-benzotriazole (A. R. Katritzky et al., *Synthesis* 1995, 503) (0.83 g, 5.65 mmol) was added and the mixture was allowed to stir at room temperature for 4 hours. The solvent was evaporated under reduced pressure and the residual oil was partitioned between dichloromethane and 1 M sodium hydroxide. The organic layer was washed with more sodium hydroxide and brine, dried over anhydrous magnesium sulfate, filtered and concentrated to dryness under reduced pressure. The title compound was obtained as a white crystalline solid by flash chromatography (silica gel, elution with 33% ethyl acetate in hexane). Yield 1.60 g (74%). $^1$H-NMR: δ (CDCl$_3$, rotamers), 8.00 (1H, br m), 7.47-7.29 (5H, m), 6.25 (1H, br d, J=9.3 Hz), 5.08-4.74 (2H, br m), 4.87 (1H, d, J=9.4 Hz), 3.89-3.52 (2H, br m), 3.13 (3H, s), 2.94 (3H, s), 2.54 (1H, m), 1.67-1.11 (6H, m), 0.95 (9H, s) and 0.85 (3H, br t, J=6.9 Hz).

2-(Benzyloxyamino-methyl)-heptanoic acid (1S-dimethylcarbamoyl-2,2-dimethyl-propyl)amide (diastereoisomer B) was similarly prepared from the the slower eluting diastereoisomer in Step E. Yield 0.38 g (41%). $^1$H-NMR: δ (CDCl$_3$, rotamers), 8.00 (1H, br m), 7.47-7.28 (5H, br m), 6.29 (1H, br d, J=9.3 Hz), 5.01-4.63 (2H, br m), 4.88 (1H, d, J=9.3 Hz), 3.82-3.51 (1.5H, br m), 3.20-2.78 (6.5H, br m), 2.50 (1H, br m), 1.76-1.17 (6H, br m), 0.97 (9H, s) and 0.85 (3H, br t, J=6.7 Hz).

Step G: 2R (or S)-[(Formyl-hydroxy-amino)-methyl]-hexanoic acid-(1S-dimethyl carbamoyl-2,2-dimethyl-propyl)-amide 2-[(Benzyloxy-formyl-amino)-methyl]-heptanoic acid (1S-dimethylcarbamoyl-2,2-dimethyl-propyl)amide (diastereoisomer A) (1.43 g, 3.41 mmol) was dissolved in methanol (50 ml) and placed under a blanket of argon. A suspension of 10% palladium on charcoal (100 mg, cat.) in ethyl acetate (2 ml) was added and the mixture was stirred vigorously while hydrogen gas was bubbled through the solution. After 10 minutes the mixture was placed under an atmosphere of hydrogen and left to stir for 3 hours, whereupon TLC analysis indicated that all of the starting material had been consumed. The system was purged with argon and the catalyst was removed by filtration. The filtrate was concentrated under reduced pressure to provide the title compound as a colourless hygroscopic foam (1.11 g, 99%). $^1$H-NMR: δ (CDCl$_3$, rotamers), 8.41 (0.35H, s), 7.83 (0.65H, br s), 6.80 (0.35H, br d, J=8.9 Hz), 6.62 (0.65H, br d, J=9.4 Hz), 4.91 (0.65H, br d, J=9.4 Hz), 4.88 (0.35H, br d, J=8.9 Hz), 4.04 (1H, dd, J=14.7 and 7.4 Hz), 3.82 (0.65, dd, J=14.0 and 9.7 Hz), 3.56 (0.35H, dd, J=14.7 and 3.3 Hz), 3.48 (0.65H, dd, J=14.0 and 4.0 Hz), 3.16 (1.05H, s), 3.15 (1.95H, s), 2.98 (1.05H, s), 2.96 (1.95H, s), 2.90-2.74 (0.65H, br m), 2.74-2.61 (0.35H, br m) 1.73-1.17 (6H, br m), 0.99 (3.15H, s). 0.95 (5.85H, s) and 0.87 (3H, br t, J=6.7 Hz). $^{13}$C-NMR; δ (CDCl$_3$), 174.6, 171.2, 162.2, 157.2, 60.1, 54.5, 54.3, 52.3, 48.4, 44.8, 44.3, 35.6, 35.4, 29.6, 29.0, 26.3, 20.8, 20.2, 14.0 and 13.7. LRMS: +ve ion 352 (M+Na), −ve ion 328 (M−H).

2-[(Formyl-hydroxy-amino)-methyl]-hexanoic acid-(1S-dimethylcarbamoyl-2,2-dimethyl-propyl)-amide (diastereoisomer B) was similarly prepared from diastereoisomer B in Step E $^1$H-NMR; δ (CDCl$_3$, rotamers), 9.37 (0.5H, s), 8.40 (0.5H, s), 7.75 (0.5H, br s), 6.62 (0.5H, br s), 6.41 (0.5H, br d, J=7.1 Hz), 4.87 (0.5H, br d, J=6.6 Hz), 4.66 (0.5H, br d, J=7.6 Hz), 3.84-3.39 (2H, m), 3.21 (1.5H, br s), 3.14 (1.5H, br s), 2.98 (3H, br s), 2.91-2.54 (1H, m), 1.79-1.23 (6H, m) and 1.08-0.83 (12H, m). $^{13}$C-NMR; δ (CDCl$_3$, rotamers), 174.9, 173.3, 56.3, 54.8, 51.6, 50.3, 45.5, 45.1, 38.6, 38.4, 36.2, 36.0, 35.3, 34.4, 29.5, 29.4, 29.3, 29.2, 26.6, 26.5, 22.6, 22.5 and 13.9. LRMS: +ve ion 352 [M+Na], −ve ion 328 [M−H].

Method II

An alternative asymmetric synthetic route to the compound of Example 13 is outlined in Scheme 3 and is described in detail below.

Scheme 3

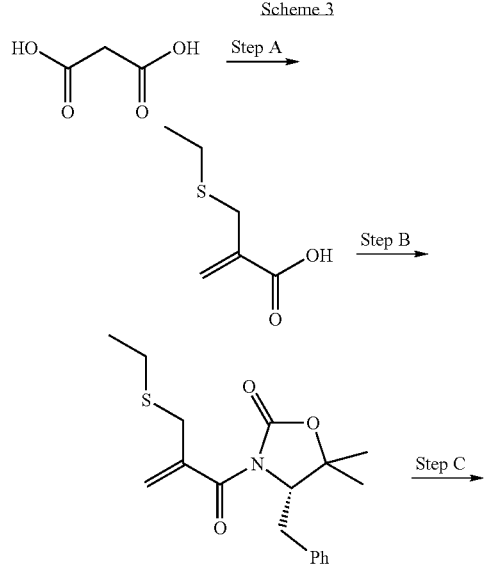

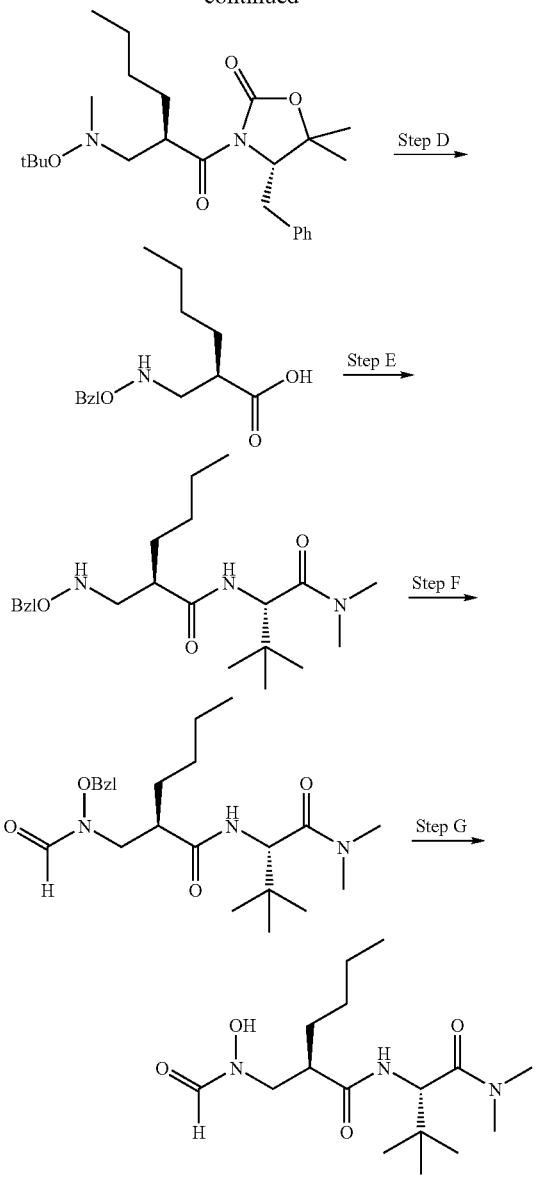

Reagents and conditions:
A. piperidine, HCHO, EtOH, 80° C., o/n;
B. $^t$BuCOCl, Et$_3$N then 3-lithio-4-benzyl-5,5-dimethyl-oxazolidin-2-one;
C. H$_2$NOBzl, room temp., o/n then pTsOH, EtOAc;
D. LiOH, aq THF, 0° C.;
E. H-TleNMe$_2$, HOBt, EDC, DMF;
F. HCOBt, THF;
G. H$_2$, Pd/C, EtOH.

Step A: 2-Butyl acrylic acid

To a solution of n-butylmalonic acid (17.2 g, 107 mmol) in ethanol (200 ml) was added piperidine (12.76 ml, 129 mmol) and 37% aq. formaldehyde (40.3 ml, 538 mmol). The solution was heated to 80° C. during which time a precipitate appeared and then gradually redissolved over 1 hour. The reaction mixture was stirred at 80° C. overnight then cooled to room temperature. The solvents were removed under reduced pressure and the residue was dissolved in ethyl acetate (200 ml), washed successively with 1 M hydrochloric acid and brine, dried over anhydrous magnesium sulfate and filtered. The filtrate was concentrated to give the title compound as a clear oil (13.37 g, 97%). $^1$H-NMR; δ (CDCl$_3$), 6.29 (1H, s), 5.65 (1H, s), 2.34-2.28 (2H, m), 1.54-1.26 (4H, m) and 0.94 (3H, t, J=7.1 Hz).

Step B: 4S-Benzyl-3-(2-butyl-acryloyl)-5,5-dimethyl-oxazolidin-2-one

2-Butyl acrylic acid (21.5 g, 168 mmol) was dissolved in dry THF (500 ml) and cooled to −78° C. under a blanket of argon. Triethylamine (30 ml, 218 mmol) and pivaloyl chloride (21 ml, 168 mmol) were added at such a rate that the temperature remained below −60° C. The mixture was stirred at −78° C. for 30 minutes, warmed to room temperature for 2 hours and finally cooled back to −78° C.

In a separate flask, 4S-benzyl-5,5-dimethyl-oxazolidin-2-one was dissolved in dry THF (500 ml) and cooled to −78° C. under a blanket of argon. n-Butyllithium (2.4 M solution in hexanes, 83 ml, 200 mmol) was added slowly and the mixture was stirred for 30 minutes at room temperature. The resulting anion was transferred via a cannula into the original reaction vessel. The mixture was allowed to warm to room temperature and was stirred overnight at room temperature. The reaction was quenched with 1 M potassium hydrogen carbonate (200 ml) and the solvents were removed under reduced pressure. The residue was partitioned between ethyl acetate and water. The organic layer was washed with brine, dried over anhydrous magnesium sulphate, filtered and concentrated under reduced pressure to give an orange oil. TLC analysis revealed the presence of unreacted chiral auxiliary in addition to the required product. A portion of the material (30 g) was dissolved in dichloromethane and flushed though a silica pad to give pure title compound as a yellow oil (25.3 9). $^1$H-NMR; δ (CDCl$_3$), 7.31-7.19 (5H, m), 5.41 (2H, s), 4.51 (1H, dd, J=9.7, 4.2 Hz), 3.32 (1H, dd, J=14.2, 4.2 Hz), 2.82 (1H, dd, J=14.2, 9.7 Hz), 2.40-2.34 (2H, m), 1.48-1.32 (4H, m), 1.43 (3H, s), 1.27 (3H, s) and 0.91 (3H, t, J=7.1 Hz. Some chiral auxiliary was recovered by flushing the silica pad with methanol.

Step C: 4S-Benzyl-3-[2-(benzyloxyamino-methyl)-hexanoyl]-5,5-dimethyl-oxazolidin-2-one (p-toluenesulfonic acid salt)

4S-Benzyl-3-(2-butyl-acryloyl)-5,5-dimethyl-oxazolidin-2-one (19.8 g, 62.8 mmol) was mixed with O-benzylhydroxylamine (15.4 g, 126 mmol) and stirred overnight at room temperature. The mixture was dissolved in ethyl acetate and the solution was washed with 1 M hydrochloric acid, 1 M sodium carbonate and brine, dried over anhydrous magnesium sulfate and filtered. The filtrate was concentrated under reduced pressure to a pale yellow oil (25.3 g) which was shown by NMR and HPLC analysis to contain 4S-Benzyl-3-[2-(benzyloxyamino-methyl)-hexanoyl]-5,5-dimethyl-oxazolidin-2-one (ca. 82% d.e.) along with a trace of starting material. The product was combined with another batch (26.9 g, 76% d.e.) and dissolved in ethyl acetate (200 ml). p-Toluenesulfonic acid (22.7 g, 119 mmol) was added and the mixture was cooled to 0° C. The title compound was obtained as a white crystalline solid by seeding and scratching. Yield: 25.2 g, (34%, single diastereoisomer). A second crop (14.7 g, 20%, single diastereoisomer) was also obtained. $^1$H-NMR; δ (CDCl$_3$), 7.89 (2H, d, J=8.2 Hz), 7.37-7.12 (10H, m), 7.02 (2H, d, J=6.9 Hz), 5.28-5.19 (2H, m), 4.55 (1H, m), 4.23 (1H, m), 3.93 (1H, m), 3.58 (1H, m), 2.58 (1H, m), 2.35 (3H, s), 1.67-1.51 (2H, m), 1.29-1.16 (4H, m), 1.25 (3H, s), 1.11 (3H, s) and 0.80-0.75 (3H, m).

Step D: 2R-Benzyloxyamino-methyl)-hexanoic acid

4S-Benzyl-3-[2R-(benzyloxyamino-methyl)-hexanoyl]-5,5-dimethyl-oxazolidin-2-one p-toluenesulfonic acid salt (25.2 g, 40.2 mmol) was partitioned between ethyl acetate and 1 M sodium carbonate. The organic phase was dried over anhydrous magnesium sulfate, filtered and evaporated under reduced pressure. The residual oil was dissolved in THF (150 ml) and water (50 ml) and cooled to 0° C. and treated with lithium hydroxide (1.86 g, 44.2 mmol). The solution was stirred for 30 minutes at 0° C., then overnight at room temperature. The reaction was acidified to pH4 with 1 M citric acid and the solvents were removed. The residue was partitioned between dichloromethane and 1 M sodium carbonate. The basic aqueous layer was acidified to pH4 with 1 M citric acid and extracted three times with ethyl acetate. The combined organic layers were dried over anhydrous magnesium sulfate, filtered and concentrated to provide the title compound as a colourless oil (7.4 g, 73%). $^1$H-NMR; δ (CDCl$_3$), 8.42 (2H, br s), 7.34-7.25 (5H, m), 4.76-4.66 (2H, m), 3.20-3.01 (2H, m), 2.73 (1H, m), 1.70-1.44 (2H, m), 1.34-1.22 (4H, m) and 0.92-0.86 (3H, m).

Step E: 2R-(Benzyloxyamino-methyl)-hexanoic acid (1S-dimethylcarbamoyl-2,2-dimethyl-1-propyl) amide 2R-Benzyloxyamino-methyl)-hexanoic acid (7.98 g, 31.8 mmol) was dissolved in DMF (150 ml) and the solution was cooled to 0° C. EDC (6.1 g, 31.8 mmol) and HOBt (430 mg, 3.2 mmol) were added and the mixture was stirred for 15 minutes. tert-Leucine-N,N-dimethylamide (5.53 g, 34 mmol) was added and the reaction was allowed to warm to room temperature and was stirred overnight. The solvent was removed under reduced pressure and the residue was dissolved in ethyl acetate, washed successively with 1 M hydrochloric acid, saturated sodium hydrogen carbonate and brine, dried and filtered. The solvent was removed to leave the title compound as a yellow oil (8.7 g, 69%) which was used in Step F without further purification. $^1$H-NMR; δ (CDCl$_3$), 7.35-7.28 (5H, m), 6.77 (1H, br d, J=9.2 Hz), 5.69 (1H, br s), 4.93 (1H, d, J=9.4 Hz), 4.72 (2H, s), 3.15 (3H, s), 3.10-3.00 (2H, m), 2.95 (3H, s), 2.49 (1H, m), 1.64-1.21 (6H, m), 0.99 (9H, s) and 0.86 (3H, t, J=6.8 Hz).

Step F: 2R-[(Benzyloxy-formyl-amino)-methyl]-hexanoic acid (1S-dimethyl-carbamoyl-2,2-dimethyl-1-propyl)amide 2R-(Benzyloxyamino-methyl)-hexanoic acid (1S-dimethylcarbamoyl-2,2-dimethyl-1-propyl)amide (7.8 g, 19.9 mmol) was dissolved in dry THF (100 ml) and treated with 1-formyl-benzotriazole (3.08 g, 21.0 mmol). The reaction was stirred overnight at room temperature. The solvent was removed under reduced pressure and the residue was dissolved in ethyl acetate, washed with 2 M sodium hydroxide solution and brine. The organic layer was dried over anhydrous magnesium sulfate, filtered and concentrated to dryness under reduced pressure. The product was crystallised from ether-hexane (4.83 g, 57% in two crops). $^1$H-NMR; δ (CDCl$_3$, rotamers), 8.12 (0.6H, br s), 7.89 (0.4H, br s), 7.37 (5H, s), 6.25 (1H, d, J=9.3 Hz), 4.96 (0.6H, br s), 4.86 (1H, d, J=9.4 Hz), 4.80 (0.4H, br s), 3.74 (2H, br s), 3.13 (3H, s), 2.94 (3H, s), 2.53 (1H, m), 1.38-1.21 (6H, m), 0.95 (9H, s) and 0.85 (3H, t, J=6.9 Hz). Note: A small sample was crytallised from ether-hexane to provide crystals suitable for X-ray crystallography. The stereochemistry was proven to be as stated herein.

Step G: 2R-[(Formyl-hydroxy-amino)-methyl]-hexanoic acid (1S-dimethylcarbamoyl-2,2-dimethyl-1-propyl)amide 2R-[(Benzyloxy-formyl-amino)-methyl]-hexanoic acid (1S-dimethylcarbamoyl-2,2-dimethyl-1-propyl)amide (4.72 g, 11.3 mmol) was dissolved in ethanol (80 ml) and placed under a blanket of argon. A suspension of 10% palladium on charcoal (940 mg) in ethyl acetate (2 ml) was added and the mixture was stirred vigorously as hydrogen gas was bubbled through the system. After 30 minutes the suspension was placed under a balloon of hydrogen and stirred overnight at room temperature. The flask was purged with argon before removing the catalyst by filtration. The filtrate was concentrated under reduced pressure to provide the title compound as a colourless foam which crystallised on standing (3.65 g, 98%). $^1$H-NMR; δ (CDCl$_3$, rotamers), 9.32 (0.4H, br s), 8.41 (0.4H, s), 7.88 (0.6H, br s), 7.27 (0.6H, s), 6.75 (0.4H, br d, J=8.8 Hz), 6.58 (0.6H, br d, J=9.3 Hz), 4.89 (1H, m), 4.04 (0.4H, m), 3.82 (0.6H, m), 3.53 (1H, m), 3.16 (1.2H, s), 3.15 (1.8H, s), 2.98 (1.2H, s), 2.96 (1.8H, s), 2.79 (0.6, m), 2.65 (0.4H, m), 1.78-1.58 (6H, m), 0.99 (3.6H, s), 0.95 (5.4H, s) and 0.87, 3H, t, J=6.7 Hz). $^{13}$C-NMR; δ (CDCl$_3$, rotamers), 175.8, 173.3, 172.0, 55.4, 54.9, 52.2, 48.8, 46.3, 38.9, 38.8, 36.3, 36.1, 30.3, 30.2, 29.7, 26.9, 23.0 and 14.3. LRMS: +ve ion 352 [M+Na], −ve ion 328 [M−H].

The compounds of Examples 14 to 27 were prepared by analogy with Example 13, Method I, substituting the appropriate ester for ethyl caproate in Step A. Where both diastereoisomers were prepared, diastereoisomer A is the faster eluting and usually the more potent against PDF in vitro. In some cases only the faster running diastereoisomer (Step E) was taken through to the final product.

EXAMPLE 14

2R (or S)-[(Formyl-hydroxy-amino)-methyl]-3-cyclopentyl-propionic acid (1S-dimethyl-carbamoyl-2,2-dimethyl-propyl)-amide

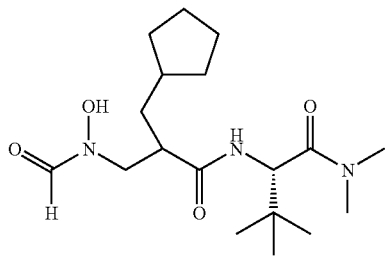

Diastereoisomer A. Colourless glass. $^1$H-NMR; δ (CDCl$_3$, rotamers), 9.33 (0.4H, br s), 8.94 (0.6H, br s), 8.40 (0.4H, s), 7.82 (0.6H, s), 6.82 (0.4H, br d, J=8.6 Hz), 6.62 (0.6H, br d, J=9.3 Hz), 4.90 (1H, m), 4.06 (0.4H, br dd, J=14.7, 7.3 Hz), 3.81 (0.6H, br dd, J=14.0, 9.7 Hz), 3.50 (1H, m), 3.16 (1.2H, s), 3.14 (1.8H, s), 2.97 (1.2H, s), 2.95 (1.8H, s), 2.80 (1H, m), 1.87-1.32 (9H, m), 1.16-0.95 (2H, m), 0.99 (3.6H, s), and 0.95 (5.4H, s). $^{13}$C-NMR; δ (CDCl$_3$, rotamers), 172.9, 171.3, 55.0, 54.5, 52.0, 48.6, 45.4, 44.2, 38.5, 38.4, 37.9, 37.6, 36.4, 36.3, 35.8, 35.6, 35.5, 32.7, 32.6, 26.5, 26.4 and 25.1. LRMS: +ve ion 378 [M+Na], −ve ion 354 [M−H].

Diastereoisomer B. Colourless glass. $^1$H-NMR; δ (CDCl$_3$, rotamers), 9.30 (0.6H, br s), 8.41 (0.6H, s), 7.75 (0.4H, s), 6.52 (0.4H, br d, J=8.7 Hz), 6.41 (0.6H, br d, J=7.3 Hz), 4.85 (0.4H, br d, J=9.5 Hz), 4.63 (0.6H, br d, J=7.5 Hz), 3.85-3.40 (2H, m), 3.25-2.95 (6H, 3br s), 2.78 (1H, 2br m), 1.90-1.40 (8H, m), 1.30 (1H, m), 1.20-1.00 (2H, m) and 1.05-0.95 (9H, 2s). $^{13}$C-NMR; δ (CDCl$_3$, rotamers), 174.9, 173.3, 172.8, 56.5, 54.7, 51.5, 50.5, 44.7, 44.6, 38.6, 38.4, 38.0, 37.8, 36.2, 36.0, 35.7, 35.5, 35.3, 34.3, 33.0, 32.9, 32.4, 32.3, 30.9, 26.6, 26.5, 25.1, 25.0 and 24.9. LRMS: +ve ion 378 [M+Na], −ve ion 354 [M−H].

EXAMPLE 15

2R (or S)-[(Formyl-hydroxy-amino)-methyl]-heptanoic acid-(1S-dimethylcarbamoyl-2,2-dimethyl-propyl)-amide

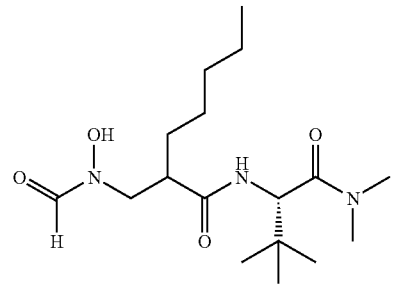

Diastereoisomer A. Dark orange oil. $^1$H-NMR; δ (CDCl$_3$, rotamers), 8.32 (0.33H, s), 7.76 (0.67H, br s), 6.78 (0.33H, br d, J=9.1 Hz), 6.68 (0.67H, br d, J=9.1 Hz), 4.87-4.79 (1H, m), 3.96 (0.33H, br dd, J=14.6, 7.6 Hz), 3.74 (0.67H, br dd, J=13.9, 9.7 Hz), 3.51-3.36 (1H, m), 3.09 (1H, s), 3.08 (2H, s), 2.90 (1H, s), 2.89 (2H, s), 2.86-2.55 (1H, m), 1.53-1.19 (8H, br m), 0.92 (3H, s), 0.88 (6H, s) and 0.79 (3H, m). $^{13}$C-NMR; δ (CDCl$_3$, rotamers), 174.3, 172.0, 170.5, 170.4, 54.0, 53.5, 53.4, 50.8, 49.7, 47.4, 44.9, 43.8, 37.5, 37.4, 34.8, 34.7, 34.6, 30.6, 29.2, 29.1, 25.8, 25.5, 21.4 and 12.9. LRMS: +ve ion 344 M+H], −ve ion 342 [M−H].

Diastereoisomer B. Dark orange oil. $^1$H-NMR; δ (CDCl$_3$, rotamers), 8.36 (0.5H, s), 7.74 (0.5H, s), 6.69 (0.5H, br s), 6.57 (0.5H, br d, J=7.6 Hz), 4.89 (0.5H, br s), 4.70 (0.5H, d, J=7.8 Hz), 3.76-3.40 (2H, m), 3.21 (1.5H, s), 3.16 (1.5H, s), 2.98 (3H, s), 2.81 (1H, br s), 2.72-2.60 (1H, m), 1.67 (2H, br s), 1.42-1.22 (6H, m), 1.02 (4.5H, s), 0.99 (4.5H, s), 0.90 (1.5H, s) and 0.87 (1.5H, s). $^{13}$C-NMR; δ (CDCl$_3$, rotamers), 175.2, 173.8, 173.1, 56.5, 55.1, 52.3, 51.1, 50.6, 45.8, 45.5, 39.0, 38.9, 36.6, 36.3, 35.6, 34.9, 32.1, 32.0, 30.1, 29.9, 27.4, 27.4, 27.0, 26.9, 22.9 and 14.3. LRMS: +ve ion 344 [M+H], −ve ion 342 [M−H].

EXAMPLE 16

2R (or S)-[(Formyl-hydroxy-amino)-methyl]-pentanoic acid-(1S-dimethylcarbamoyl-2,2-dimethyl-propyl)-amide

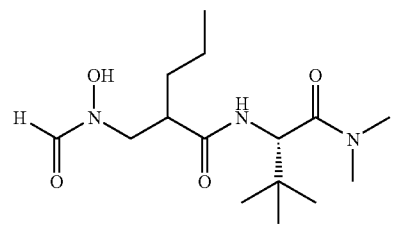

Diastereoisomer A. White hygroscopic foam. $^1$H-NMR; δ (CDCl$_3$, rotamers), 8.40 (0.33H, s), 7.83 (0.67H, br s), 6.88 (0.33H, br d, J=8.6 Hz), 6.69 (0.67H, br d, J=9.2 Hz), 4.90 (1H, t), 4.06 (0.33H, br dd, J=14.5, 7.4 Hz), 3.82 (0.67H, br dd, J=13.7, 9.8 Hz), 3.57-3.44 (1H, m), 3.16 (1H, s), 3.15 (2H, s), 2.98 (1H, s), 2.96 (2H, s), 2.87-2.63 (1H, m), 1.64-1.26 (4H, br m), 0.98 (3H, s), 0.94 (6H, s) and 0.90 (3H, t, J=7.3 Hz). $^{13}$C-NMR; δ (CDCl$_3$, rotamers), 175.8, 173.2, 172.0, 55.4, 54.9, 52.2, 48.7, 46.2, 45.0, 38.9, 38.9, 36.3, 36.1, 36.1, 32.7, 32.6, 27.0, 26.9, 20.9, 20.8 and 14.4. LRMS: +ve ion 338 [M+Na], −ve ion 314 [M−H].

EXAMPLE 17

2R (or S)-[Formyl-hydroxy-amino)-methyl]-4-methyl-pentanoic acid-(1S-dimethyl-carbamoyl-2,2-dimethyl-propyl)-amide

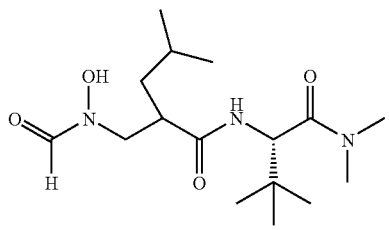

Diastereoisomer A. White hygroscopic solid. $^1$H-NMR; δ (CDCl$_3$, rotamers), 8.41 (0.4H, s), 7.83 (0.6H, s), 6.65 (0.4H, d, J=8.6 Hz), 6.55 (0.6H, d, J=9.0 Hz), 4.91-4.83 (1H, m), 4.03-3.95 (0.4H, m), 3.84-3.74 (0.6H, m), 3.62-3.43 (1H, m), 3.16 (1H, s), 3.13 (2H, s), 2.98 (1H, s), 2.96 (2H, s), 2.89-2.79 (0.6H, m), 2.76-2.71 (0.4H, m), 1.69-1.34 (1.8H, m), 1.29-1.20 (1.2H, m), 1.0 (3.6H, s), 0.95 (5.4H, s) and 0.93-0.88 (6H, m). $^{13}$C-NMR; δ (CDCl$_3$, rotamers), 175.8, 173.3, 172.0, 171.7, 55.5, 55.0, 52.4, 49.1, 44.3, 43.2, 39.5, 39.4, 38.9, 38.8, 36.3, 36.1, 27.0, 26.9, 26.3, 26.0, 23.1, 23.0 and 22.8. LRMS: +ve ion 352 [M+Na], −ve ion 328 [M−H].

EXAMPLE 18

3-Cyclohexyl-2R (or S)-[(formyl-hydroxy-amino)-methyl]-propionic acid (1S-dimethyl-carbamoyl-2,2-dimethyl-propyl)-amide

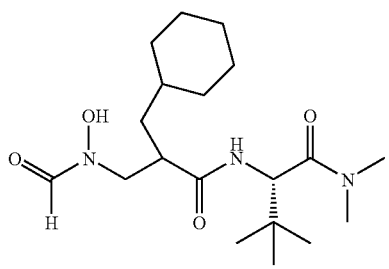

White solid. $^1$H-NMR; δ (CDCl$_3$, rotamers), 8.38 (0.25H, s), 7.82 (0.75H, s), 6.93 (0.25H, d, J=8.9 Hz), 6.74 (0.75H, d, J=8.9 Hz), 4.90 (1H, d, J=9.4 Hz), 4.02 (0.25H, dd, J=9.7, 14.1 Hz), 3.78 (0.75H, dd, J=9.7, 14.1 Hz), 3.46 (1H, m), 3.15 (3H, s), 2.96 (3H, s), 2.92 (1H, m), 1.65 (6H, m), 1.20 (5H, m), 0.98 (9H, s) and 0.87 (2H, m). $^{13}$C-NMR; δ (CDCl$_3$, rotamers), 176.4, 174.2, 172.4, 56.0, 55.6, 53.4, 49.9, 44.0, 43.3, 39.6, 39.4, 38.7, 38.5, 36.9, 36.7, 36.6, 34.8, 34.5, 27.5, 27.4 and 27.2. LRMS: +ve ion 370 [M+H], 368 [M−H].

EXAMPLE 19

2R (or S)-Cyclopentyl-3-(Formyl-hydroxy-amino)-propionic acid-(1S-dimethylcarbamoyl-2,2-dimethyl-propyl)-amide

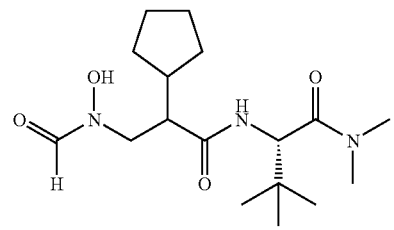

Diastereoisomer A. Off-white foam. $^1$H-NMR; δ (CD$_3$OD, rotamers), 8.22 (0.33H, s), 7.79 (0.66H, s), 4.89 (1H, s), 3.87 (1H, m), 3.50 (1H, m), 3.19 (3H, s,), 2.93 (3H, s), 2.82 (0.66H, m) 2.65 (0.33H, m), 1.89 (2H, m), 1.56 (5H, m), 1.24 (2H, m) and 0.98 (9H, s). $^{13}$C-NMR; δ (CD$_3$OD, rotamers), 176.0, 56.7, 53.2, 51.1, 42.7, 39.2, 36.5, 36.4, 32.0, 27.4, 26.4, and 26.2. IR (reflection disc) $v_{max}$ 3318, 2953, 1663, 1628, 1529, 1367, 1229, 1142, 1087, 877 cm$^{-1}$. LRMS: +ve ion 364 [M+Na], −ve ion 340 [M−H].

EXAMPLE 20

2R (or S)-[(Formyl-hydroxy-amino)-methyl]-octanoic acid (1S-dimethylcarbamoyl-2,2-dimethyl-propyl)-amide

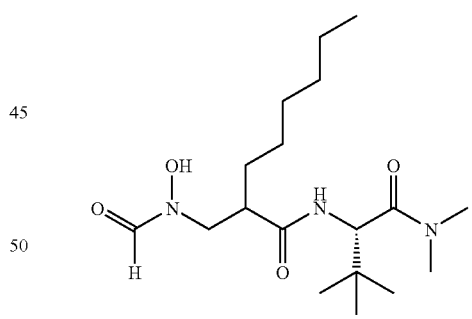

Diastereoisomer A. $^1$H-NMR; δ (CDCl$_3$, rotamers), 8.40 (0.4H, s), 7.83 (0.6H, s), 6.88 (0.4H, d, J=8.9 Hz), 6.68 (0.6H, d, J=9.2 Hz), 4.90 (1H, m), 4.05 (0.4H, m), 3.81 (0.6H, m), 3.50 (1H, m), 3.16 (1.2H, s), 3.15 (1.8H, s), 2.97 (1.2H, s), 2.96 (1.8H, s), 2.86 (0.6H, m), 2.69 (0.4H, m), 1.59-1.25 (10H, m), 1.14-0.95 (9H, m) and 0.89-0.77 (3H, m). $^{13}$C-NMR; δ (CDCl$_3$, rotamers), 175.2, 172.9, 171.6, 171.4, 54.9, 54.5, 54.3, 52.0, 48.4, 46.1, 45.7, 45.1, 44.7, 39.7, 38.5, 38.4, 35.8, 35.6, 35.6, 31.7, 31.5, 30.2, 30.1, 29.1, 29.1, 27.0, 26.4, 22.4 and 14.0. LRMS: +ve ion 380 [M+Na], 358 [M+H], −ve ion 356 [M−H].

EXAMPLE 21

2R (or S)-[(Formyl-hydroxy-amino)-methyl]-nonanoic acid (1S-dimethylcarbamoyl-2,2-dimethyl-propyl)-amide

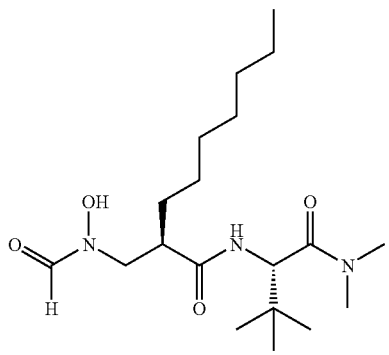

Diastereoisomer A: brown solid. ¹H-NMR; δ (CDCl₃, rotamers), 9.30 (0.4H, s), 8.41 (0.6H, s), 7.83 (0.4H, s), 6.66 (0.4H, d, J=8.9 Hz), 6.52 (0.6H, d, J=9.7 Hz), 4.92-4.84 (1H, m), 4.06-3.97 (0.4H, m), 3.87-3.77 (0.6H, m), 3.63-3.45 (1H, m), 3.16 (1.2H, s), 3.14 (1.8H, s), 2.98 (1.2H, s), 2.96 (1.8H, s), 2.86-2.74 (0.6H, m), 2.66-2.63 (0.4H, m), 1.95-1.25 (12H, m), 1.00-0.95 (9H, m), and 0.90-0.84 (3H, m). ¹³C-NMR; δ (CDCl₃, rotamers), 175.5, 172.8, 171.4, 162.2, 156.1, 55.1, 54.5, 51.3, 50.8, 48.4, 46.3, 44.9, 38.4, 38.4, 35.8, 35.7, 33.9, 31.7, 30.3, 30.2, 29.4, 29.0, 27.1, 26.5, 26.5, 24.9, 22.6 and 14.0. LRMS: +ve ion 394 [M+Na], 372 [M+H], −ve ion 370 [M−H].

EXAMPLE 22

2R (or S)-[(Formyl-hydroxy-amino)-methyl]-decanoic acid (1S-dimethylcarbamoyl-2,2-dimethyl-propyl)-amide

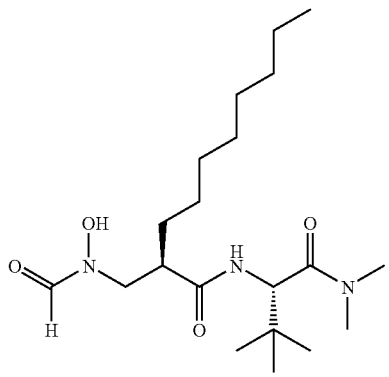

Diastereoisomer A: colourless oil. LRMS: +ve ion 408 [M+Na], 386 [M+H], −ve ion 384 [M−H].

EXAMPLE 23

2R (or S)-[(Formyl-hydroxy-amino)-methyl]-5-methyl-hexanoic acid (1S-dimethyl-carbamoyl-2,2-dimethyl-propyl)-amide

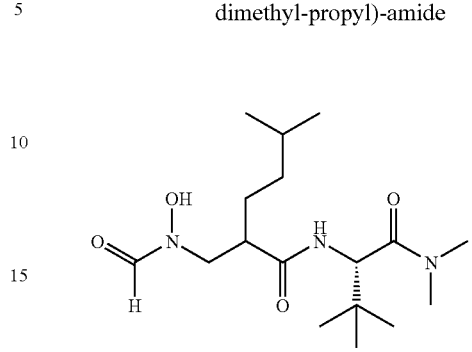

Diastereoisomer A: colourless oil. ¹H-NMR; δ (CDCl₃, rotamers), 9.31 (0.4H, s), 8.40 (0.4H, s), 8.17 (0.6H, s), 6.77 (0.4H, d, J=7.5 Hz), 6.60 (0.6H, d, J=8.0 Hz), 4.89 (1H, m), 4.04 (0.4H, m), 3.83 (0.6H, m), 3.52 (1H, m), 3.16 (1.2H, s), 3.15 (1.8H, s), 2.98 (1.2H, s), 2.96 (1.8H, s), 2.70 (1H, m), 1.58-1.14 (5H, m), 1.00-0.95 (9H, m) and 0.87-0.84 (6H, m). ¹³C-NMR; δ (CDCl₃, rotamers), 172.9, 171.5, 162.2, 156.3, 55.1, 54.6, 51.4, 48.5, 46.4, 45.0, 38.5, 38.4, 36.2, 35.9, 35.6, 29.7, 28.1, 28.0, 27.9, 26.7, 26.6, 26.5 and 22.4. LRMS: +ve ion 366 [M+Na], 344 [M+H], −ve ion 342 [M−H].

EXAMPLE 24

2R (or S)-[(Formyl-hydroxy-amino)-methyl]propanoic acid (1S-dimethylcarbamoyl-2,2-dimethyl-propyl)-amide

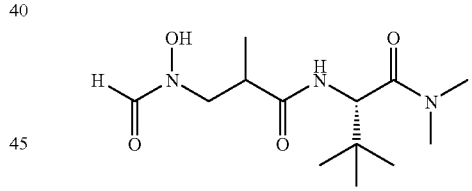

Diastereoisomer A: ¹H-NMR; δ (CDCl₃, rotamers), 8.41 (0.55H, s), 7.81 (0.45H, s), 6.67 (0.45H, d, J=8.4 Hz), 6.51 (0.45H, d, J=7.2 Hz), 4.88 (0.45H, d, J=9.4 Hz), 4.66 (0.55H, d, J=7.7 Hz), 3.76 (1H, m), 3.55 (0.55H, dd, J=14.3, 9.8 Hz), 3.44 (0.45H, dd, J=14.2, 5.3 Hz), 3.21 (1.65H, s), 3.14 (1.35H, s), 2.99 (1.65H, s), 2.97 (1.35H, s), 2.81 (1H, m), 1.21 (1.65H, d, J=6.7 Hz), 1.19 (1.35H, d, J=6.8 Hz), 1.01 (4.95H, s), and 0.98 (4.05H, s). LRMS: +ve ion 310 [M+Na], −ve ion 286 [M−H].

Diastereoisomer B: ¹H-NMR; δ (CDCl₃, rotamers), 9.47 (0.4H, br s), 8.41 (0.4H, s), 7.86 (0.6H, s), 6.96 (0.4H, br s), 6.74 (0.6H, d, J=7.3 Hz), 4.91 (1H, m), 3.99 (0.4H, dd, J=14.2, 7.6 Hz), 3.83 (0.6H, dd, J=13.8, 9.0 Hz), 3.50 (1H, m), 3.16 (1.2H, s), 3.15 (1.8H, s), 2.97 (3H, s), 2.90 (1H, m), 1.21 (1.2H, d, J=6.8 Hz), 1.15 (1.8H, d, J=6.5 Hz), 0.99 (3.6H, s) and 0.95 (5.4H, s). LRMS: +ve ion 310 [M+Na], −ve ion 286 [M−H].

EXAMPLE 25

2R (or S)-[(Formyl-hydroxy-amino)-methyl]-3-methyl butyric acid (1S-dimethyl-carbamoyl-2,2-dimethyl-propyl)-amide

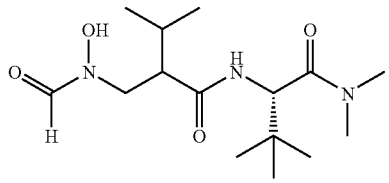

Diastereoisomer A: ¹H-NMR; δ (CDCl₃, rotamers), 9.33 (0.4H, s), 8.38 (0.4H, s), 7.81 (0.6H, s), 6.86 (0.4H, br s), 6.58 (0.6H, d, J=8.6 Hz), 4.90 (1H, m), 4.06 (0.4H, dd, J=14.7, 7.3 Hz), 3.91 (0.6H, dd, J=13.8, 10.6 Hz), 3.17 (1.2H, s), 3.15 (1.8H, s), 2.98 (1.2H, s), 2.96 (1.8H, s), 2.62 (0.6H, m), 2.48 (0.4H, m), 1.90 (1H, m), 1.09-0.86 (15H, m). LRMS: +ve ion 338 (M+Na), −ve ion 314 (M−H).

EXAMPLE 26

2R (or S)-[(Formyl-hydroxy-amino)-methyl]-3-phenyl-propionylpropionic acid-(1S-dimethylcarbamoyl-2,2-dimethyl-propyl)-amide

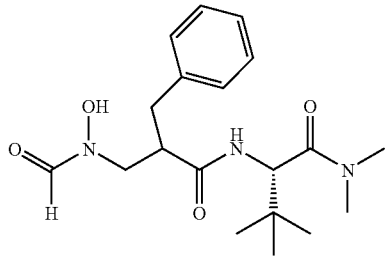

Diastereoisomer A. Colourless glass. ¹H-NMR; δ (CDCl₃, rotamers), 9.33 (0.3H, br s), 8.95 (0.7H, br s), 8.43 (0.3H, br s), 7.83 (0.7H, br s), 7.27-7.10 (5H, m), 6.65 (0.3H, br s), 6.45 (0.7H, br d, J=8.2 Hz), 4.80-4.70 (1H, m), 4.22-4.10 (0.3H, m), 3.89 (0.7H, dd, J=13.7, 9.6 Hz), 3.63-3.47 (1H, m), 3.20-2.69 (3H, m), 3.04 (3H, br s), 2.86 (3H, br s), and 0.87 (9H, br s). ¹³C-NMR; δ (CDCl₃, rotamers), 137.9, 137.7, 128.8, 128.5, 126.6, 54.9, 54.5, 51.3, 48.3, 47.3, 46.6, 38.3, 38.2, 36.2, 36.1, 35.8, 35.7, 35.6, 35.5 and 26.4. LRMS: +ve ion 386 (M+Na), −ve ion 362 (M−H).

EXAMPLE 27

2R (or S)-[(Formyl-hydroxy-amino)-methyl]-3-(4-methoxy-phenyl)-propionic acid-(1S-dimethyl carbamoyl-2,2-dimethyl-propyl)-amide

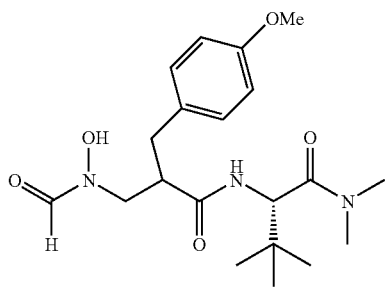

Diastereoisomer A: LRMS: +ve ion 416 (M+Na), 394 (M+H), −ve ion 392 (M−H).

The compounds of Examples 28 to 31 were prepared by analogy with Example 13, Method II, substituting the appropriate amino acid amide or benzyl ester for tert-leucine N,N-dimethylamide in Step E.

EXAMPLE 28

2S-{2R-[Formyl-hydroxy-amino)-methyl]-hexanoylamino}-3-phenyl propionic acid

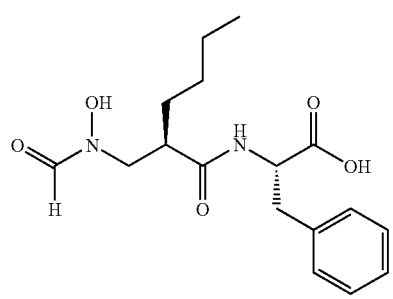

White foam. ¹H-NMR; δ (CD₃OD, rotamers), 8.11 (0.35H, s), 7.80 (0.65H, s), 7.31-7.16 (5H, m), 4.68 (1H, dd, J=8.7, 5.5 Hz), 3.58 (1H, m), 3.39 (1H, m), 3.19 (1H, m), 2.98 (1H, m), 2.76 (1H, m), 1.55-1.26 (6H, m) and 0.90-0.85 (3H, m). ¹³C-NMR; δ (CD₃OD, rotamers), 176.1, 175.7, 174.7, 174.5, 138.6, 138.5, 130.3, 129.5, 129.4, 127.7, 55.0, 53.3, 49.8, 45.4, 38.4, 38.3, 31.0, 30.8, 30.1, 23.7 and 14.2. IR (reflection disc) $v_{max}$ 2932, 2359, 1727, 1660, 1551, 1454, 1381, 1221, 882, 701 cm⁻¹. LRMS: +ve ion 359 [M+Na], −ve ion 335 (M−H).

EXAMPLE 29

2S-{2R-[Formyl-hydroxy-amino)-methyl]-hexanoylamino}-3,3-dimethyl butyric acid

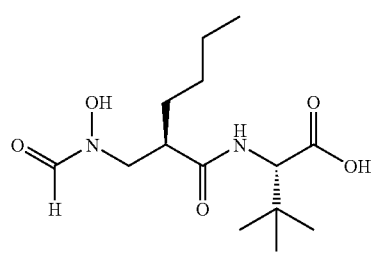

White foam. ¹H-NMR; δ (CD₃OD, rotamers), 8.25 (0.3H, s), 7.82 (0.7H, s), 4.31 (1H, s), 3.83-3.29 (2H, m), 3.10-2.89 (1H, m), 1.54-1.33 (6H, m), 1.03 (3H, s), 1.01 (6H, s) and 0.92-0.87 (3H, m). ¹³C-NMR; δ (CD₃OD, rotamers), 174.9, 172.9, 61.0, 52.4, 44.2, 44.0, 33.6, 30.1, 29.1, 26.2, 22.6 and 13.1. IR(reflection disc) $v_{max}$ 2959, 2359, 1644, 1537, 1371, 1218, 881 and 704 cm⁻¹. LRMS: +ve ion 325 (M+Na), −ve ion 301 (M−H).

EXAMPLE 30

2S-[2R-(Formyl-hydroxy-amino)-methyl]-hexanoic acid {1-[(2S-hydroxymethyl-pyrrolidine-1-carbamoyl]-2,2-dimethyl-propyl}-amide

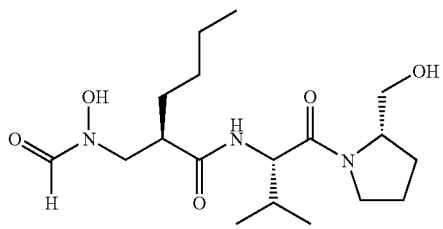

Colourless oil. $^1$H-NMR; δ (CD$_3$OD, rotamers), 8.26 (0.4H, s), 7.84 (0.6H, s), 4.62 (0.4H, d, J=8.2 Hz), 4.39 (0.6H, d, J=8.4 Hz), 4.12 (1H, m), 3.91-3.37 (6H, br m), 2.93 (0.6H, m), 2.78 (0.4H, m), 1.93 (5H, m), 1.45 (2H, m), 1.39 (3H, m), 0.97 (3H, br s), 0.95 (3H, br s), and 0.89 (3H, t, J=6.7 Hz). $^{13}$C-NMR; δ (CDCl$_3$, rotamers), 174.8, 172.9, 65.3, 65.1, 59.6, 59.5, 55.9, 55.7, 51.9, 47.8, 44.7, 44.0, 31.5, 30.5, 29.3, 28.7, 28.1, 27.3, 23.8, 22.0, 21.2, 18.7, 18.3, 17.6, 14.7 and 13.3. LRMS: +ve ion 394 (M+Na), 372 (M+H), −ve ion 370 (M−H).

EXAMPLE 31

2S-[2R-(Formyl-hydroxy-amino)-methyl]-hexanoic acid {1-[(2-hydroxy-ethyl)methyl-carbamoyl]-2,2-dimethyl-propyl}-amide

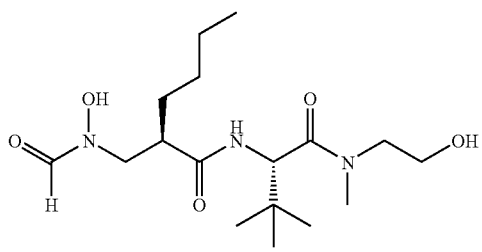

White foam. $^1$H-NMR; δ (CD$_3$OD, rotamers), 8.25 (0.25H, s), 8.03 (0.125H, s), 7.82 (0.625H, s), 4.88 (1H, m), 3.83-3.54 (4H, br m), 3.41 (2H, m), 3.25 (2H, s), 2.96 (2H, s and m), 1.49 (2H, m), 1.23 (4H, m), 1.00 (6H, s), 0.99 (3H, s), and 0.88 (3H, m). $^{13}$C-NMR; δ (CD$_3$OD, rotamers), 173.6, 164.4, 61.1, 61.0, 56.9, 56.5, 54.2, 53.9, 52.2, 41.8, 38.9, 36.9, 36.3, 35.3, 31.6, 30.8, 27.5, 24.1 and 14.7. LRMS: +ve ion 382 [M+Na], −ve ion 358 [M−H].

The compounds of Examples 32 to 59 were prepared by analogy with Example 7, Method II, substituting the appropriate amine or amino acid amide/benzyl ester for tert-leucine N,N-dimethylamide in Step E. In some cases HOAt was used in Step E and hydrogenolytic deprotection (Step G) was performed under catalytic transfer conditions (cyclohexene, palladium on charcoal in ethanol)

EXAMPLE 32

2R-[(Formyl-hydroxy-amino)-methyl]-hexanoic acid-(1R-dimethylcarbamoyl-2,2-dimethyl-propyl)-amide

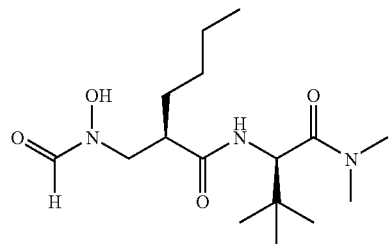

Colourless oil. LRMS: +ve ion 330 [M+H], −ve ion 328 [M−H].

EXAMPLE 33

2R-[(Formyl-hydroxy-amino)-methyl]-hexanoic acid (1S-dimethylcarbamoyl-2S-methyl-butyl)-amide

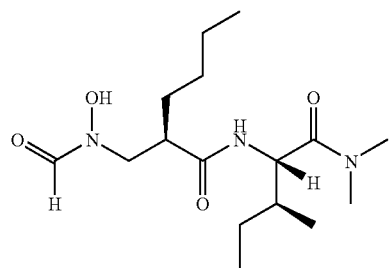

White foam. LRMS: +ve ion 352 [M+Na], −ve ion 328 [M−H].

EXAMPLE 34

2R-[(Formyl-hydroxy-amino)-methyl]-hexanoic acid (1S-dimethylcarbamoyl-2-methoxy-2-methyl-propyl)-amide

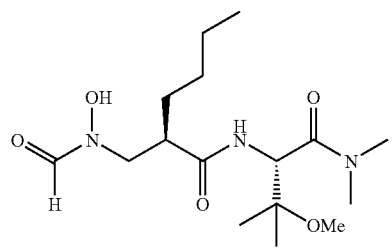

From racemic β-hydroxymethylvaline. Diastereoisomer A. Colourless oil. LRMS: +ve ion 368 [M+Na], 346 [M+H], −ve ion 344 [M−H]. Diastereoisomer B. LRMS: +ve ion 368 [M+Na], 346 [M+H], −ve ion 344 [M−H].

EXAMPLE 35

2R-[(Formyl-hydroxy-amino)-methyl]-hexanoic acid (1S-dimethylcarbamoyl-2-hydroxy-2-methyl-propyl)-amide

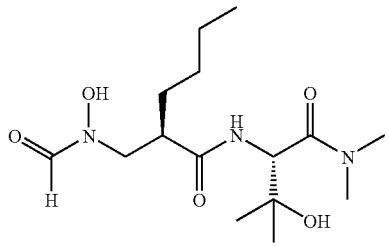

Colourless oil. LRMS: +ve ion 354 [M+Na], −ve ion 330 [M−H].

EXAMPLE 36

2R-[(Formyl-hydroxy-amino)-methyl]-hexanoic acid [2-(4-chloro-phenyl)-1S-dimethyl-carbamoyl-ethyl]-amide

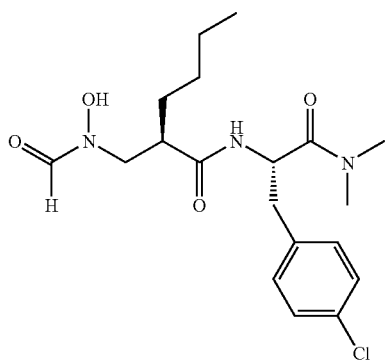

Colourless oil. LRMS: +ve ion 330 (M+H), −ve ion 328 (M−H).

EXAMPLE 37

2R-[(Formyl-hydroxy-amino)-methyl]-hexanoic acid [1S-dimethylcarbamoyl-2-(4-hydroxy-phenyl)-ethyl]-amide

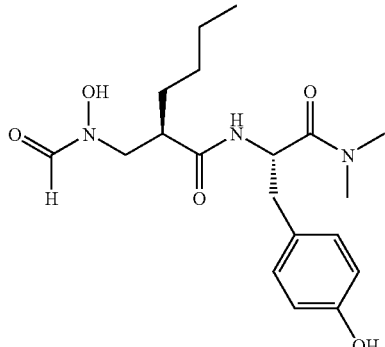

Colourless oil. LRMS: +ve ion 402 (M+Na), +ve ion 380 (M+H).

EXAMPLE 38

2R-[(Formyl-hydroxy-amino)-methyl]-hexanoic acid (1S-dimethylcarbamoyl-2-naphthalen-2-yl-ethyl)-amide

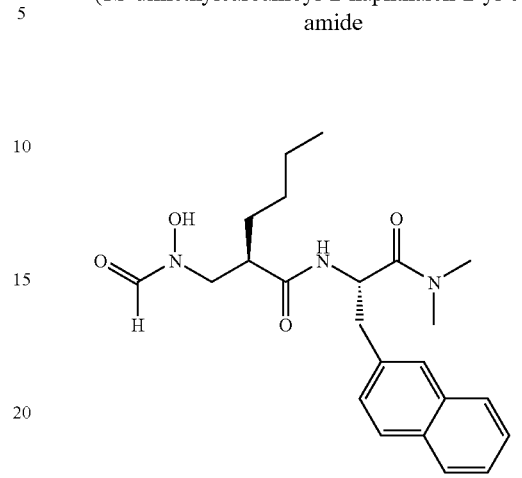

Colourless oil. LRMS: +ve ion 414 (M+H), −ve ion 412 (M−H).

EXAMPLE 39

2R-[(Formyl-hydroxy-amino)-methyl]-hexanoic acid (2-cyclohexyl-1S-dimethyl-carbamoyl-ethyl)-amide

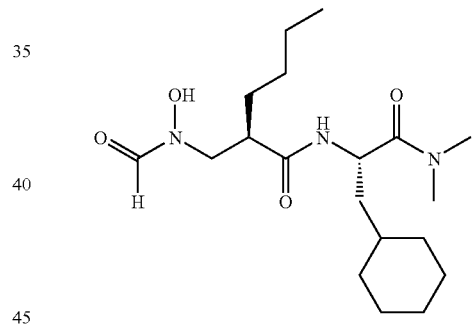

White foam. LRMS: +ve ion 392 (M+Na), 370 (M+H)

EXAMPLE 40

2R-[(Formyl-hydroxy-amino)-methyl]-hexanoic acid (1S-dimethylcarbamoyl-phenyl-methyl)-amide

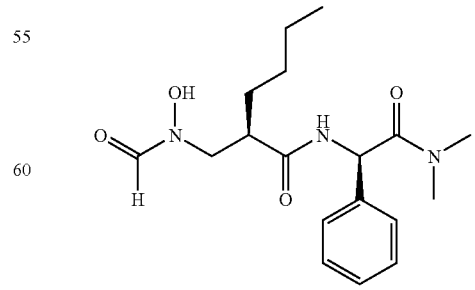

Colourless oil. LRMS: +ve ion 350 (M+H), −ve ion 348 (M−H).

EXAMPLE 41

2-{2R-[(Formyl-hydroxy-amino)-methyl]-hexanoyl}-1,2,3,4-tetrahydro-isoquinoline-3S-carboxylic acid dimethylamide

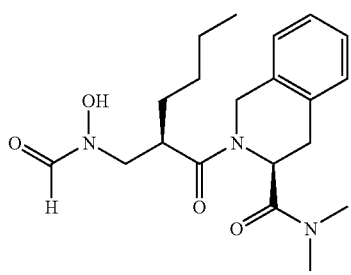

LRMS: +ve ion 398 (M+Na), 376 (M+H), −ve ion 374 (M−H).

EXAMPLE 42

2R-[(Formyl-hydroxy-amino)-methyl]-hexanoic acid (4-amino-1S-dimethylcarbamoyl-butyl)-amide

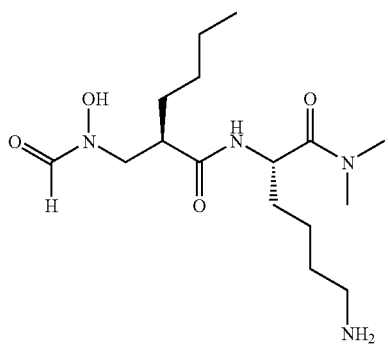

Colourless oil. LRMS: +ve ion 345 (M+H), −ve ion 343 (M−H).

EXAMPLE 43

2R-[(Formyl-hydroxy-amino)-methyl]-hexanoic acid (1S-dimethylcarbamoyl-2-hydroxy-ethyl)-amide

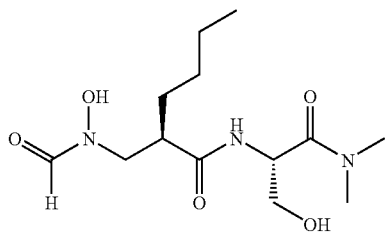

Colourless oil. LRMS: +ve ion 326 (M+Na), −ve ion 302 (M−H).

EXAMPLE 44

N-Hydroxy-N-[2R-(4-methyl-piperazine-1-carbonyl)-hexyl]-formamide

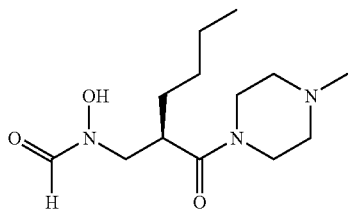

LRMS: +ve ion 272 [M+H].

EXAMPLE 45

N-Hydroxy-N-[2R-(morpholine-4-carbonyl)-hexyl]-formamide

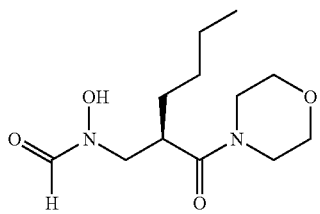

LRMS: +ve ion 281 (M+Na), 259 (M+H), −ve ion 257 (M−H).

EXAMPLE 46

N-Hydroxy-N-[2R-(2S-hydroxymethyl-pyrrolidine-1-carbonyl)-hexyl]-formamide

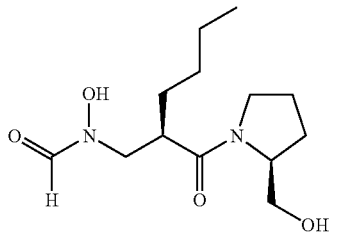

LRMS: −ve ion 271 (M−H).

EXAMPLE 47

2R-[(Formyl-hydroxy-amino)-methyl]-hexanoic acid (1S-hydroxymethyl-2,2-dimethyl-propyl)-amide

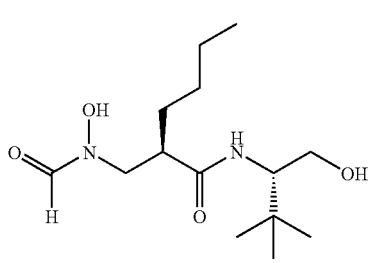

LRMS: +ve ion 289 (M+H), −ve ion 287 (M−H).

EXAMPLE 48

2R-[(Formyl-hydroxy-amino)-methyl]-hexanoic acid (1S-methoxymethyl-2,2-dimethyl-propyl)-amide

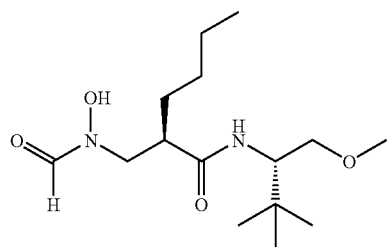

LRMS: +ve ion 303 (M+H), −ve ion 301 (M−H).

EXAMPLE 49

2R-[(Formyl-hydroxy-amino)-methyl]-hexanoic acid [1S-(4-benzyl-piperidine-1-carbonyl)-2,2-dimethyl-propyl]-amide

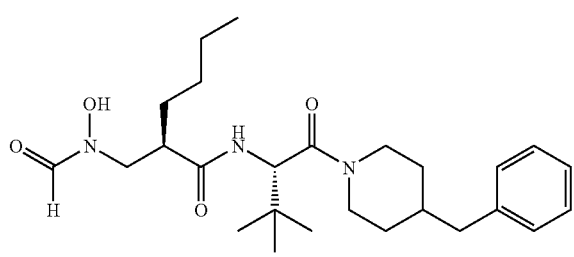

LRMS: −ve ion 458 (M−H).

EXAMPLE 50

2R-[(Formyl-hydroxy-amino)-methyl]-hexanoic acid [1S-(benzyl-phenethyl-carbamoyl)-2,2-dimethyl-propyl]-amide

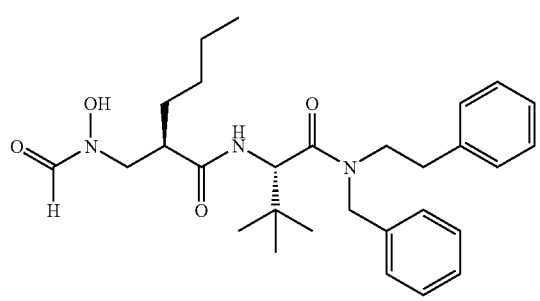

LRMS: +ve ion 496 (M+H), −ve ion 494 (M−H).

EXAMPLE 51

2S-[(Formyl-hydroxy-amino)-methyl]-hexanoic acid [2,2-dimethyl-1S-(pyrrolidine-1-carbonyl)-propyl]-amide

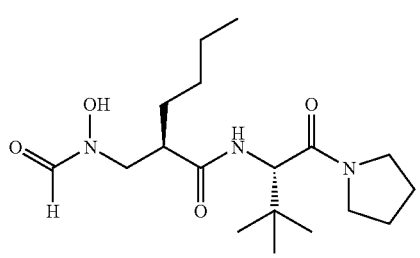

LRMS: +ve ion 356 (M+H), −ve ion 354 (M−H).

EXAMPLE 52

2R-[(Formyl-hydroxy-amino)-methyl]-hexanoic acid [2,2-dimethyl-1S-(morpholine-4-carbonyl)-propyl]-amide

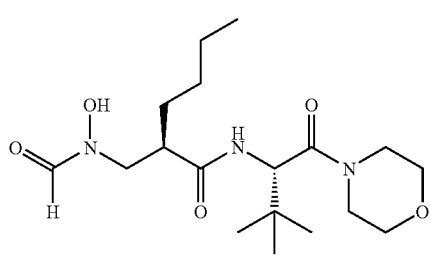

LRMS: +ve ion 372 (M+H), −ve ion 370 (M−H).

EXAMPLE 53

2R-[(Formyl-hydroxy-amino)-methyl]-hexanoic acid [2,2-dimethyl-1S-(4-methyl-piperazine-1-carbonyl)-propyl]-amide

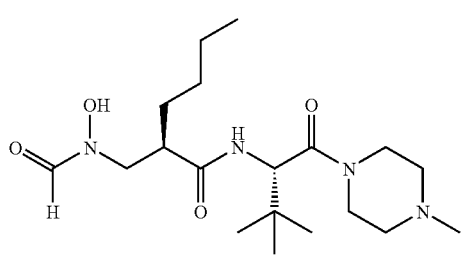

LRMS: +ve ion 385 (M+H), −ve ion 383 (M−H).

EXAMPLE 54

2R-[(Formyl-hydroxy-amino)-methyl]-hexanoic acid [2,2-dimethyl-1S-(4-methyl-piperidine-1-carbonyl)-propyl]-amide

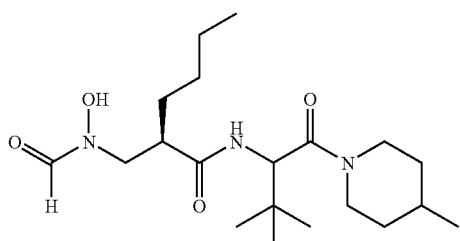

LRMS: +ve ion 384 (M+H), −ve ion 382 (M−H).

EXAMPLE 55

2R-[(Formyl-hydroxy-amino)-methyl]-hexanoic acid (1S-cyclohexylcarbamoyl-2,2-dimethyl-propyl)-amide

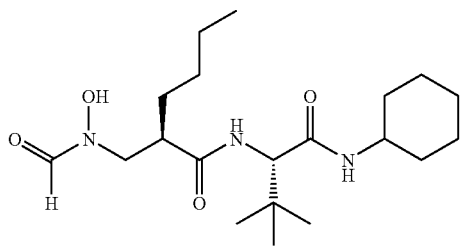

LRMS: +ve ion 398 (M+H), −ve ion 396 (M−H).

EXAMPLE 56

2R-[(Formyl-hydroxy-amino)-methyl]-hexanoic acid [1S-(4-acetyl-piperidine-1-carbonyl)-2,2-dimethyl-propyl]-amide

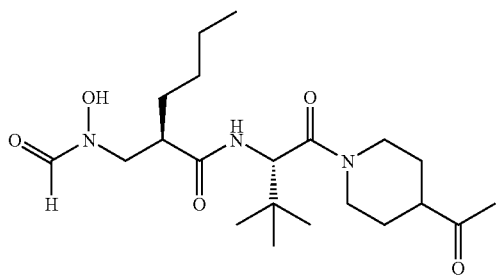

LRMS: +ve ion 412 (M+H), −ve ion 410 (M−H).

EXAMPLE 57

1-(2S-2R-[(Formyl-hydroxy-amino)-methyl]-hexanoylaminol-3,3-dimethyl-butyryl)-piperidine-4-carboxylic acid methyl ester

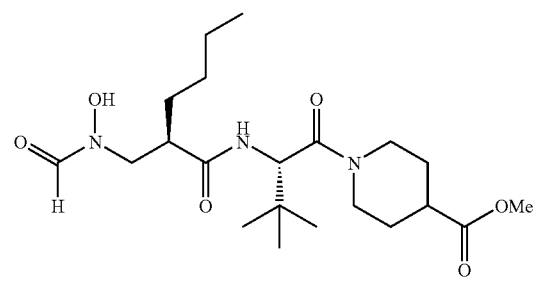

LRMS: +ve ion 442 (M+H), −ve ion 440 (M−H).

EXAMPLE 58

2R-[(Formyl-hydroxy-amino)-methyl]-hexanoic acid [2,2-dimethyl-1S-(octahydro-quinoline-1-carbonyl)-propyl]-amide

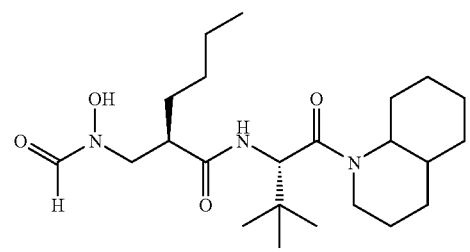

LRMS: +ve ion 424 (M+H), −ve ion 422 (M−H).

EXAMPLE 59

2R-[(Formyl-hydroxy-amino)-methyl]-hexanoic acid [1S-(3,4-dihydro-2H-quinoline-1-carbonyl)-2,2-dimethyl-propyl]-amide

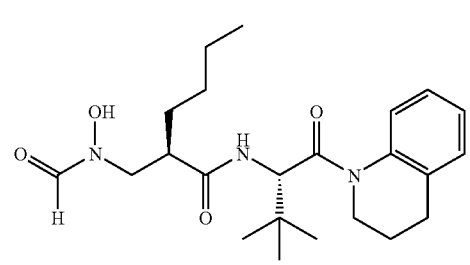

LRMS: −ve ion 416 (M−H).

EXAMPLE 60

2S-{3-Ethylsulfanymethyl-2R-[(formyl-hydroxy-amino)-methyl]propionyl amino}-3,3,N,N-tetramethylbutyramide

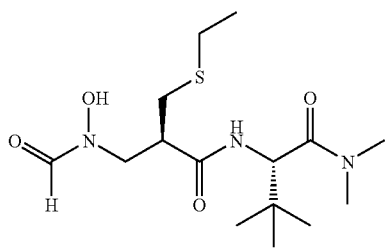

A synthetic route to the title compound is outlined in Scheme 4 and is described in detail below.

Scheme 4

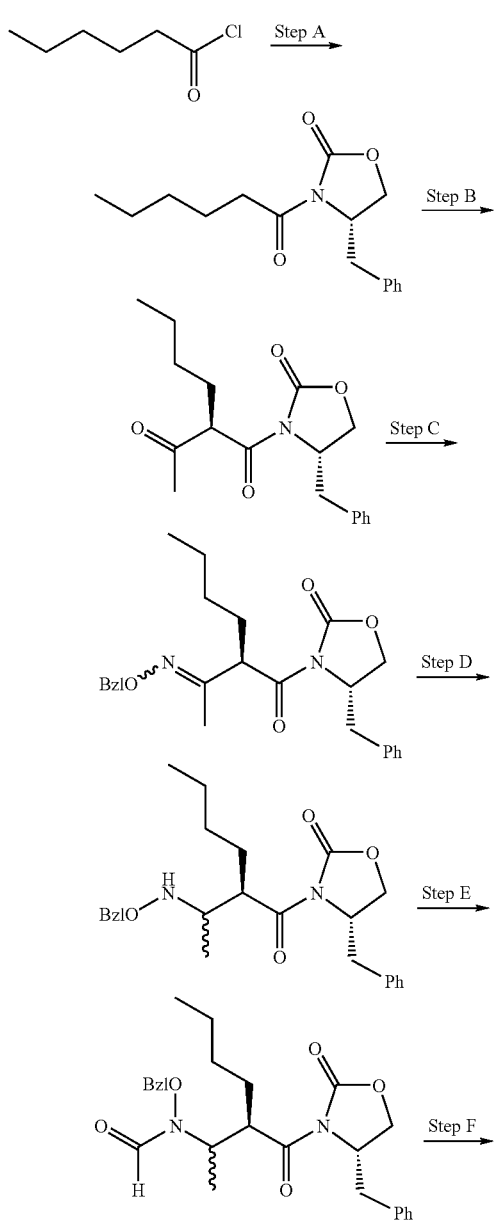

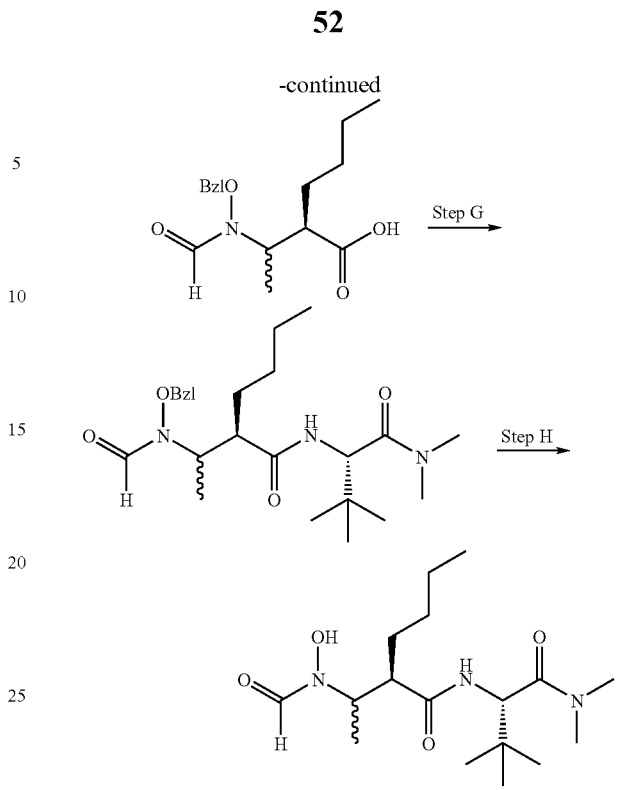

Reagents and conditions:
A. 3-lithio-4-benzyl-oxazolidin-2-one, THF, -78° C.;
B. LiN(SiMe$_3$)$_2$, THF, -78° C. then AcCl;
C. HCl•H$_2$NOBzl, NaOAc, aq ethanol;
D. NaCNBH$_3$, AcOH, room temperature;
E. HCOBt, THF;
F. LiOH, aq THF, 0° C.;
G. H-Tle-NMe$_2$, HOAt, EDC, DMF;
H. H$_2$, Pd/C, MeOH then separate diastereoisomers (HPLC)

Step A: 2-Ethylsulfanylmethyl-acrylic acid

A mixture of malonic acid (5.2 g, 50 mmol), paraformaldehyde (3.3 g, 110 mmol), dicyclohexylamine, 9.95 ml, 50 mmol) and ethanethiol 4.06 ml, 55 mmol) in dioxane (120 ml) was heated at 70° C. for 2 hours. The solvents were removed under reduced pressure, the residue was redissolved in ethyl acetate and the solution was extracted with saturated aqueous sodium hydrogen carbonate (4×20 ml). The combined aqueous layers were washed with ethyl acetate (20 ml) then acidified with 1 M hydrochloric acid. The resulting suspension was extracted into dichloromethane and the solution was dried over anhydrous magnesium sulfate, filtered and evaporated to provide the title compound as a white solid (3.76 g, 52%). $^1$H-NMR; δ (CDCl$_3$), 9.89 (1H, brs), 6.35 (1H, s), 5.77 (1H, s), 3.39 (2H, s), 2.49 (2H, dd, J=7.4, 14.5 Hz) and 1.25 (3H, t, J=5.2 Hz).

Step B: 4S-Benzyl-3-(2-ethylsulfanylmethyl-acryloyl)-5,5-dimethyl-oxazolidin-2-one 2-Ethylsulfanylmethyl-acrylic acid (3.76 g, 25.8 mmol) was dissolved in dry THF (75 ml) and cooled to -78° C. under a blanket of argon. Triethylamine (4.6 ml, 33.5 mmol) and pivaloyl chloride (3.17 ml, 25.8 mmol) were added at such a rate that the temperature remained below -60° C. The mixture was stirred at -78° C. for 30 minutes, warmed to room temperature for 2 hours and finally cooled back to -78° C.

In a separate flask, 4S-benzyl-5,5-dimethyl-oxazolidin-2-one was dissolved in dry THF (75 ml) and cooled to -78° C.

under a blanket of argon. n-Butyllithium (2.4M solution in hexanes, 12.9 ml, 30.9 mmol) was added slowly and the mixture was stirred for 30 minutes at room temperature. The resulting anion was transferred via a cannula into the original reaction vessel. The mixture was allowed to warm to room temperature and stirred overnight at room temperature. The reaction was quenched with saturated sodium hydrogen carbonate (20 ml) and the solvents were removed under reduced pressure. The residue was partitioned between ethyl acetate and water. The organic layer was washed successively with saturated sodium hydrogen carbonate, 1 M hydrochloric acid and brine, dried over anhydrous magnesium sulfate, filtered and concentrated under reduced pressure. The residue was purified by flash chromatography (silica gel, 20% ethyl acetate in hexane) to provide the title compound as a yellow oil (6.5 g, 76%). $^1$H-NMR; δ (CDCl$_3$), 7.29 (5H, m), 5.58 (1H, s), 5.49 (1H, s), 4.54 (1H, dd, J=3.9, 9.7 Hz), 3.52 (2H, dd, J=15.8, 3.1 Hz), 3.38 (1H, dd, J=3.9, 14.5 Hz), 2.84 (1H, dd, J=4.6, 14.3 Hz), 2.52 (2H, dd, J=7.2, 14.6 Hz), 1.42 (3H, s), 1.29 (3H, s) and 1.22 (3H, t, J=7.5 Hz). LRMS: +ve ion 356 (M+Na), 334 (M+H).

Step C: 4S-Benzyl-3-[(2R-tert-butoxyamino-methyl)-3-ethylsulfanylmethyl-propionyl]-5,5-dimethyl-oxazolidin-2-one 4S-Benzyl-3-(2-ethylsulfanylmethyl-acryloyl)-5,5-dimethyl-oxazolidin-2-one (2.1 g, 6.3 mmol) was dissolved in ethanol (10 ml) and O-tert-butyl-hydroxylamine hydrochloride (0.95 g, 7.56 mmol) was added, followed by triethylamine (1.1 ml, 7.87 mmol). The mixture was stirred at 30° C. overnight. The solvents were removed under reduced pressure and the residue was dissolved in ethyl acetate. The organic solution was washed successively with 1 M hydrochloric acid, saturated sodium hydrogen carbonate and brine, dried over anhydrous magnesium sulphate and filtered. The filtrate was concentrated under reduced pressure to provide the title compound as a pale yellow oil (2.42 g, 91%; single diastereoisomer by HPLC). $^1$H-NMR; δ (CDCl$_3$), 7.30 (5H, m), 5.09 (1H, br s), 4.54 (1H, dd, J=3.5, 9.9 Hz), 4.33 (1H, m), 3.19 (2H, m), 3.08 (1H, dd, J=5.4, 11.8 Hz), 2.80 (3H, m), 2.56 (2H, dd, J=7.4, 14.7 Hz), 1.41 (3H, s), 1.36 (3H, s), 1.23 (3H, t, J=7.3 Hz) and 1.13 (9H, s). LRMS: +ve ion 423 (M+H).

Step D: (2R-tert-butoxyamino-methyl)-3-ethylsulfanylmethyl-propionic acid

A solution of 4S-Benzyl-3-[(2R-tert-butoxyamino-methyl)-3-ethylsulfanylmethyl-propionyl]-5,5-dimethyl-oxazolidin-2-one in (2.42 g, 5.72 mmol) THF (40 ml) was cooled to 0° C. and a solution of lithium hydroxide (288 mg, 6.86 mmol) in water (10 ml) was added. The mixture was allowed to warm to room temperature then stirred for 5 hours. The solvent was removed under reduced pressure and the residue was partitioned between water and ethyl acetate. The aqueous layer was removed and the ethyl acetate layer was washed successively with water and saturated sodium hydrogen carbonate. The combined aqueous layers were washed with ethyl acetate (20 ml) before acidifying with 1 M hydrochloric acid. The resulting emulsion was extracted with dichloromethane (3×20 ml) and the combined organic layers were dried over anhydrous magnesium sulfate, filtered and evaporated to provide the title compound as a colourless oil (0.68 g, 50%). $^1$H-NMR; δ (CDCl$_3$), 8.03 (2H, br s), 3.21 (2H, d, J=6.1 Hz), 2.89 (2H, m), 2.75 (1H, m), 2.57 (2H, dd, J=7.4, 14.8 Hz), 1.26 (3H, t, J=7.4 Hz) and 1.18 (9H, s). LRMS: +ve ion 236 [M+H], −ve ion 234 M−H].

Step E: A solution of 2S-[2R-(tert-butoxy-aminomethyl)-3-ethylsulfanylmethyl-propionyl amino}-3,3,N,N-tetramethylbutyramide 2R-tert-butoxyamino-methyl)-3-ethylsulfanylmethyl-propionic acid (340 mg, 1.44 mol) was dissolved in DMF (10 ml) and tert-leucine-N,N-dimethylamide (272 mg, 1.73 mmol), HOAt (19.6 mg, 0.14 mmol) and EDC (331 mg, 1.73 mmol) were added. The reaction was stirred overnight at room temperature. The solvent was removed under reduced pressure and the residue was dissolved in dichloromethane. The organic solution was washed successively with 1 M hydrochloric acid, 1 M sodium carbonate and brine, dried over anhydrous magnesium sulfate and filtered. The filtrate was concentrated under reduced pressure to provide the required product as a colourless oil (440 mg, 82%). $^1$H-NMR; δ (CDCl$_3$), 6.87 (1H, d, J=9.0 Hz), 5.11 (1H, br s), 4.93 (1H, d, J=9.3 Hz), 3.15 (3H, s), 3.11 (1H, m), 2.95 (3H, s), 2.79 (3H, m), 2.54 (3H, s), 1.22 (3H, t, J=7.6 Hz), 1.18 (9H, s) and 1.01 (9H, s). LRMS: +ve ion 398 [M+Na], 376 [M+1].

Step F: 2S-{2R-[(tert-Butoxy-formyl-amino)-methyl]-3-ethylsulfanylmethyl-propionyl amino}-3,3,N,N-tetramethylbutyramide A solution of 2S-[2R-(tert-butoxy-amino-methyl)-3-ethylsulfanylmethyl-propionyl amino}-3,3,N,N-tetramethylbutyramide (220 mg, 0.58 mmol) in dichlormethane (5 ml) was cooled to 0° C. and treated with formic acetic anhydride (0.1 ml). The reaction was stirred at room temperature for 4 hours, then the solvent was evaporated under reduced pressure. The residue was purified by flash chromatography (silica gel, 50% ethyl acetate in hexane as eluent) to provide the title compound as a colourless oil (120 mg, 52%). $^1$H-NMR; δ (CDCl$_3$, rotamers), 8.31 (1H, br s), 6.56 (1H, d, J=9.1 Hz), 4.94 (0.33H, d, J=9.4 Hz), 4.88 (0.67H, d, J=9.2 Hz), 4.08 (0.67H, br m), 3.83 (1.34H, br m), 3.13 (3H, s), 2.95 (3H, s), 2.80 (2H, m), 2.61 (1H, dd, J=6.8, 14.0 Hz), 2.49 (2H, dd, J=7.4, 14.7 Hz), 1.29 (9H, s), 1.25 (3H, t, J=7.2 Hz) and 0.99 (9H, s). LRMS: +ve ion 426 [M+Na], 404 [M+H].

Step G: 2S-{3-Ethylsulfanymethyl-2R-[(formyl-hydroxy-amino)-methyl]propionyl amino}-3,3,N,N-tetramethylbutyramide A solution of 2S-{2R-[(tert-butoxy-formyl-amino)-methyl]-3-ethylsulfanylmethyl-propionyl amino}-3,3,N,N-tetramethylbutyramide (120 mg, 0.3 mmol) in deuterochloroform (1 ml) was treated with TFA (4 ml) and allowed to stand at 4° C. overnight. The solvents were removed under reduced pressure and residual TFA was removed by azeotroping with toluene. The residue was purified by preparative HPLC to provide the title compound as a colourless oil (40 mg, 38%; 7:2 mixture of diastereomers by HPLC). $^1$H-NMR; δ (CDCl$_3$, rotamers), 8.40 (0.33H, s), 7.87 (0.67H, s), 7.24 (0.33H, d, J=9.3 Hz), 6.98 (0.67H, d, J=9.3 Hz), 4.91 (0.67H, d, J=9.3 Hz), 4.90 (0.33H, d, J=9.3 Hz), 4.07 (0.33H, dd, J=7.5, 14.5 Hz), 3.86 (0.67H, dd, J=8.8, 14.2 Hz), 3.75 (0.67H, m), 3.68 (0.33H, m), 3.16 (1H, s), 3.15 (2H, s), 3.05 (1H, m), 2.96 (3H, s), 2.77 (1H, m), 2.66 (1H, m), 2.52 (2H, dd, J=7.4, 14.8 Hz), 1.22 (3H, t, J=7.3 Hz), 0.99 (3H, s) and 0.96 (6H, s). $^{13}$C-NMR; δ (CDCl$_3$, rotamers), 173.3, 171.6, 171.2, 55.2, 54.8, 51.1, 48.5, 45.2, 44.4, 38.5, 38.4, 35.9, 35.8, 35.7, 31.7, 31.4, 26.7, 26.6, 26.5 and 14.6. LRMS: +ve ion 370 [M+Na], 348 [M+H], −ve ion 346 [M−H].

The compound of Example 61 was prepared similarly using piperidine in place of ethanethiol in Step A.

EXAMPLE 61

2-{2-[(Formyl-hydroxy-amino)-methyl]-3-piperidin-1-yl-propionylamino}-3,3,N,N-tetramethyl-butyramide

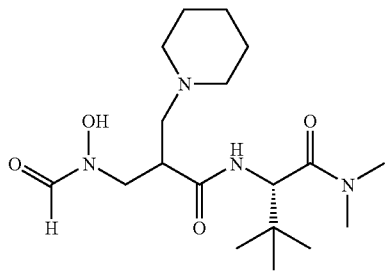

White solid (4:1 mixture of diastereoisomers by HPLC). $^1$H-NMR; δ (CDCl$_3$, rotamers), 8.29 (1H, s), 7.95 (1H, br s), 4.87 (1H, d, J=9.1 Hz), 4.02 (1H, dd, J=5.0, 14.6 Hz), 3.56 (1H, dd, J=8.2, 14.6 Hz), 3.14 (3H, s), 2.96 (3H, s), 2.89 (1H, m), 2.69 (1H, m), 2.52 (5H, m), 1.65 (4H, m), 1.49 (2H, m) and 0.99 (9H, s). $^{13}$C-NMR; δ (CDCl$_3$), 172.2, 171.3, 60.4, 55.0, 54.9, 48.6, 42.4, 38.8, 36.2, 36.1, 27.0, 25.6 and 24.3. LRMS: +ve ion 371 [M+H], −ve ion 369 [M−H].

The compounds of Examples 62 to 65 were prepared by analogy with Example 7, Method II, substituting O-tert-butylhydroxylamine for O-benzylhydroxylamine in Step B and the appropriate amine or amino acid amide/benzyl ester for tert-leucine N,N-dimethylamide in Step E. Final deprotection was performed by acidolysis with TFA (see Example 60, above).

EXAMPLE 62

2R-[(Formyl-hydroxy-amino)-methyl]-hexanoic acid (1R-dimethylcarbamoyl-2-methyl-2-methylsulfanyl-propyl)-amide

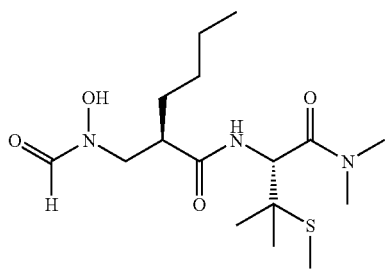

Colourless oil. $^1$H-NMR; δ (CDCl$_3$, rotamers), 8.4 (0.5H, s), 7.85 (0.5H, s), 7.11 (0.5H, d, J=9.1 Hz), 6.93 (0.5H, d, J=9.1 Hz), 5.15 (1H, d, J=9.4 Hz), 3.90 (0.5H, m), 3.73 (0.5H, m), 3.64 (0.5H, d, J=14.3 Hz), 3.48 (0.5H, dd, J=14.0,3.9 Hz), 3.22 (3H, s), 2.97 (3H, s), 2.83 (0.5H, m), 2.70 (0.5H, m), 2.07 (1.5H, s), 2.04 (1.5H, s), 1.58 (1H, m), 1.36 (4H, m), 1.32 (3H, s), 1.28 (3H, s) and 0.86 (3H, t, J=6.6 Hz). $^{13}$C-NMR; δ (CDCl$_3$, rotamers), 175.4, 173.5, 170.8, 63.6, 53.2, 53.1, 52.5, 49.5, 47.5, 46.1, 44.9, 41.6, 37.5, 36.5, 36.4, 35.4, 30.2, 29.8, 28.0, 14.3, 12.0 and 11.9. LRMS: +ve ion 362 [M+H], −ve ion 360 [M−H].

EXAMPLE 63

2R-[(Formyl-hydroxy-amino)-methyl]-hexanoic acid (2-benzylsulfanyl-1S-dimethyl-carbamoyl-2-methyl-propyl)-amide

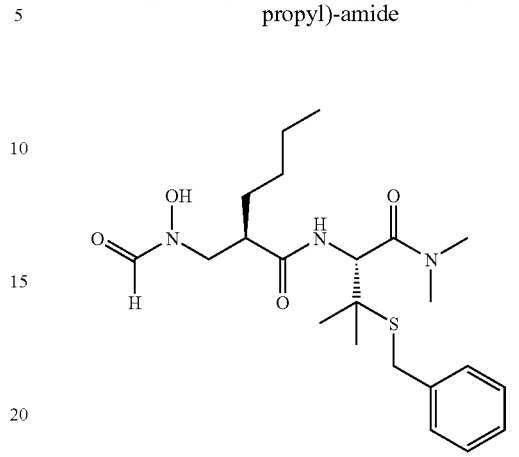

White foam. $^1$H-NMR; δ (CDCl$_3$, rotamers), 8.37 (0.33H, s), 7.81 (0.66H, s), 7.31 (5H, m), 7.06 (0.33H, d, J=8.8 Hz), 6.89 (0.66H, d, J=9.3 Hz), 5.20 (1H, d, J=9.3 Hz), 3.94 (0.33H, dd, J=8.3, 14.6 Hz), 3.78 (2.66H, m), 3.61 (0.33H, dd, J=3.5, 14.4 Hz), 3.42 (0.66H, dd, J=5.1, 14.9 Hz), 3.21 (3H, s), 3.03 (3H, s), 2.82 (0.66H, m), 2.69 (0.33H, m), 1.61 (1H, m), 1.42 (1H, m), 1.37 (3H, s), 1.32 (3H, s), 1.26 (4H, m) and 0.86 (3H, t, J=6.6 Hz). $^{13}$C-NMR; δ (CDCl$_3$, rotamers), 175.3, 173.5, 171.0, 138.1, 137.4, 129.5, 129.3, 129.1, 129.0, 128.9, 127.6, 127.4, 55.9, 53.7, 52.5, 51.2, 49.6, 49.5, 46.1, 44.9, 39.0, 38.6, 36.6, 36.4, 33.9, 33.7, 30.3, 30.1, 29.7, 26.7, 26.1, 25.7, 25.5, 24.2, 22.9 and 14.3. LRMS: +ve ion 460 [M+Na], 438 [M+H], −ve ion 436 [M−H].

EXAMPLE 64

2R-[(Formyl-hydroxy-amino)-methyl]-hexanoic acid [2-benzylsulfanyl-2-methyl-1S-(morpholine-4-carbonyl)-propyl]-amide

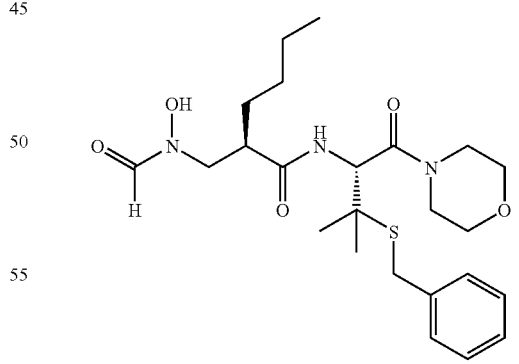

White foam. $^1$H-NMR; δ (CDCl$_3$, rotamers), 8.44 (0.5H, s), 8.37 (0.5H, s), 7.30 (5H, m), 6.88 (0.5H, d, J=8.3 Hz), 6.78 (0.5H, d, J=9.2 Hz), 5.12 (1H, d, J=9.5 Hz), 3.91 (1H, dd, J=8.2, 14.6 Hz), 3.78 (10H, m), 3.45 (1H, dd, J=4.5, 14.2 Hz), 2.80 (0.5H, m), 2.64 (0.5H, m), 1.61 (1H, m), 1.41 (1H, m), 1.36 (3H, s), 1.33 (3H, s), 1.29 (4H, m) and 0.87 (3H, t, J=6.8 Hz). $^{13}$C-NMR; δ (CDCl$_3$, rotamers), 175.5, 173.4, 169.4, 137.8, 129.5, 129.3, 129.1, 129.0, 127.8, 127.5, 67.1, 67.0, 53.3, 53.2, 51.99, 49.6, 49.5, 49.2, 47.9, 46.5, 45.0, 43.2, 43.0, 34.0, 30.3, 30.2, 29.7, 26.8, 26.5, 25.9, 25.8, 22.9 and 14.3. LRMS: +ve ion 502 [M+Na], 480 [M+H], −ve ion 478 [M−H].

EXAMPLE 65

2-[(Formyl-hydroxy-amino)-methyl]-hexanoic acid [2-benzylsulfanyl-2-methyl-1R (or S)-(4-methyl-piperidine-1-carbonyl)-propyl]-amide

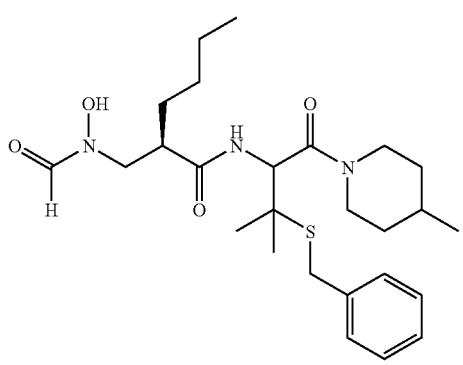

Diastereoisomer A. White solid. LRMS: +ve ion 514 [M+Na], 492 [M+H], −ve ion 490 [M−H].

Diastereoisomer B. Colourless gum. LRMS: +ve ion 514 [M+Na], 492 [M+H], −ve ion 490 [M−H].

The compounds of Examples 66 to 68 were prepared by analogy with Example 7, Method II, substituting the appropriate malonic acid for butylmalonic acid in Step A. O-tert-butylhydroxylamine for O-benzylhydroxylamine in Step C. Stereoselectivity in the Michael addition was variable. Final deprotection was performed by acidolysis with TFA (see Example 60, above).

EXAMPLE 66

2R-[(Formyl-hydroxy-amino)-methyl]-pent-4-enoic acid (1S-dimethylcarbamoyl-2,2-dimethyl-propyl)-amide

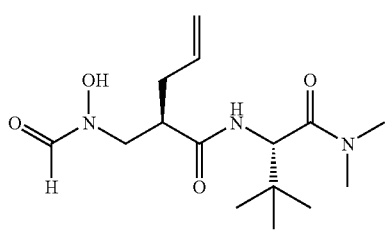

Single diastereoisomer. $^1$H-NMR; δ (CDCl$_3$, rotamers), 8.40 (0.25H, s), 7.84 (0.75H, s), 7.05 (0.35H, d, J=9.0 Hz), 6.74 (0.65H, d, J=9.3 Hz), 5.70 (1H, m), 5.03-5.24 (2H, m), 4.88 (1H, dd, J=9.4, 6.7 Hz), 3.98 (0.5H, m), 3.81 (0.5H, m), 3.55 (1H, m), 3.14 (3H, s), 2.97 (1.3H, s), 2.96 (1.7H, s), 2.75-2.92 (1H, m), 2.16-2.50 (2H, m), 0.98 (4H, s), and 0.94 (4.5H, s). LRMS: +ve ion 336 [M+Na], −ve ion 312 [M−H].

EXAMPLE 67

2R-[(Formyl-hydroxy-amino)-methyl]-hex-5-enoic acid (1S-dimethylcarbamoyl-2,2-dimethyl-propyl)-amide

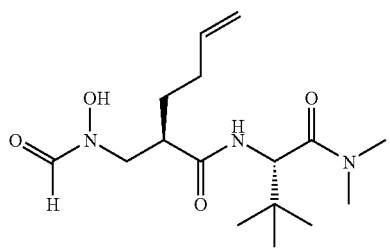

Diastereoisomer A: colourless oil. $^1$H-NMR; δ (CDCl$_3$, rotamers), 8.42 (0.45H, s), 7.84 (0.55H, s), 6.78 (0.45H, d, J=8.4 Hz), 6.60 (0.55H, d, J=9.3 Hz), 5.74 (1H, m), 5.03 (2H, m), 4.88 (1H, m), 4.14 (0.4H, m), 3.81 (0.6H, m), 3.55 (1H, m), 3.16 (1H, s), 3.15 (2H, s), 2.98 (1H, s), 2.97 (2H, s), 2.85 (0.7H, m), 2.68 (0.3H, m), 2.07 (2H, m), 1.73 (1.6H, m), 1.50 (0.4H, m), 0.99 (4H, s) and 0.95 (5H, s). LRMS: +ve ion 350 [M+Na], −ve ion 326 [M−H].

Diastereoisomer B: colourless oil. $^1$H-NMR; δ (CDCl$_3$, rotamers), 8.41 (0.5H, s), 7.75 (0.5H, s), 6.58 (0.5H, d, J=9.1 Hz), 6.36 (0.5H, d, J=9.1 Hz), 5.75 (1H, m), 5.01 (2H, m), 4.86 (0.5H, d, J=9.5 Hz), 4.64 (0.5H, d, J=7.5 Hz), 3.42-3.82 (2H, m), 3.22 (1.5H, s), 3.07 (1.5H, s), 2.99 (3H, s), 2.87 (0.5H, m), 2.66 (0.5H, m), 2.13 (2H, m), 1.81 (1H, m), 1.49 (1H, m), 1.02 (4.5H, s) and 1.00 (4.5H, s). LRMS: +ve ion 350 [M+Na], −ve ion 326 [M−H].

EXAMPLE 68

2R-[(Formyl-hydroxy-amino)-methyl]-hex-4-ynoic acid (1S-dimethylcarbamoyl-2,2-dimethyl-propyl)-amide

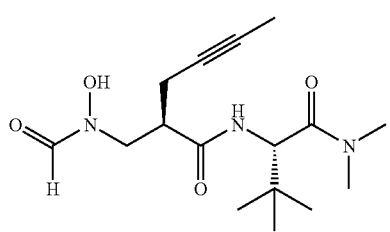

Diastereoisomer A: colourless oil. $^1$H-NMR; δ (CDCl$_3$, rotamers), 8.39 (0.4H, s), 7.87 (0.6H, s), 7.20 (0.4H, d, J=8.4 Hz), 6.94 (0.6H, d, J=9.3 Hz), 4.90 (1H, m), 3.66-4.14 (2H, m), 3.16 (2H, s), 3.14 (2H, s), 2.96 (3H, s), 2.88 (1H, m), 2.41 (2H, m), 1.77 (3H, m), 1.00 (3.5H, s) and 0.96 (5.5H, s). LRMS: +ve ion 348 [M+Na], −ve ion 324 [M−H].

Diastereoisomer B: Colourless oil. $^1$H-NMR; δ (CDCl$_3$, rotamers), 8.37 (0.5H, s), 7.81 (0.5H, s), 6.87 (1H, m), 4.91 (0.5H, d, J=9.4 Hz), 4.79 (0.5H, d, J=8.2 Hz), 3.76 (1.5H, m), 3.63 (0.5H, m), 3.19 (1.5H, s), 3.14 (1.5H, s), 2.98 (3H, s), 2.85 (1H, s), 2.41 (2H, m), 1.77 (3H, m), 1.03 (4.5H, s) and 1.01 (4.5H, s). LRMS: +ve ion 348 [M+Na], −ve ion 324 [M−H].

EXAMPLE 69

2R-[1R (or S)-(Formyl-hydroxy-amino)-ethyl]-hexanoic acid (1S-dimethylcarbamoyl-2,2-dimethylpropyl)-amide

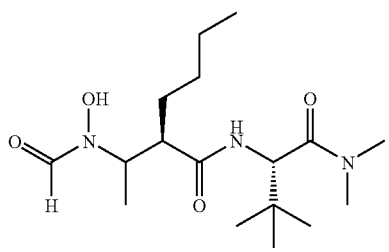

The title compound was prepared according to the route outlined in Scheme 5 and as described in detail below:

Scheme 5

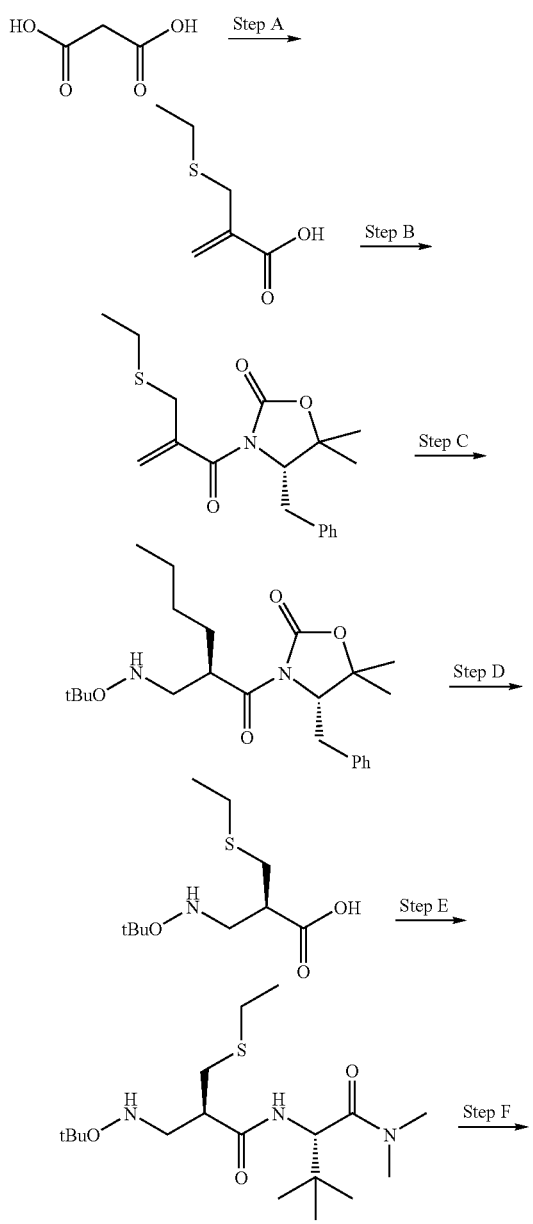

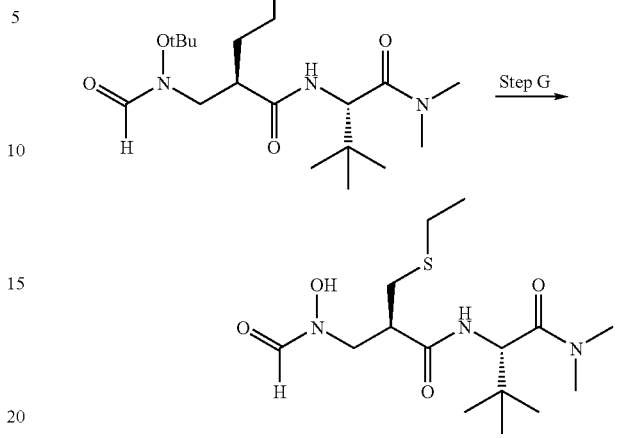

Reagents and conditions:
A. (CHO)$_n$, EtSH, dicyclohexylamine, dioxane, 70° C., 2 h;
B. $^t$BuCOCl, Et$_3$N then 3-lithio-4-benzyl-5,5-dimethyl-oxazolidin-2-one;
C. HCl•H$_2$NO$^t$Bu, Et$_3$N, o/n;
D. LiOH, aq THF, 0° C.;
E. H-t-LeuNMe$_2$, HOAt, EDC, DMF;
F. HCOAc, CH$_2$Cl$_2$;
G. TFA, CDCl$_3$.

Step A: 4-Benzyl-3-hexanoyl-oxazolidin-2-one

4S-Benzyl-oxazolidin-2-one (14.5 g, 81.7 mmol) was dissolved in dry THF (75 ml) under an argon atmosphere. The solution was cooled in an ice bath before slow addition of n-butyllithium (1.6 M in hexanes, 56 ml, 89.2 mmol). The lithium salt crystallised from the solution as a solid mass and was allowed to warm to room temperature overnight. The resulting orange suspension was cooled again in an ice bath during the addition of a cold solution of hexanoyl chloride (10.4 ml, 74.3 mmol) in dry THF (50 ml). The mixture was left to warm to room temperature and was then stirred for 3 hours. The reaction was quenched with 1M sodium carbonate solution (5 ml) and the solvent was removed under reduced pressure. The residue was partitioned between 1 M sodium carbonate (100 ml) and ethyl acetate (150 ml). The organic layer was removed and the aqueous layer was extracted with more ethyl acetate. The combined organic layers were washed successively with water, 1 M sodium carbonate and brine, dried over anhydrous magnesium sulphate and filtered. The filtrate was concentrated to leave an orange oil. Purification by flash chromatography afforded the title compound as a yellow oil (10.21 g, 50%). $^1$H-NMR; δ (CDCl$_3$), 7.38-7.24 (3H, m), 7.24-7.16 (2H, m), 4.68 (1H, m), 4.24-4.12 (2H, m), 3.30 (1H, dd, J=13.4, 3.2 Hz), 3.02-2.86 (2H, m), 2.77 (1H, dd, J=13.4, 9.6 Hz), 1.77-1.63 (2H, m), 1.44-1.30 (4H, m) and 0.92 (3H, br t, J=6.9 Hz).

Step B: 1-(4S-Benzyl-2-oxo-oxazolidin-3-yl)-2R-butyl-butane-1,3-dione

4-Benzyl-3-hexanoyl-oxazolidin-2-one (10.2 g, 37.1 mmol) was dissolved in THF (150 ml) under an argon atmosphere and cooled to −78° C. Lithium hexamethyldisilazide (1 M in THF, 41 ml, 41 mmol) was added via a cannula over a few minutes and the resulting green solution was stirred at −78° C. for 2 hours. Acetyl chloride (3.3 ml, 46.3 mmol) was added slowly and the reaction mixture was stirred for 3.5 hours. A solution of citric acid (3.0 g, 14 mmol) in water (15 ml) was added quickly to quench the reaction. The solvent was removed under reduced pressure and the residue was partitioned between ethyl acetate and water, washed with brine, dried over anhydrous magnesium sulphate and filtered. The filtrate was concentrated to provide the title compound as a yellow oil (12.11 g, contains residual solvent) which was used without further purification in Step C. $^1$H-NMR; δ (CDCl$_3$), 7.37-7.21 (5H, m), 4.68 (1H, m), 4.53 (1H, dd, J=9.6, 3.7 Hz), 4.23-4.13 (2H, m), 3.43 (1H, dd, J=13.5, 3.3 Hz), 2.75 (1H, dd, J=13.5, 9.9 Hz), 2.33 (3H, s), 2.03 (1H, m), 1.77 (1H, m), 1.46-1.26 (4H, m) and 0.98-0.86 (3H, m).

Step C: 1-(4S-Benzyl-2-oxo-oxazolidin-3-yl)-2R-butyl-butane-1,3-dione 3-(O-benzyl-oxime)

To a solution of 1-(4S-benzyl-2-oxo-oxazolidin-3-yl)-2R-butyl-butane-1,3-dione (12.11 g, 38.15 mmol) in water (10 ml) and ethanol (90 ml) was added sodium acetate (3.75 g, 45.78 mmol) and O-benzyl hydroxylamine hydrochloride (7.31 g, 45.78 mmol). The resulting suspension was left to stir at room temperature overnight. The product (7.3 g, 45%, single oxime isomer) crystallised directly from the reaction and was filtered, washed with aqueous ethanol (1:1) and dried under vacuum. Further material (5.31 g, 33%, mixture of oxime isomers) was obtained as a yellow oil from the mother liquors by acid-base extraction followed by column chromatography. $^1$H-NMR; δ (CDCl$_3$, major oxime isomer), 7.34-7.20 (8H, m), 7.12-7.07 (2H, m), 5.14-5.02 (2H, m), 4.53 (1H, m), 4.13 (1H, dd, J=9.4, 4.0 Hz), 4.04 (1H, br t, J=8.4 Hz), 3.91 (1H, dd, J=9.0, 2.7 Hz), 3.16 (1H, dd, J=13.4, 2.9 Hz), 2.09 (3H, s), 1.97 (1H, m), 1.75 (1H, dd, J=3.4, 10.8 Hz), 1.67 (1H, m), 1.45-1.22 (4H, m) and 0.91 (3H, br t, J=6.9 Hz).

Step D: 4S-Benzyl-3-[2R-(1R (or S)-benzyloxyamino-ethyl)-hexanoyl]-oxazolidin-2-one The mixture of oximes form Step C (5.31 g, 12.5 mmol) was dissolved in acetic acid (30 ml) and cooled in an ice-water bath before addition of sodium cyanoborohydride (0.8 g, 12.5 mmol) in one portion. Effervescence subsided after a few minutes and a further portion of borohydride (0.8 g) was added. The reaction was allowed to warm to room temperature and stirred overnight. The acetic acid was removed under reduced pressure and the residue was azeotroped with toluene. The resulting oil was dissolved in ethyl acetate, washed with water, 1 M sodium carbonate and brine, dried over anhydrous magnesium sulphate and filtered. The filtrate was evaporated to leave a pale yellow oil which was purified by flash chromatography (silica gel, 10% to 25% ethyl acetate in hexane as eluant). Yield 3.43 g, 64%). $^1$H-NMR; δ (CDCl$_3$, mixture of α-diastereoisomers), 7.36-7.17 (10H, m), 5.80 (0.45H, br s), 5.55 (0.55H, br d, J=8.9 Hz), 4.72-4.59 (3H, m), 4.20-4.05 (2H, m), 3.97 (0.45H, m), 3.82 (0.55H, m), 3.47-3.22 (2H, m), 2.45 (1H, m), 1.90-1.48 (2H, m), 1.40-1.14 (7H, m) and 0.95-0.84 (3H, m).

Step E: N-[2R-(4S-Benzyl-2-oxo-oxazolidine-3-carbonyl)-1R (or S)-methyl-hexyl]-N-benzyloxy-formamide 4S-Benzyl-3-[2R-(1R (or S)-benzyloxyamino-ethyl)-hexanoyl]-oxazolidin-2-one (3.08 g, 7.3 mmol) was dissolved in dry THF and treated with N-formylbenzotriazole (1.60 g, 10.9 mmol). The reaction was stirred for 4 hours at room temperature. The solvent was removed under reduced pressure and the remaining oil was partitioned between dichloromethane (40 ml) and 1 M sodium hydroxide solution (30 ml). The organic layer was removed, washed with more sodium hydroxide then brine, dried over anhydrous magnesium sulphate, filtered and evaporated. Purification by flash chromatography (silica gel, 20% to 50% ethyl acetate in hexane) gave the title compound as a pale yellow solid (2.50 g, 76%). $^1$H-NMR; δ (CDCl$_3$, mixture of α-diastereoisomers and rotamers), 8.22 (1H, br m), 7.54-7.13 (10H, m), 5.22-3.92 (7H, br m), 3.30 (1H, m), 2.48 (1H, br m), 1.85-1.13 (9H, br m) and 0.93-0.83 (3H, m).

Step F: 2R-[1R (or S)-(Benzyloxy-formyl-amino)-ethyl]-hexanoic acid

N-[2R-(4S-Benzyl-2-oxo-oxazolidine-3-carbonyl)-1R (or S)-methyl-hexyl]-N-benzyloxy-formamide (1.50 g, 3.31 mmol) was dissolved in THF (25 ml) and water (5 ml) and the solution was cooled in an ice-water bath. Hydrogen peroxide solution (27% w/w), 13.26 mmol) was added followed immediately by lithium hydroxide (167 mg, 3.98 mmol). The reaction was allowed to warm to room temperature and stirred for a further 3 hours. The solution was cooled again before addition of sodium nitrite (0.92 g, 13.3 mmol). After 10 minutes, most of the solvent was removed under reduced pressure to leave a white paste which was partitioned between ethyl acetate (25 ml) and 1M sodium carbonate (30 ml). The organic layer was washed with more sodium carbonate solution and the combined aqueous extracts were washed with ethyl acetate. The aqueous layer was cooled and acidified with 1 M hydrochloric acid and extracted twice with ethyl acetate. The combined organic layers were washed with brine, dried over anhydrous magnesium sulphate, filtered and evaporated to provide the title compound as a green oil (839 mg, 86%). $^1$H-NMR; δ (CDCl$_3$, mixture of α-diastereoisomers and rotamers), 8.40-7.64 (2H, br m), 7.48-7.27 (5H, m), 5.23-4.80 (2H, m), 4.16 (1H, br m), 2.79 (1H, m), 1.67-1.47 (2H, m), 1.47-1.18 (7H, m) and 0.95-0.82 (3H, m).

Step G: 2R-[1R (or S)-(Benzyloxy-formyl-amino)-ethyl]-hexanoic acid (1S-dimethyl-carbamoyl-2,2-dimethyl-propyl)-amide 2R-[1R (or S)-(Benzyloxy-formyl-amino)-ethyl]-hexanoic acid (839 mg, 2.86 mmol), tert-leucine N,N-dimethyl amide (498 mg, 3.15 mmol) and EDC (658 mg, 3.43 mmol) were dissolved together in DMF (15 ml) and a catalytic amount of HOAt (60 mg) was added. The solution was left to stir for several days at room temperature. The solvent was removed under reduced pressure and the remaining oil was partitioned between ethyl acetate and 1 M hydrochloric acid (75 ml). The organic layer was washed successively with 1 M hydrochloric acid, 1 M sodium carbonate and brine, dried over anhydrous magnesium sulphate filtered and evaporated to leave a yellow foam (1.08 g, 82%). $^1$H-NMR; δ (CDCl$_3$, mixture of α-diastereoisomers and rotamers), 8.13 (1H, br m), 7.52-7.31 (5H, m), 6.28 (1H, br m), 5.36-4.67 (3H, br m), 4.09 (1H, br m), 3.14 (3H, s), 2.95 (1.2H, s), 2.93 (1.8H, s), 2.48 (1H, br m), 1.61-1.04 (9H, m), 0.99 (3.6H, s), 0.95 (5.4H, s) and 0.89-0.75 (3H, m).

Step H: 2R-[1R (or S)-(Formyl-hydroxy-amino)-ethyl]-hexanoic acid (1S-dimethyl-carbamoyl-2,2-dimethyl-propyl)-amide 2R-[1R (or S)-(Benzyloxy-formyl-amino)-ethyl]-hexanoic acid (1S-dimethyl-carbamoyl-2,2-dimethyl-propyl)-amide (200 mg, 0.46 mmol) was dissolved in methanol (15 ml) and placed under a blanket of argon. A suspension of 10% palladium on charcoal (20 mg) in ethyl acetate was added and the mixture was stirred under an atmosphere of hydrogen for 3 hours. The catalyst was removed by filtration and the filtrate was evaporated to leave a colourless oil (163 mg, quant.). The two diastereoisomeric products were separated by preparative HPLC.

Diastereoisomer A (27 mg): $^1$H-NMR; δ (CDCl$_3$, mainly one rotamer), 8.67 (0.9H, br s), 8.33 (0.1H, br s), 7.92 (1H, s), 6.74 (0.1H, br m), 6.54 (0.9H, d, J=9.4 Hz), 4.93 (0.9H, d, J=9.4 Hz), 4.64 (0.1H, br m), 3.89 (1H, qd, J=6.6, 2.6 Hz), 3.16 (3H, s), 2.96 (3H, s), 2.62-2.48 (1H, m), 1.52-1.06 (6H, m), 1.35 (3H, d, J=6.6 Hz), 1.00 (9H, s), and 0.82 (3H, t, J=6.9 Hz). $^{13}$C-NMR; δ (CDCl$_3$), 173.0, 171.3, 57.2, 54.4, 50.4, 38.4, 35.6, 29.9, 29.1, 26.6, 22.5, 17.2 and 13.9. LRMS: +ve ion 366 [M+Na], −ve ion 342 [M−H].

Diastereoisomer B (42 mg): $^1$H-NMR; δ (CDCl$_3$, mixture of rotamers), 9.15 (0.6H, s), 8.60 (0.4H, br s), 8.42 (0.6H, s), 7.84 (0.4H, s), 6.83 (0.6H, d, J=9.2 Hz), 6.55 (0.4H, d, J=9.4 Hz), 4.91 (0.6H, d, J=9.2 Hz), 4.89 (0.4H, d, J=9.4 Hz), 4.69 (0.6H, qd, J=7.0, 4.3 Hz), 3.92 (0.4H, dq, J=9.1, 6.8 Hz), 3.15 (3H, s), 2.97 (1.8H, s), 2.95 (1.2H, s), 2.59 (0.4H, td, J=9.8, 4.3 Hz), 2.39 (0.6H, td, J=7.4, 4.3 Hz), 1.92-1.07 (6H, m), 1.37 (1.2H, d, J=6.8 Hz), 1.31 (1.8H, d, J=7.0 Hz), 1.01 (5.4H, s), 0.96 (3.6H, s), 0.85 (1.8H, t, J=7.2 Hz) and 0.83 (1.2H, t, J=7.2 Hz). $^{13}$C-NMR; δ (CDCl$_3$, mixture of rotamers), 175.7, 173.2, 171.3, 170.7, 56.7, 55.0, 54.4, 53.2, 50.8, 49.9, 38.3, 35.7, 35.6, 35.5, 35.4, 30.3, 29.5, 29.3, 26.5, 26.4, 22.5, 22.4, 16.0, 15.4 and 13.8. LRMS: +ve ion 366 [M+Na], −ve ion 342 [M−H].

EXAMPLE 70

N-cyclohexyl-2-{2-[(formyl-hydroxy-amino)-methyl]-3-phenyl-propionylamino}-3,3-dimethyl-butyramide

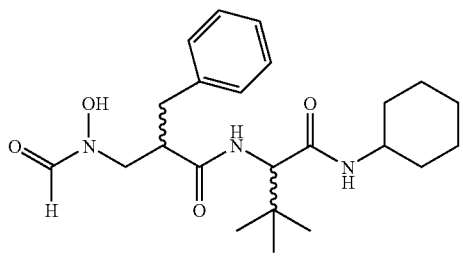

Stock solutions of 1 M ammonia in methanol (1 ml, 1 mmol) and 1 M trimethylacetaldehyde in methanol (1 ml, 1 mmol) were mixed in a boiling tube and allowed to stand for 1 hour. A 1 M solution of cyclohexyl isocyanide in methanol (1 ml, 1 mmol) was added followed by 0.5 M 2RS-[(benzyloxy-formyl-amino)-methyl]-hexanoinc acid in methanol (2 ml, 1 mmol). The reaction mixture was allowed to stir at room temperature for 2 days. The solvent was removed using a Savant Speedvac and the reaction mixture was crystallised from ethylacetate-hexane to provide 2-{2-[(benzyloxy-formyl-amino)-methyl]-3-phenyl-propionylamino}-N-cyclohexyl-3,3-dimethyl-butyramide as a white solid (93 mg, 18%), which was deprotected by catalytic transfer hydrogenolysis (hydrogen gas, 10% palladium on charcoal, methanol-ethyl acetate) to provide the title compound (75 mg, 99%). White solid. LRMS: +ve ion 440 [M+Na], 418 [M+H], −ve ion 416 [M−H].

The compounds of Examples 71 to 77 were prepared in parallel using the Ugi 4 component condensation reaction, as described above. All products were obtained in >85% purity as determined by HPLC.

EXAMPLE 71

2-{2-[(Formyl-hydroxy-amino)-methyl]-3-phenyl-propionylamino}-3,3-dimethyl-hexanoic acid cyclohexyl amide

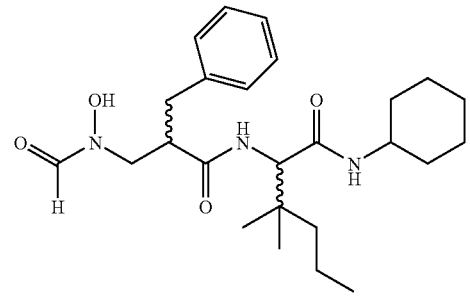

White solid (90 mg). $^1$H-NMR; δ (CD$_3$OD), 7.82 (1H, s), 7.29-7.08 (5H, m), 4.20 (1H, d, J=5.0 Hz), 3.89 (1H, m), 3.19 (1H, m), 2.95-2.67 (2H, m), 1.88-1.58 (5H, br m), 1.44-1.05 (9H, br m) and 0.89 (9H, s). LRMS: +ve ion 468 [M+Na], 446 [M+H], −ve ion 444 [M−H].

EXAMPLE 72

2-{2-[(Formyl-hydroxy-amino)-methyl]-3-phenyl-propionylamino}-3,3-dimethyl-hexanoic acid phenylmethyl amide

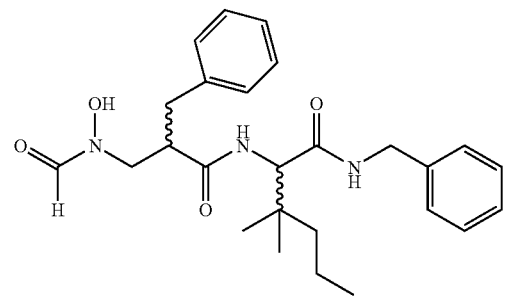

White solid (77 mg). $^1$H-NMR; δ (CD$_3$OD), 7.82 (1H, s), 7.35-7.11 (10H, m), 4.38-4.19 (3H, m), 3.85 (1H, m), 3.52 (1H, m), 2.97-2.63 (3H, m), 1.37-1.11 (4H, m) and 0.93-0.78 (9H, m). LRMS: +ve ion 476 [M+Na], 454 [M+H].

EXAMPLE 73

2-{2-[(Formyl-hydroxy-amino)-methyl]-3-phenyl-propionylamino}-3,3-dimethyl-butyric acid tert-butyl amide

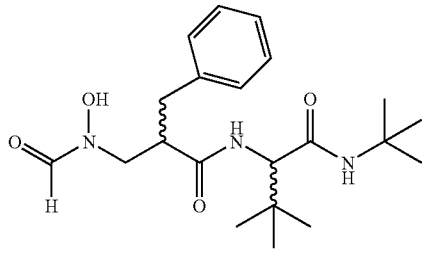

White solid (47 mg). ¹H-NMR; δ (CD₃OD), 7.82 (1H, s), 7.45 (1H, m), 7.30-7.09 (5H, m), 4.12 (1H, d, J=7.2 Hz), 3.89 (1H, m), 3.41 (1H, m), 3.15 (1H, m), 2.97-2.68 (2H, m), 1.28 (9H, s) and 0.92 (9H, s). LRMS: +ve ion 414 [M+Na], 392 [M+H], −ve ion 390 [M−H].

EXAMPLE 74

2-{2-[(formyl-hydroxy-amino)-methyl]-3-phenyl-propionylamino}-3,3-dimethyl-hexanoic acid (1,1,3,3-tetramethyl)-butyramide

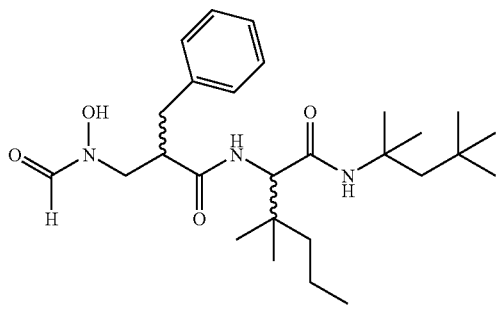

White solid (65 mg). ¹H-NMR; δ (CD₃OD), 7.79 (1H, s), 7.42-7.21 (1H, m), 7.20-7.10 (5H, m), 4.23 (1H, d, J=9.1 Hz), 3.86 (1H, m), 3.51 (1H, m), 3.23 (1H, m), 3.00-2.56 (2H, m), 1.50-1.15 (12H, m) and 1.02-0.83 (18H, m). LRMS: +ve ion 498 [M+Na], 476 [M+H, −ve ion 474 [M−H].

EXAMPLE 75

N-(Cyclohexyl-cyclohexylcarbamoyl-methyl)-2-[(formyl-hydroxy-amino)-methyl]-3-phenyl-propionamide

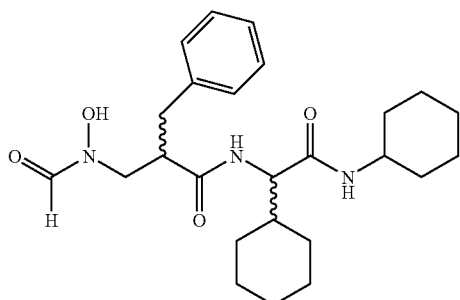

White solid (98 mg). ¹H-NMR; δ (CD₃OD), 7.38-7.08 (5H, m), 4.01 (1H, m), 3.81 (1H, m), 3.68-3.35 (2H, m), 3.15 (1H, m), 2.98-2.65 (2H, m), 1.88-1.49 (10H, br m) and 1.45-0.83 (11H, br m). LRMS: +ve ion 466 [M+Na], 444 [M+H], −ve ion 442 [M−H].

EXAMPLE 76

N-(Cyclohexyl-phenylmethylcarbamoyl-methyl)-2-[(formyl-hydroxy-amino)-methyl]-3-phenyl-propionamide

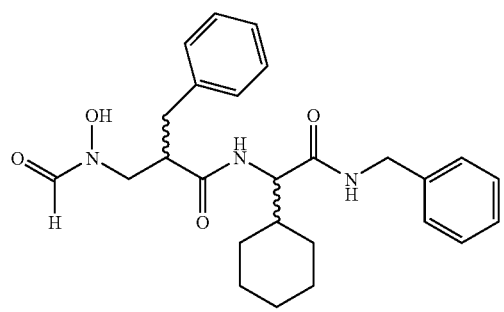

White solid (34 mg). ¹H-NMR; δ (CD₃OD), 7.35-7.10 (10H, m), 4.44-4.23 (2H, m), 4.05 (1H, m), 3.87-3.35 (2H, m), 3.09 (1H, m), 2.85-2.72 (2H, m), 1.65-1.46 (4H, m), 1.38-0.93 (5H, br m) and 0.75-0.51 (2H, br m). LRMS: +ve ion 474 [M+Na], −ve ion 450 [M−H].

EXAMPLE 77

N-[Cyclohexyl-(1,1,3,3-tetramethyl-butylcarbamoyl)-methyl]-2-[(Formyl-hydroxy-amino)-methyl]-3-phenyl-propionamide

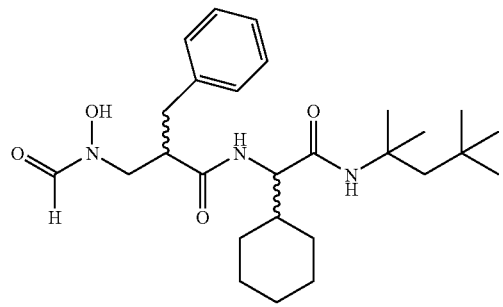

White solid (51 mg). ¹H-NMR; δ (CD₃OD), 7.80 (1H, s), 7.36-7.10 (5H, m), 4.05 (1H, m), 3.85 (1H, m), 3.49 (1H, m), 3.15 (1H, m), 2.91 (1H, m), 2.68 (1H, m), 1.90 (1H, m), 1.80-1.48 (7H, m), 1.40-1.12 (10H, m) and 1.08-0.83 (10H, m). LRMS: +ve ion 496 [M+Na], 474 [M+H], −ve ion 472 [M−H].

BIOLOGICAL EXAMPLE A

Demonstration of Antibacterial Effect of Compound 1 (Example 1) and Compound 2 (Example 13).

a).

Minimal inhibitory concentrations (MIC) of inhibitors against *E. coli* strain DH5α (Genotype; F-φ80dlacZΔM15Δ (lacZYA-argF)U169 deoR recA1 endA1 hsdR17($r_k^-$,$m_k^+$) phoA supE44λ⁻ thi-1 gyrA96 relA1) obtained from Gibco-BRL Life Technologies, *Enterobacter cloacae* (American Type Culture Collection number 13047), *Klebsiella pneumoniae* (American Type Culture Collection number 13883) or *Staphylococcus capitis* (American Type Culture Collection number 35661) were determined as follows. Stock solutions of test compound (Compounds 1 and 2 from Examples 1 and 2 respectively (both isomer A)) and three standard laboratory antibiotics, carbenicillin (Sigma, catalogue No. C3416), kanamycin (Sigma, catalogue No. K4000) and chloramphenicol (Sigma, catalogue No. C1919), were prepared by dissolution of each compound in dimethylsulfoxide at 10 mM. For the determination of the minimal inhibitory concentration, two fold serial dilutions were prepared in 2×YT broth (typtone 16 g/l, yeast extract 10 g/l, sodium chloride 5 g/l obtained from BIO 101 Inc, 1070 Joshua Way, Vista, Calif. 92083, USA) to yield 0.05 ml compound-containing medium per well. Inocula were prepared from cultures grown overnight in 2×YT broth at 37° C. Cell densities were adjusted to absorbance at 660 nm ($A_{660}$)=0.1; the optical density-standardized preparations were diluted 1:1000 in 2×YT broth; and each well inoculated with 0.05 ml of the diluted bacteria. Microtiter plates were incubated at 37° C. for 18 hours in a humidified incubator. The MIC (µM) was recorded as the lowest drug concentration that inhibited visible growth.

TABLE 1

| | MIC µM | | | | |
|---|---|---|---|---|---|
| | carbenicillin | chloramphenicol | kanamycin | compound 1 | compound 2 |
| E. coli DH5α | 25 | 3.12 | 12.5 | 12.5 | 6.25 |
| Staphylococcus capitis | <1.56 | 6.25 | <1.56 | 100 | 25 |
| Enterobacter cloacae | >200 | 25 | 50 | 50 | 25 |
| Klebsiella pneumoniae | 200 | 12.5 | 25 | 25 | 12.5 | b).

Minimal inhibitory concentrations (MIC) of inhibitors against Mycobacterium ranae (American Type Culture Collection number 110), Pseudomonas aeruginosa (American Type Culture Collection number 9027), Klebsiella pneumoniae (American Type Culture Collection number 10031), Helicobacter pylori (American Type Culture Collection number 43504), clinical isolates of aminoglycoside and erythromycin resistant Streptococcus pneumoniae and methicillin-resistant (MR) Staphylococcus aureus (American Type Culture Collection number 33591) were determined as follows. Stock solutions of test compounds 1 and 2 (isomer A for each) and three standard laboratory antibiotics, gentamycin (G), ampicillin (A) and erythromycin (E), were prepared by dissolution of each compound at 10 mg/ml in dimethylsulfoxide. Methods used were as for a) except that the medium of Mycobacterium ranae was used with Brain Heart Infusion broth (GIBCO) and incubated at 37° C. for 48 hours, Staphylococcus aureus (MR), Klebsiella pneumoniae, and Pseudomonas aeruginosa were used with Nutrient Broth (DIFCO) and incubated at 37° C. for 20 hours, Helicobacter pylori was used with Columbia agar base (OXOID) containing 7% sheep blood and incubated at 35° C. for 72 hours and, Streptococcus pneumoniae was used with tryptic soy broth (DIFCO) containing 7% calf serum and incubated at 37° C. for 48 hours. The MIC (µg/ml) was recorded as the lowest drug concentration that inhibited visible growth.

Positive vehicle control (1% DMSO; no test agent) caused growth of all microorganisms.

Negative blank control (absence of microorganisms; +test agent) revealed no growth of microorganisms.

TABLE 2

| | MIC µg/ml | | | | |
|---|---|---|---|---|---|
| | | | | antibiotic | |
| | compound 1. | compound 2. | G | A | E |
| M. ranae | 0.78 | 0.2 | 0.2 | nd | nd |
| S. aureus (MR) | 3.13 | 1.56 | 0.78 | nd | nd |
| K. pneumoniae | 0.2 | 0.1 | 0.39 | nd | nd |
| P. aeruginosa | 12.5 | 12.5 | 0.78 | 100 | nd |
| H. pylori | 0.1 | 0.1 | 0.78 | 0.1 | nd |
| S. pneumoniae | 50 | 12.5 | 100 | 3.13 | 100 | nd = not determined.

In another experiment, minimal inhibitory concentrations of compounds 1 and the product of Example 13 (compound 3) against a range of Gram-positive and Gram-negative bacteria were determined using the Microdilution Broth Method according to the approved standard of the National Committee for Clinical Laboratory Standards procedure (Methods for dilution antimicrobial susceptibility tests for bacteria that grow aerobically-Fourth Edition ISBN 1-56238-309-4)

| Activity against Gram-positive bacteria | | | |
|---|---|---|---|
| | MIC µg/ml | | |
| Bacterial Strain | Compound 3 | Compound 1 | Vancomycin |
| Staphylococcus aureus ATCC 29213 MSSA | 8 | 32 | 0.25 |
| Staphylococcus aureus ATCC 25923 MSSA | 16 | 16 | 0.5 |
| Staphylococcus aureus ATCC 6538 MSSA | 4 | 8 | 0.5 |
| Staphylococcus epidermidis ATCC 1228 | 4 | 8 | 0.5 |
| Staphylococcus epidermidis ATCC 27626 | 2 | 8 | 0.5 |
| Enterococcus faecalis ATCC 29212 | 32 | 32 | 1 |
| Enterococcus faecalis (Vancomycin resistant strain) | 8 | 128 | >128 |
| Micrococcus luteus ATCC 9341 | 0.5 | 0.5 | 0.25 |

Activity against Gram-negative bacteria

| Bacterial Strain | MIC μg/ml | | |
|---|---|---|---|
| | Compound 3 | compound 1 | Ciprofloxacin |
| *Escherichia coli* ATCC 25922 | 4 | 4 | <0.125 |
| *Escherichia coli* ATCC 12014 | 4 | 4 | <0.125 |
| *Pseudomonas aeruginosa* ATCC 27853 | 128 | >128 | <0.125 |
| *Enterobacter cloacae* ATCC 13047 | 32 | 32 | <0.125 |
| *Morganella morganii* ATCC 36030 | >128 | 128 | <0.125 |
| *Klebsiella pneumoniae* ATCC 13883 | 16 | 16 | <0.125 |

The activities of compound 3 and the product of Example 14 (compound 4) against a multi-resistant *Enterococcus faecalis* clinical isolate, assessed by the method used for the immediately preceding results, are set out in the following table, and compared with the results obtained by the same method for known antibacterial agents:

Activity against a multi-resistant *Enterococcus faecalis* clinical isolate:

| Bacterial Strain | MIC μg/ml | | | | | | | |
|---|---|---|---|---|---|---|---|---|
| | Cpd 3 | Cpd 4 | Ampicillin | Ceftazidime | Imipenem | Erythromycin | Ciprofloxacin | Vancomycin |
| *Enterococcus faecalis* ATCC 29212 | 32 | 8 | 0.5 | 128 | 1 | 2 | 0.5 | 1 |
| *Enterococcus faecalis* Vancomycin resistant strain | 8 | 4 | >128 | >128 | >128 | >128 | >128 | >128 | fitted with a medium probe and at an amplitude of 20-25 microns in 6×20 second pluses. The resulting suspension was then cleared by centrifugation at 20,000×g for 15 minutes. The supernatant was then used for further purification of the enzyme.

iv) PDF Purification

*E. coli* lysate from a 1 l culture in phosphate buffered saline (PBS) were adjusted to 2M ammonium sulphate. A 15 ml phenyl sepharose column was equilibrated with PBS/2M ammonium sulphate at 4° C. The lysate was loaded on the column and washed with equilibration buffer. The column was eluted by reducing the ammonium sulphate concentration from 2M to 0M over 10 column volumes. 5 ml fractions were collected and analysed by SDS-PAGE. The fractions containing the majority of the 20 kDa PDF were pooled. The pooled fractions were concentrated using a 3 kDa cutoff membrane to a volume of 5 ml. The fraction was then loaded onto a Superdex 75 (size exclusion chromatography) column equilibrated in PBS. The concentrated PDF pool eluted at one ml/min at 4° C. and 5 ml fractions collected and analysed by SDS-PAGE. The purest fractions were pooled and stored at −70° C.

(v) PDF In Vitro Assay

The assay was performed in a single 96 well plate in a final volume of 100 μl containing:

20 μl PDF (4 μg/ml)

20 μl 100 mM Hepes pH 7.0+1M KCl+0.05% Brij

BIOLOGICAL EXAMPLE B i) Cloning of the *Escherichia coli* PDF Gene.

The *E. coli* PDF gene was cloned in pET24a(+) (designated pET24-PDF) and was used to transform BL21 DE3 cells from Novagen Inc, (Madison, Wis.). Clones were selected at 37° C. on YT agar plates (8 g/l typtone, 5 g/yeast extract, NaCl 5 g/l, agar 15 g/l) supplemented with 30 μg/ml kanamycin.

ii) Expression of PDF

A 20 ml overnight culture of BL21 DE3 cells harbouring pET24-PDF was used to infect 500 ml 2×YT broth (16 g/l typtone, 10 g/l yeast extract, NaCl 5 g/l) containing 30 ug/ml kanamycin in a 2 liter baffled flask and grown at 37° C. with shaking to an $OD_{600}$ 0.6. The culture was then induced by adjusting the medium to 1.0 mM isopropyl β-D thiogalactopyranoside (IPTG). The induction was allowed to proceed for a further 3 hours at 37° C., the cells were harvested by centrifugation and the cell pellet washed with 250 ml phosphate buffered saline (PBS) and the pellet stored at −70° C.

iii) Preparation of Soluble Protein Fraction.

The cells from a 1 liter expression were resuspended in 2×25 ml of ice cold phosphate buffered saline. The cell suspension was sonicated on ice using an MSE Soniprep 150

10 μl serial dilution of test compound in 20% DMSO

50 μl formyl-Met-Ala-Ser (8 mM)

The assay was incubated at 37° C. for 30 minutes. The free amino group of the deformylated (Met-Ala-Ser) product was detected using fluorescamine, by the following additions:

50 μl 0.2M borate pH 9.5

50 μl fluorescamine (150 μg/ml in dry dioxane)

Fluorescence was quantified on SLT Fluostar plate reader using an excitation wavelength of 390 nM and an emission wavelength of 485 nM. Standard control reactions are a no inhibitor reaction which provides the zero inhibition figure and a no enzyme and no inhibitor reaction which provides the 100% inhibition figure. The data was analysed by conversion of the fluorescence units to % inhibition and the inhibitor concentration plotted against % inhibition. The data was fitted to a sigmoidal function: $y = A + ((B-A)/(1+((C/x)^D)))$, wherein A represents zero inhibition, B represents 100% inhibition and C represents the $IC_{50}$, D represents the slope. The $IC_{50}$ represents the concentration of inhibitor (nM) required to decrease enzyme activity by 50%.

Compounds of the invention were found to inhibit bacterial PDF in vitro. In addition, actinonin (Sigma Cat. No. A-6671) was also found to inhibit bacterial PDF in vitro.

BIOLOGICAL EXAMPLE C

Demonstration that Compound 2 Inhibits PDF In Vivo.

1 Blocking the tRNAi-Met Transformylation Reaction Confers Resistance to Compound 2 (Diastereomer/Isomer A).

Trimethoprim specifically inhibits dihydrofolate reductase, thereby depressing the pools of tetrahydrofolate (THF) derivatives, including formyl tetrahydrofolate (fTHF), the substrate of the methionyl-tRNA formyltransferase (EC 2.1.2.9). If all essential metabolites whose biosynthesis involves THF derivatives, eg pantothenate, methionine, glycine, purine nucleotides and thymidine are supplied exogenously in the form of precursor compounds in rich medium supplemented with thymidine, then bacteria grown in rich medium plus thymidine (0.3 mM) and trimethoprim (100 µg/ml) can synthesize all the chemical components of normal cells except f-Met-tRNAi (Baumstark et al., J. Bacteriol. 129:457-471, 1977). Unformylated Met-tRNAi is used instead, resulting in the formation of polypeptides devoid of a formyl group at their N-terminus, independently of the action of deformylase. As predicted by the inventors, DH5α cells grown in LB medium (typtone 10 g/l, yeast extract 5 g/l NaCl 10 g/l pH7.5) supplemented with trimethoprim and thymidine, were found to be resistant to compound 2 (diastereomer A). The demonstration that cells that undergo the normal formylation process on expressed proteins are inhibited by compound 2A whereas, unformylated proteins, as produced in the cells grown under these conditions, are not inhibited by compound 2A demonstrates that compound 2A is likely to work by inhibiting the deformylation reaction carried out by PDF.

TABLE 3

| growth conditions | minimal inhibitory concentration µM |
| --- | --- |
| LB | 15 |
| LB trimethoprim (100 µg/ml), thymidine (0.3 mM) | >200 |

2 Treatment of Bacteria with Compound 2A Leads to the Accumulation of N-terminally Blocked Proteins.

If the compounds of the invention do actually inhibit PDF in vivo, then a consequence of treatment of bacteria with compound 2 (Example 2, diastereomer A) will be the accumulation of N-formyl methionine at the N-terminus of newly synthesised proteins. Such proteins will be N-terminally blocked and will be unable to be used as a substrate for N-terminal sequencing by Edman degradation chemistry.

To test this hypothesis a desired protein is expressed in the presence or absence of the test compound. The protein is isolated, purified and then subjected to Edman degradation protein sequencing using techniques known to the person-skilled in the art.

Bacterial cells transformed with an expression vector allowing expression of the human calpain small regulatory subunit, were grown to an $OD_{600}$ of 0.6 and then subjected to IPTG to induce expression of the heterologous protein in the presence of 200 µM compound 2A, in the presence of 240 µM carbenicillin or, in the presence of vehicle control for 2.5 hours. Protein extracts were separated by SDS-PAGE, the calpain subunit eluted and the protein sequence determined by Edman degradation chemistry using the ABI automated protein sequencer. Equal quantities of protein were sequenced. The inventors found that the yield of the compound 2A treated protein was significantly reduced by 85% compared to vehicle and carbenicillin treated controls.

Calpain small regulatory subunit was cloned from messenger RNA obtained from a gastric tumour biopsy using the InVitrogen Micro Fast Track™ mRNA isolation kit version 2.2 (catalogue number K1520-02). Copy DNA from this mRNA was synthesised using the Promega Riboclone™ cDNA synthesis system M-MLV-RT(H-), NotI (Promega, Catalogue number C1660) according to the manufactures instructions. Two oligonucleotide primers for use in the polymerase chain reaction (PCR) were synthesised by Applied Biosystems, Inc., Custom Services, based on the published calpain small subunit sequence (EMBL Accession number X04106).

The HindIII/XhoI calpain fragment was then cloned into HindIII and XhoI digested expression vector pET24d(+) from Novagen Inc, (Madison, Wis., USA) using standard procedures. The ligation mixture was used to transform competent DH5αcells (Life Technologies, Inc, Grand Island, N.Y., USACat #18265-017). Colonies were selected by growth overnight at 37° C. on YT plates plus 30 µg/ml kanamycin. Plasmid DNA was prepared as using the Promega Plus SV miniprep kit and clones with the calpain insert were identified using standard procedures. The DNA sequence was confirmed using the PE Applied Biosystems cycle sequencing as described above.

The *E. coli* gene cloned in pET24d(+) (designated pET24-CANS) was used to transform BL21 DE3 cells from Novagen Inc, (Madison, Wis.). Clones were selected at 37° C. on YT agar plates (8 g/l typtone, 5 g/yeast extract, NaCl 5 g/l, agar 15 g/l) supplemented with 30 µg/ml kanamycin.

The invention claimed is:

1. A compound of formula (I) or a pharmaceutically or veterinarily acceptable salt thereof

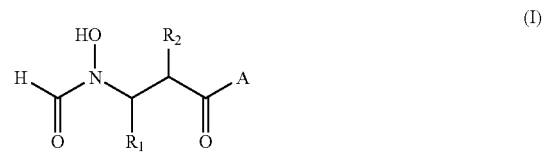

(I)

wherein
$R_1$ is methyl;
$R_2$ is n-butyl, benzyl, or cyclopentylmethyl;
A represents (i) a group of formula (IA):

(IA)

wherein:
$R_4$ is tert-butyl, isobutyl, benzyl, or methyl:
$R_5$ and $R_6$, independently represent hydrogen, or optionally substituted $C_1$-$C_8$ alkyl, cycloalkyl, aryl($C_1$-$C_6$ alkyl), non-aromatic heterocyclic, or heterocyclic($C_1$-$C_6$ alkyl) provided that at least one of $R_5$ and $R_6$ is other than hydrogen.

2. An antibacterial pharmaceutical or veterinary composition comprising a compound as claimed in claim 1, together with a pharmaceutically or veterinarily acceptable excipient or carrier.

* * * * *